US007232835B2

(12) United States Patent
Mehta et al.

(10) Patent No.: US 7,232,835 B2
(45) Date of Patent: Jun. 19, 2007

(54) 3,6-DISUBSTITUTED AZABICYCLO DERIVATIVES AS MUSCARINIC RECEPTOR ANTAGONISTS

(75) Inventors: Anita Mehta, Plainfield, IL (US); Arundutt Viswanatham Silamkoti, Secunderabad (IN); Bruhaspathy Miriyala, Andhra Pradesh (IN); Sudershan Kumar Arora, Maharashtra (IN); Boju Srinivasulu, Andhra Pradesh (IN); Bireshwar Mukherjee, West Bengal (IN); Jang Bahadur Gupta, Dusseldorf (DE)

(73) Assignee: Ranbaxy Laboratories Limited, Gurgaon, Haryana (IN)

( * ) Notice: Subject to any disclaimer, the term of this patent is extended or adjusted under 35 U.S.C. 154(b) by 0 days.

(21) Appl. No.: 10/537,851

(22) PCT Filed: Dec. 10, 2002

(86) PCT No.: PCT/IB02/05220

§ 371 (c)(1),
(2), (4) Date: May 5, 2006

(87) PCT Pub. No.: WO2004/052857

PCT Pub. Date: Jun. 24, 2004

(65) Prior Publication Data

US 2006/0217432 A1  Sep. 28, 2006

(51) Int. Cl.
*A01N 43/40* (2006.01)
*A01N 43/00* (2006.01)
*A61K 31/445* (2006.01)
*A61K 31/55* (2006.01)
*C07D 221/02* (2006.01)

(52) U.S. Cl. ............... 514/323; 514/214.01; 540/584; 546/112

(58) Field of Classification Search ............... 540/584; 546/112; 514/323, 214.01
See application file for complete search history.

(56) References Cited

U.S. PATENT DOCUMENTS

| 3,176,019 | A | 3/1965 | Campbell et al. ...... 260/293.4 |
| 5,281,601 | A | 1/1994 | Cross et al. ............... 514/320 |
| 5,397,800 | A | 3/1995 | Alker et al. ............... 514/413 |
| 5,703,091 | A | 12/1997 | Steiner et al. ............. 514/300 |
| 5,914,338 | A | 6/1999 | Jeppesen et al. .......... 514/362 |
| 5,948,792 | A | 9/1999 | Tsuchiya et al. ......... 514/317 |
| 6,130,232 | A | 10/2000 | Mase et al. .............. 514/318 |
| 6,174,900 | B1 | 1/2001 | Okada et al. ............. 514/317 |

FOREIGN PATENT DOCUMENTS

| EP | 0 132 130 | 1/1985 |
| EP | 0 325 571 | 7/1989 |
| EP | 0 388 054 | 9/1990 |
| EP | 0 801 067 | 10/1997 |
| EP | 0 823 423 | 2/1998 |
| EP | 0 863 141 | 9/1998 |
| EP | 0 930 298 | 7/1999 |
| GB | 940540 | 10/1963 |
| JP | 92921/1994 | 4/1994 |
| JP | 135958/1994 | 5/1994 |
| WO | WO 91/09013 | 6/1991 |
| WO | WO 93/16018 | 8/1993 |
| WO | WO 93/16048 | 8/1993 |
| WO | WO 96/33973 | 10/1996 |
| WO | 97/36871 | * 9/1997 |
| WO | WO 97/45414 | 12/1997 |
| WO | WO 98/05641 | 2/1998 |
| WO | WO 98/29402 | 7/1998 |
| WO | WO 04/004629 | 1/2004 |
| WO | WO 04/005252 | 1/2004 |

OTHER PUBLICATIONS

Messaoik et al., International Journal of Pharmaceutics, "Comparative study and optimisation of the administration mode of three proton pump inhibitors by nasogastric tube", 2005, vol. 299, pp. 65-72.*
Chang-Young Lim et al., Journal of Clinical Microbiology, "Detection of Helicobacter pylori in Gastric Mucosa of patients with Gastroduodenal Diseases by PRC-Restriction Analysis using the RNA Polymerase Gene (rpoB)", 2003, vol. 41, pp. 3387-3391.*
Kubo et al., "Cloning, sequencing and expression of complementary DNA encoding the muscarinic acetylcholine receptor", *Nature*, 323(2):411-416 (1986).
Bonner et al., "Identification of a Family of Muscarinic Acetylcholine Receptor Genes", *Science*, 237:527-531 (1987).
Eglen et al., "Muscarinic receptor ligands and their theraputic potential", *Current Opinion in Chemical Biology*, 3:426-432 (1999).
Eglen et al., "Theraputic opportunities from muscarinic receptor research", *Trends in Pharmacological Sciences*, 22(8):409-414 (2001).
Felder et al., "Theraputic Opportunities for Muscarinic Receptors in the Central Nervous System", *Journal of Medicinal Chemistry*, 43(23):4333-4353 (2000).
Broadley and Kelly, "Muscarinic Receptor Agonists and Antagonists",*Molecules*, 6:142-193 (2001).
Birdsall et al., "Muscarinic receptors: it's a knockout", *Trends in Pharmacological Sciences*, 22(5):215-219 (2001).

(Continued)

*Primary Examiner*—D. Margaret Seaman
*Assistant Examiner*—Niloofar Rahmani
(74) *Attorney, Agent, or Firm*—Jayadeep R. Deshmukh, Esq.; George E. Heibel, Esq.

(57) ABSTRACT

This invention relates to derivatives of 3,6-disubstituted azabicyclo compounds. The compounds of this invention can function as muscarinic receptor antagonists, and can be used for the treatment of various diseases of the respiratory, urinary and gastrointestinal systems mediated through muscarinic receptors. The invention also relates to pharmaceutical compositions containing the compounds of the present invention and the methods for treating the diseases mediated through muscarinic receptors.

24 Claims, No Drawings

OTHER PUBLICATIONS de Groat and Yoshimura, "Pharmacology of the Lower Urinary Tract", *Annual Review of Pharmacology and Toxicology*, 41:691-721 (2001).

Steers, "The future direction of neuro-urology drug research", *Current Opinion in CPNS Investigational Drugs*, 2(3):268-282 (2000).

Chapple, "Muscarinic receptor antagonists in the treatment of overactive bladder", *Urology*, 55(Suppl. 5A):33-46 (2000).

Steers, Barrot, Wein, "Voiding dysfunction: diagnosis classification and management", In: *Adult and Pediatric Urology*, ed. Gillenwater, Grayhack, Howards, Duckett. Mosby, St. Louis, MO; 1220-1325, 3rd edition (1996).

Sagara et al., "Cyclohexylmethylpiperidinyltriphenylpropioamide: A Selective Muscarinic M3 Antagonist Discriminating against the Other Receptor Subtypes", *Journal of Medicinal Chemistry*, 45:984-987 (2002).

Vogel's textbook, "Practical Organic Chemistry" 1046-1047 (5th Ed.).

Braish et al., "Construction of the (1α,5α,6α)-6-Amino-3-azabicyclo[3.1.0]hexane Ring System", *Synlett*, 1100-1102 (1996).

Vogel's textbook, "Practical Organic Chemistry" 1048-1051 (5th Ed.).

Shacklett and Smith, "The Preparation of Substituted Benzilic Acids", *Journal of the American Chemical Society*, 75:2654-2657 (1953).

Gotteland et al., "(Aryloxy)methylsilane Derivatives as New Cholesterol Biosynthesis Inhibitors: Synthesis and Hypocholesterolemic Activity of a New Class of Squalene Epoxidase Inhibitors", *Journal of Medicinal Chemistry*, 38:3207-3216 (1995).

Weinstock et al., "A General, One-Step Synthesis of α-keto Esters", *Synthetic Communications*, 11(12):943-946 (1981).

Cornforth et al., "General Synthetic Routes to β-Hydroxy-acids from t-Butyl Esters and the Reformatskii Reaction", *Journal of the Chemical Society C*, 20:2799-2805 (1969).

Grover et al., "Chiral Mandelic Acid Template Provides a Highly Practical Solution for (S)-Oxybutynin Synthesis", *Journal of Organic Chemistry*, 65:6283-6287 (2000).

Moriya et al., "Affintity Profiles of Various Muscarinic Antagonists for Cloned Human Muscarinic Acetylcholine Receptor (mAchR) Subtypes and mAChRs in Rat Heart and Submandibular Gland", *Life Sciences*, 64(25):2351-2358 (1999).

Cheng and Prusoff, "Relationship between the inhibition constant ($K1$) and the concentration of inhibitor which causes 50 per cent inhibition ($I50$) of an enzymatic reaction", *Biochemical Pharmacology*, 22:3099-3108 (1973).

* cited by examiner

3,6-DISUBSTITUTED AZABICYCLO DERIVATIVES AS MUSCARINIC RECEPTOR ANTAGONISTS

FIELD OF THE INVENTION

This invention relates to the derivatives of 3,6-disubstituted azabicyclo compounds. The compounds of this invention can function as muscarinic receptor antagonists, and can be used for the treatment of various diseases of the respiratory, urinary and gastrointestinal systems mediated through muscarinic receptors.

The invention also relates to pharmaceutical compositions containing the compounds of the present invention and the methods of treating the diseases mediated through muscarinic receptors.

BACKGROUND OF THE INVENTION

Muscarinic receptors as members of the G Protein Coupled Receptors (GPCRs) are composed of a family of 5 receptor sub-types ($M_1$, $M_2$, $M_3$, $M_4$ and $M_5$) and are activated by the neurotransmitter acetylcholine. These receptors are widely distributed on multiple organs and tissues and are critical to the maintenance of central and peripheral cholinergic neurotransmission. The regional distribution of these receptor sub-types in the brain and other organs has been documented. For example, the $M_1$ subtype is located primarily in neuronal tissues such as cereberal cortex and autonomic ganglia, the $M_2$ subtype is present mainly in the heart where it mediates cholinergically induced bradycardia, and the $M_3$ subtype is located predominantly on smooth muscle and salivary glands (*Nature*, 1986; 323: 411; Science, 1987; 237: 527).

A review in *Current Opinions in Chemical Biology*, 1999; 3: 426, as well as in *Trends in Pharmacological Sciences*, 2001; 22: 409 by Eglen et. al., describe the biological potentials of modulating muscarinic receptor subtypes by ligands in different disease conditions like Alzheimer's disease, pain, urinary disease condition, chronic obstructive pulmonary disease etc.

A review in *J. Med. Chem.*, 2000; 43: 4333 by Christian C. Felder et. al. describes therapeutic opportunities for muscarinic receptors in the central nervous system and elaborates on muscarinic receptor structure and function, pharmacology and their therapeutic uses.

The pharmacological and medical aspects of the muscarinic class of acetylcholine agonists and antagonists are presented in a review in *Molecules*, 2001, 6: 142.

N. J. M. Birdsall et. al. in *Trends in Pharmacological Sciences*, 2001; 22: 215 have also summarized the recent developments on the role of different muscarinic receptor subtypes using different muscaranic receptors of knock out mice.

Muscarinic agonists such as muscarine and pilocarpine and antagonists such as atropine have been known for over a century, but little progress has been made in the discovery of receptor subtype-selective compounds making it difficult to assign specific functions to the individual receptors. Although classical muscarinic antagonists such as atropine are potent bronchodilators, their clinical utility is limited due to high incidence of both peripheral and central adverse effects such as tachycardia, blurred vision, dryness of mouth, constipation, dementia, etc. Subsequent development of the quarternary derivatives of atropine such as ipratropium bromide are better tolerated than parenterally administered options but most of them are not ideal anti-cholinergic bronchodilators due to lack of selectivity for muscarinic receptor sub-types. The existing compounds offer limited therapeutic benefit due to their lack of selectivity resulting in dose limiting side-effects such as thirst, nausea, mydriasis and those associated with the heart such as tachycardia mediated by the $M_2$ receptor.

*Annual Review of Pharmacological Toxicol.*, 2001; 41: 691, describes the pharmacology of the lower urinary tract infections. Although anti muscarinic agents such as oxybutynin and tolterodine that act non-selectively on muscarinic receptors have been used for many years to treat bladder hyperactivity, the clinical effectiveness of these agents has been limited due to the side effects such as dry mouth, blurred vision and constipation. Tolterodine is considered to be generally better tolerated than oxybutynin. (W. D. Steers et. al. in *Curr. Opin. Invest. Drugs*, 2: 268, C. R. Chapple et. al. in *Urology*, 55: 33), Steers W D, Barrot D M, Wein A J, 1996, Voiding dysfunction: diagnosis classification and management. In "Adult and Pediatric Urology," ed. J Y Gillenwatter, J T Grayhack, S S Howards, J W Duckett, pp 1220–1325, St. Louis, Mo.; Mosby. $3^{rd}$ edition.)

Despite these advances, there remains a need for development of new highly selective muscarinic antagonists which can interact with distinct subtypes, thus avoiding the occurrence of adverse effects.

Compounds having antagonistic activity against muscarinic receptors have been described in Japanese patent application Laid Open Number 92921/1994 and 135958/1994; WO 93/16048; U.S. Pat. No. 3,176,019; GB 940,540; EP 0325 571; WO 98/29402; EP 0801067; EP 0388054; WO 9109013; U.S. Pat. No. 5,281,601. U.S. Pat. Nos. 6,174,900, 6,130,232 and 5,948,792; WO 97/45414 are related to 1,4-disubstituted piperidine derivatives; WO 98/05641 describes fluorinated, 1,4-disubstitued piperidine derivatives; WO 93/16018 and WO96/33973 are other references.

A report in *J. Med. Chem.*, 2002; 44:984, describes cyclohexylmethyl piperidinyl triphenylpropioamide derivatives as selective $M_3$ antagonist discriminating against the other receptor subtypes.

SUMMARY OF THE INVENTION

The present invention provides derivatives of 3,6-disubstituted azabicyclo compounds as muscarinic receptor antagonists and are useful for the safe and effective therapeutic or prophylactic agents for the treatment of various diseases of the respiratory, urinary and gastrointestinal systems, and process for the synthesis of the novel compounds.

The invention also provides pharmaceutical compositions containing the compounds, and which may also contain acceptable carriers, excipients or diluents which are useful for the treatment of various diseases of the respiratory, urinary and gastrointestinal systems.

The present invention also includes within its scope prodrugs of the compounds. In general, such prodrugs are functionalized derivatives of these compounds which readily get converted in vivo into the defined compounds. Conventional procedures for the selection and preparation of suitable prodrugs are known to the artisan of ordinary skill in the art.

The invention also includes the enantiomers, diastereomers, N-oxides, polymorphs, pharmaceutically acceptable salts, pharmaceutically acceptable solvates, esters and metabolites of these compounds having the same type of activity.

The invention further includes pharmaceutical compositions comprising the compounds of the present invention, their prodrugs, metabolites, enantiomers, diastereomers, N-oxides, polymorphs, pharmaceutically acceptable salts, pharmaceutically acceptable solvates or esters, in combination with a pharmaceutically acceptably carrier and optionally included excipients.

Other advantages of the invention will be set forth in the description which follows and in part will be apparent from the description or may be learnt by the practice of the invention. The objects and the advantages of the invention may be realized and obtained by means of the mechanisms and combinations pointed out in the appended claims.

In accordance with one aspect of the present invention, there is provided a compound having the structure of Formula I:

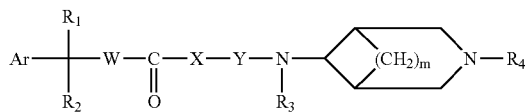

Formula I and its pharmaceutically acceptable salts, pharmaceutically acceptable solvates, esters, enantiomers, diastereomers, N-oxides, polymorphs, prodrugs, or metabolites, wherein:

Ar represents an aryl or a heteroaryl ring having 1–2 hetero atoms selected from the group consisting of oxygen, sulphur and nitrogen atoms, the aryl or heteroaryl rings may be unsubstituted or substituted by one to three substituents independently selected from straight or branched lower alkyl ($C_1$–$C_4$), trifluoromethyl, methylenedioxy, cyano, hydroxy, halogen (e.g. F, Cl, Br, I), nitro, lower alkoxy ($C_1$–$C_4$), aryloxy, amino or lower alkylamino;

$R_1$ represents $C_3$–$C_9$ cycloalkyl ring, a $C_3$–$C_9$ cyclo alkenyl ring, an aryl or a heteroaryl ring having 1 to 2 hetero atoms selected from the group consisting of oxygen, sulphur and nitrogen atoms, the aryl or a heteroaryl ring may be unsubstituted or substituted by one to three substituents independently selected from lower alkyl ($C_1$–$C_4$), trifluoromethyl, cyano, hydroxy, nitro, lower alkoxycarbonyl, halogen, lower alkoxy ($C_1$–$C_4$), unsubstituted amino or lower alkyl ($C_1$–$C_4$) amino;

$R_2$ represents a hydrogen, hydroxy, amino, alkoxy, alkenyloxy, alkynyloxy, carbamoyl or halogen (e.g. F, Cl, Br, I);

W represents $(CH_2)_p$, where p represents 0 to 1;

X represents an oxygen, sulphur, NR, or no atom, where R is H or lower alkyl ($C_1$–$C_4$);

Y represents $(CHR_5)q$ CO wherein $R_5$ represents hydrogen, or methyl; or Y represents $(CH_2)q$ wherein q represents 0 to 4;

m represents 0 to 2;

$R_3$ represents hydrogen, lower alkyl or $CO_2C(CH_3)_3$;

$R_4$ represents hydrogen, $C_1$–$C_{15}$ saturated or unsaturated aliphatic hydrocarbon groups in which any 1 to 6 hydrogen atoms may be substituted with the group independently selected from halogen, arylalkyl, arylalkenyl, heteroarylalkyl or heteroarylalkenyl having 1 to 2 hetero atoms selected from the group consisting of nitrogen, oxygen and sulphur atoms with an option that any 1 to 3 hydrogen atoms on an aryl or heteroaryl ring in said arylalkyl, arylalkenyl, hetero arylalkenyl group may be substituted with lower alkyl, trifluoromethyl, cyano, hydroxyl, carboxylic acid, nitro, lower alkoxycarbonyl, halogen, lower alkoxy, amino, lower alkylamino, lower-alkyl carbonyl amino, loweralkyl thiocarbonyl amino or loweralkyl carbonyl amino sulphonyl and pharmaceutically acceptable salts thereof.

More particular compounds of the present invention are represented by Formula II,

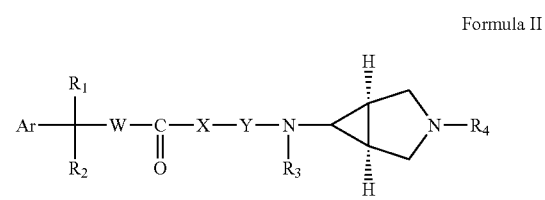

Formula II wherein Ar, $R_1$, $R_2$, $R_3$, $R_4$, W, X and Y are as defined for Formula I.

Further particular compounds are represented by Formula III

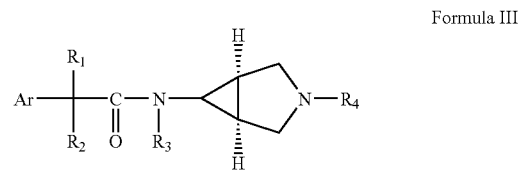

Formula III wherein Ar, $R_1$, $R_2$, $R_3$ and $R_4$ are as defined for Formula I.

Still more particular compounds are represented by Formula IV

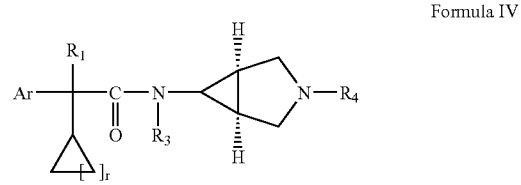

Formula IV wherein Ar, $R_1$, $R_3$ and $R_4$ are as defined for Formula I and r is 1 to 4.

Still more particular compounds are represented by Formula V

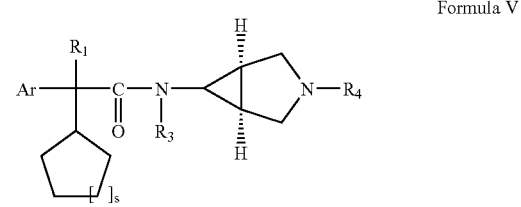

Formula V wherein Ar, $R_1$, $R_3$ and $R_4$ are as defined for Formula I and s is 1 to 3.

Another particular compound is represented by Formula VI,

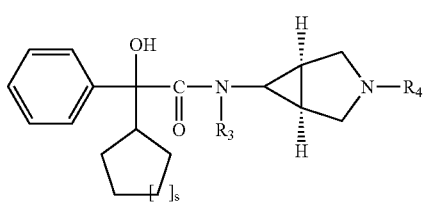

Formula VI wherein $R_3$, $R_4$ and s are as defined for Formula V.

DETAILED DESCRIPTION OF THE INVENTION

The compounds of the present invention may be prepared by the reaction sequence as shown in Scheme I

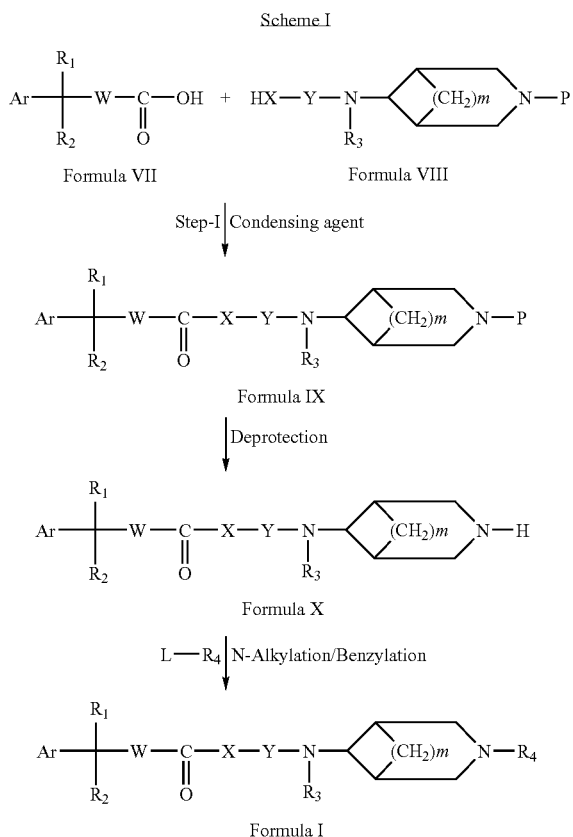

The preparation comprises condensing a compound of Formula VII with the compound of Formula VIII wherein
Ar represents an aryl or a heteroaryl ring having 1–2 hetero atoms selected from the group consisting of oxygen, sulphur and nitrogen atoms, the aryl or heteroaryl rings may be unsubstituted or substituted by one to three substituents independently selected from straight or branched lower alkyl ($C_1$–$C_4$), trifluoromethyl, methylenedioxy, cyano, hydroxy, halogen (e.g. F, Cl, Br, I), nitro, lower alkoxy ($C_1$–$C_4$), aryloxy, amino or lower alkylamino;

$R_1$ represents $C_3$–$C_9$ cycloalkyl ring, a $C_3$–$C_9$ cyclo alkenyl ring, an aryl or a heteroaryl ring having 1 to 2 hetero atoms selected from the group consisting of oxygen, sulphur and nitrogen atoms, the aryl or a heteroaryl ring may be unsubstituted or substituted by one to three substituents independently selected from lower alkyl ($C_1$–$C_4$), trifluoromethyl, cyano, hydroxy, nitro, lower alkoxycarbonyl, halogen, lower alkoxy ($C_1$–$C_4$), unsubstituted amino or lower alkyl ($C_1$–$C_4$) amino;

$R_2$ represents a hydrogen, hydroxy, amino, alkoxy, alkenyloxy, alkynyloxy, carbamoyl or halogen (e.g. F, Cl, Br, I);

W represents $(CH_2)_p$, where p represents 0 to 1;

X represents an oxygen, sulphur, NR, or no atom, where R is H or lower alkyl ($C_1$–$C_4$);

Y represents $(CHR_5)q$ CO wherein $R_5$ represents hydrogen, or methyl; or Y represents $(CH_2)q$ wherein q represents 0 to 4;

m represents 0 to 2;

$R_3$ represents hydrogen, lower alkyl or $CO_2C(CH_3)_3$;

P is any group which can be used to protect an amino group, for example benzyl and t-butyloxycarbonyl, in the presence of a condensing agent, for example 1-(3-dimethyl amino propyl)-3-ethyl carbodiimide hydrochloride (EDC) or 1,8-diazabicyclo [5.4.0]undec-7-ene (DBU), to give a protected compound of Formula IX wherein $R_1$, $R_2$, $R_3$, W, X, Y, P and m are the same as defined earlier. The compound of Formula IX on deprotection through reaction with a deprotecting agent, for example palladium on carbon, trifluoroacetic acid (TFA) and hydrochloric acid, in an organic solvent gives an unprotected compound of Formula X wherein $R_1$, $R_2$, $R_3$, W, X, Y and m are the same as defined earlier. Compounds according to Formula X (with $R_4$ as hydrogen) are useful as muscarinic receptor antagonists, and are useful as safe and effective therapeutic or prophylactic agents for the treatment of various diseases of the respiratory, urinary and gastrointestinal systems. These compounds can be formulated as pharmaceutical compositions for the treatment of various diseases of the respiratory, urinary and gastrointestinal systems. Compounds of Formula X can be optionally N-alkylated or benzylated with a suitable alkylating or benzylating agent L-$R_4$ to give a compound of Formula I, wherein L is any leaving group, for example halogen, O-mestyl or O-tosyl group, and $R_4$ represents hydrogen, $C_1$–$C_{15}$ saturated or unsaturated aliphatic hydrocarbon groups in which any 1 to 6 hydrogen atoms may be substituted with the group independently selected from halogen, arylalkyl, arylalkenyl, heteroarylalkyl or heteroarylalkenyl having 1 to 2 hetero atoms selected from the group consisting of nitrogen, oxygen and sulphur atoms with an option that any 1 to 3 hydrogen atoms on an aryl or heteroaryl ring in said arylalkyl, arylalkenyl, hetero arylalkenyl group may be substituted with lower alkyl, trifluoromethyl, cyano, hydroxyl, carboxylic acid, nitro, lower alkoxycarbonyl, halogen, lower alkoxy, amino, lower alkylamino, lower-alkyl carbonyl amino, loweralkyl thiocarbonyl amino or loweralkyl carbonyl amino sulphonyl and pharmaceutically acceptable salts thereof.

In the above scheme, where specific bases, condensing agents, protecting groups, deprotecting agents, N-alkylating/benzylating agents, solvents, catalysts etc. are mentioned, it is to be understood that other bases, condensing agents, protecting groups, deprotecting agents, N-alkylating/benzylating agents, solvents, catalysts etc. known to those skilled in the art may be used. Similarly, the reaction temperature and duration may be adjusted according to the desired needs.

An illustrative list of particular compounds according to the invention and capable of being produced by Scheme I include:

Compound No. Chemical Name
1. (1α,5α,6α)-6-N-(3-azabicyclo[3.1.0]hexyl-3-benzyl)-2-hydroxy-2,2-diphenyl acetamide,
2. (1α,5α,6α)-6-N-(3-azabicyclo[3.1.0]hexyl-3-benzyl)-2-hydroxy-2,2-di(4-fluoro phenyl)acetamide,
3. (1α,5α,6α)-6-N-(3-azabicyclo[3.1.0]hexyl-3-benzyl)-2-(2-propenyloxy)-2,2-diphenyl acetamide,
4. (1α,5α,6α)-6-N-(3-azabicyclo[3.1.0]hexyl-3-benzyl)-2-(2-propenyloxy)-2,2-di(4-fluorophenyl)acetamide,
5. (1α,5α,6α)-6-N-(3-azabicyclo[3.1.0]hexyl-3-benzyl)-2-propyloxy-2,2-diphenyl acetamide,
6. (1α,5α,6α)-6-N-(3-azabicyclo[3.1.0]hexyl-3-benzyl)-2-propyloxy-2,2-di(4-fluoro phenyl)acetamide,
7. (1α,5α,6α)-6-N-(3-azabicyclo[3.1.0]hexyl-3-benzyl)-2-(2-propynyloxy)-2,2-diphenyl acetamide,
8. (1α,5α,6α)-6-N-(3-azabicyclo[3.1.0]hexyl-3-benzyl)-2-hydroxy-2,2-di(2-furyl)acetamide,
9. (1α,5α,6α)-6-N-(3-azabicyclo[3.1.0]hexyl-3-benzyl)-2-hydroxy-2,2-di(2-thienyl)acetamide,
10. (1α,5α,6α)-4-(6-N-(3-azabicyclo[3.1.0]hexyl-3-benzyl))-N-tert-butyloxycarbonyl) propyl-1-(2-hydroxy-2,2-diphenyl)acetate,
11. (1α,5α,6α)-3-(6-N-(3-azabicyclo[3.1.0]hexyl-3-benzyl))-N-tert-butyloxycarbonyl)propyl-1-(2-hydroxy-2,2-diphenyl)acetate,
12. (1α,5α,6α)-3-(6-N-(3-azabicyclo[3.1.0]hexyl-3-benzyl))-N-tert-butyloxycarbonyl)propyl-1-(2-propyloxy-2,2-diphenyl)acetate,
13. (1α,5α,6α)-4-(6-N-(3-azabicyclo[3.1.0]hexyl-3-benzyl))-N-tert-butyl oxy carbonyl)butyl-1-(2-propyloxy-2,2-diphenyl)acetate,
14. (1α,5α,6α)-4-(6-N-(3-azabicyclo[3.1.0]hexyl-3-benzyl))-N-tert-butyl oxy carbonyl)butyl-1-(2-(2-propenyloxy)-2,2-diphenyl)acetate,
15. (1α,5α,6α)-4-(6-N-(3-azabicyclo[3.1.0]hexyl-3-benzyl))-N-tert-butyl oxy carbonyl)butyl-1-(2-hydroxy-2,2-di(4-fluorophenyl))acetate,
16. (1α,5α,6α)-4-(6-N-(3-azabicyclo[3.1.0]hexyl-3-benzyl))-N-tert-butyl oxy carbonyl)butyl-1-(2-propyloxy-2,2-di(4-fluorophenyl))acetate,
17. (1α,5α,6α)-1-(6-N-(3-azabicyclo[3.1.0]hexyl-3-benzyl))-N-acetamido-2-(2-propyloxy)-2,2-diphenyl acetate,
18. (1α,5α,6α)-1-(6-N-(3-azabicyclo[3.1.0]hexyl-3-benzyl))-N-acetamido-2-(2-propenyloxy)-2,2-diphenyl acetate,
19. (1α,5α,6α)-1-(6-N-(3-azabicyclo[3.1.0]hexyl-3-benzyl))-N-propionamido-2-(2-propenyloxy)-2,2-diphenyl acetate,
20. (1α,5α,6α)-1-(6-N-(3-azabicyclo[3.1.0]hexyl-3-benzyl))-N-propionamido-2-2-propyloxy)-2,2-diphenyl acetate,
21. (1α,5α,6α)-1-(6-N-(3-azabicyclo[3.1.0]hexyl-3-benzyl))-N-acetamido-2-hydroxy-2,2-di(4-fluorophenyl)acetate,
22. (1α,5α,6α)-6-N-(3-azabicyclo[3.1.0]hexyl-3-benzyl)-2-cyclohexyl-2-hydroxy-2-phenyl acetamide,
23. (1α,5α,6α)-6-N-(3-azabicyclo[3.1.0]hexyl-3-(3,5-difluorobenzyl))-2-cyclo hexyl-2-hydroxy-2-phenyl acetamide,
24. (1α,5α,6α)-6-N-(3-azabicyclo[3.1.0]hexyl-3-(4-bromobenzyl))-2-cyclo hexyl-2-hydroxy-2-phenyl acetamide,
25. (1α,5α,6α)-6-N-(3-azabicyclo[3.1.0]hexyl-3-(2,6-difluorobenzyl))-2-cyclo hexyl-2-hydroxy-2-phenyl acetamide,
26. (1α,5α,6α)-6-N-(3-azabicyclo[3.1.0]hexyl-3-(2-phenylbenzyl))-2-cyclohexyl-2-hydroxy-2-phenyl acetamide,
27. (1α,5α,6α)-6-N-(3-azabicyclo[3.1.0]hexyl-3-(2-phenylethyl))-2-cyclohexyl-2-hydroxy-2-phenyl acetamide,
28. (1α,5α,6α)-6-N-(3-azabicyclo[3.1.0]hexyl-3-(2-(2,3-dihydrobenzo furan-5-yl)ethyl))-2-cyclohexyl-2-hydroxy-2-phenyl acetamide,
29. (1α,5α,6α)-6-N-(3-azabicyclo[3.1.0]hexyl-3-(2-(3,4-methylene dioxyphenyl)ethyl))-2-cyclohexyl-2-hydroxy-2-phenyl acetamide,
30. (1α,5α,6α)-6-N-(3-azabicyclo[3.1.0]hexyl-3-(1-(2,3-dihydrobenzo furan-5-yl)acetyl))-2-cyclohexyl-2-hydroxy-2-phenyl acetamide,
31. (1α,5α,6α)-6-N-(3-azabicyclo[3.1.0]hexyl-3-(2-(benzofuran-5-yl)ethyl))-2-cyclo hexyl-2-hydroxy-2-phenyl acetamide,
32. (1α,5α,6α)-6-N-(3-azabicyclo[3.1.0]hexyl-3-methyl)-2-cyclohexyl-2-hydroxy-2-phenyl acetamide,
33. (1α,5α,6α)-6-N-(3-azabicyclo[3.1.0]hexyl-3-ethyl)-2-cyclohexyl-2-hydroxy-2-phenyl acetamide,
34. (1α,5α,6α)-6-N-(3-azabicyclo[3.1.0]hexyl-3-(1-propyl))-2-cyclohexyl-2-hydroxy-2-phenyl acetamide,
35. (1α,5α,6α)-6-N-(3-azabicyclo[3.1.0]hexyl-3-(2-propargyl))-2-cyclohexyl-2-hydroxy-2-phenyl acetamide,
36. (1α,5α,6α)-6-N-(3-azabicyclo[3.1.0]hexyl-3-(2-propenyl))-2-cyclohexyl-2-hydroxy-2-phenyl acetamide,
37. (1α,5α,6α)-6-N-(3-azabicyclo[3.1.0]hexyl-3-(2-propyl))-2-cyclohexyl-2-hydroxy-2-phenyl acetamide,
38. (1α,5α,6α)-6-N-(3-azabicyclo[3.1.0]hexyl-3-cyclopropyl)-2-cyclohexyl-2-hydroxy-2-phenyl acetamide,
39. (1α,5α,6α)-6-N-(3-azabicyclo[3.1.0]hexyl-3-(1-butyl))-2-cyclohexyl-2-hydroxy-2-phenyl acetamide,
40. (1α,5α,6α)-6-N-(3-azabicyclo[3.1.0]hexyl-3-(3-methyl-2-butenyl))-2-cyclo hexyl-2-hydroxy-2-phenyl acetamide,
41. (1α,5α,6α)-6-N-(3-azabicyclo[3.1.0]hexyl-3-(4-methyl-3-pentenyl))-2-cyclohexyl-2-hydroxy-2-phenyl acetamide,
42. (1α,5α,6α)-6-N-(3-azabicyclo[3.1.0]hexyl-3-(3,4-methylenedioxy benzyl))-2-cyclohexyl-2-hydroxy-2-phenyl acetamide,
43. (1α,5α,6α)-6-N-(3-azabicyclo[3.1.0]hexyl-3-(6,6-dimethyl-2,4-heptadiynyl))-2-cyclohexyl-2-hydroxy-2-phenyl acetamide,
44. (1α,5α,6α)-6-N-(3-azabicyclo[3.1.0]hexyl-3-benzoyl)-2-cyclohexyl-2-hydroxy-2-phenyl acetamide,
45. (1α,5α,6α)-6-N-(3-azabicyclo[3.1.0]hexyl-3-(2-formylfur-5-yl))-2-cyclohexyl-2-hydroxy-2-phenyl acetamide,
46. (1α,5α,6α)-6-N-(3-azabicyclo[3.1.0]hexyl-3-(aniline) thiourea)-2-cyclohexyl-2-hydroxy-2-phenyl acetamide,
47. (1α,5α,6α)-6-N-(3-azabicyclo[3.1.0]hexyl-3-(methyl, 4-amino-1-phenyl acetate)urea)-2-cyclohexyl-2-hydroxy-2-phenyl acetamide,
48. (1α,5α,6α)-6-N-(3-azabicyclo[3.1.0]hexyl-3-(4-amino-1-phenyl acetic acid) urea)-2-cyclohexyl-2-hydroxy-2-phenyl acetamide,
49. (1α,5α,6α)-6-N-(3-azabicyclo[3.1.0]hexyl-3-(4-methylphenyl-1-sulphonamide)urea)-2-cyclohexyl-2-hydroxy-2-phenyl acetamide,
50. (1α,5α,6α)-6-N-(3-azabicyclo[3.1.0]hexyl-3-benzyl)-2-cyclohexyl-2-hydroxy-2-(4-methylphenyl)acetamide,
51. (1α,5α,6α)-6-N-(3-azabicyclo[3.1.0]hexyl-3-benzyl)-2-cyclohexyl-2-hydroxy-2-(4-methoxyphenyl)acetamide, 52. (1α,5α,6α)-6-N-(3-azabicyclo[3.1.0]hexyl-3-benzyl)-2-cyclohexyl-2-hydroxy-2-(4-phenoxyphenyl)acetamide, 53. (1α,5α,6α)-6-N-(3-azabicyclo[3.1.0]hexyl-3-benzyl)-2-cyclohexyl-2-hydroxy-2-(4-fluorophenyl)acetamide, 54. (1α,5α,6α)-6-N-(3-azabicyclo[3.1.0]hexyl-3-benzyl)-2-cyclohexyl-2-hydroxy-2-(3,4-methylenedioxyphenyl)acetamide, 55. (1α,5α,6α)-6-N-(3-azabicyclo[3.1.0]hexyl-3-benzyl)-2-cyclohexyl-2-hydroxy-2-(4-tertbutylphenyl)acetamide, 56. (1α,5α,6α)-6-N-(3-azabicyclo[3.1.0]hexyl-3-(4-methyl-3-pentenyl))-2-cyclohexyl-2-hydroxy-2-(4-methylphenyl)acetamide, 57. (1α,5α,6α)-6-N-(3-azabicyclo[3.1.0]hexyl-3-(4-methyl-3-pentenyl))-2-cyclohexyl-2-hydroxy-2-(4-methoxyphenyl)acetamide, 58. (1α,5α,6α)-6-N-(3-azabicyclo[3.1.0]hexyl-3-(4-methyl-3-pentenyl))-2-cyclohexyl-2-hydroxy-2-(4-fluorophenyl)acetamide, 59. (1α,5α,6α)-6-N-(3-azabicyclo[3.1.0]hexyl-3-benzyl)-2-cyclohexyl-2-methoxy-2-phenyl acetamide, 60. (1α,5α,6α)-6-N-(3-azabicyclo[3.1.0]hexyl-3-ethyl)-2-cyclohexyl-2-methoxy -2-phenyl acetamide, 61. (1α,5α,6α)-6-N-(3-azabicyclo[3.1.0]hexyl-3-benzyl)-2-cyclohexyl-2-(2-propenyloxy)-2-phenyl acetamide, 62. (1α,5α,6α)-6-N-(3-azabicyclo[3.1.0]hexyl-3-(4-methyl-3-pentenyl))-2-cyclohexyl-2-methoxy-2-phenyl acetamide, 63. (1α,5α,6α)-6-N-(3-azabicyclo[3.1.0]hexyl-3-(2,4-difluorobenzyl))-2-cyclohexyl-2-methoxy-2-phenyl acetamide, 64. (1α,5α,6α)-6-N-(3-azabicyclo[3.1.0]hexyl-3-benzyl)-2-cyclopentyl-2-hydroxy-2-phenyl acetamide, 65. (1α,5α,6α)-6-N-(3-azabicyclo[3.1.0]hexyl-3-(4-methyl-3-pentenyl))-2-cyclo pentyl-2-hydroxy-2-phenyl acetamide, 66. (1α,5α,6α)-6-N-(3-azabicyclo[3.1.0]hexyl-3-(2-(3,4-methylenedioxy phenyl)ethyl)-2-cyclopentyl-2-hydroxy-2-phenyl acetamide, 67. (1α,5α,6α)-6-N-(3-azabicyclo[3.1.0]hexyl-3-(2-phenylethyl))-2-cyclopentyl -2-hydroxy-2-phenyl acetamide, 68. (1α,5α,6α)-6-N-(3-azabicyclo[3.1.0]hexyl-3-(2-(2,3-dihydrobenzofuran-5-yl)ethyl))-2-cyclopentyl-2-hydroxy-2-phenyl acetamide, 69. (1α,5α,6α)-6-N-(3-azabicyclo[3.1.0]hexyl-3-(2-methylpyrid-6-yl)-2-cyclo pentyl-2-hydroxy-2-phenyl acetamide, 70. (1α,5α,6α)-6-N-(3-azabicyclo[3.1.0]hexyl-3-(1-(2,3-dihydrobenzofuran-5-yl)acetyl))-2-cyclopentyl-2-hydroxy-2-phenyl acetamide, 71. (1α,5α,6α)-6-N-(3-azabicyclo[3.1.0]hexyl-3-(2-(benzofuran-5-yl)ethyl))-2-cyclopentyl-2-hydroxy-2-phenyl acetamide, 72. (1α,5α,6α)-6-N-(3-azabicyclo[3.1.0]hexyl-3-benzyl)-2-cycloheptyl-2-hydroxy-2-phenyl acetamide, 73. (1α,5α,6α)-6-N-(3-azabicyclo[3.1.0]hexyl-3-(4-methyl-3-pentenyl))-2-cycloheptyl-2-hydroxy-2-phenyl acetamide, 74. 2-Amino-((1α,5α,6α)-6-N-(3-azabicyclo[3.1.0]hexyl-3-benzyl) propionamido)-2-cyclohexyl-2-hydroxy-2-phenyl acetamide, 75. 2-Amino-((1α,5α,6α)-6-N-(3-azabicyclo[3.1.0]hexyl-3-benzyl)acetamido)-2-cyclohexyl-2-hydroxy-2-phenyl acetamide, 76. 3-Amino-((1α,5α,6α)-6-N-(3-azabicyclo[3.1.0]hexyl-3-benzyl) propionamido)-2-cyclohexyl-2-hydroxy-2-phenyl acetamide, 77. (1α,5α,6α)-6-N-(3-azabicyclo[3.1.0]hexyl-3-benzyl)-3-cyclohexyl-3-hydroxy-3-phenyl propionamide, 78. 2-Amino-((1α,5α,6α)-6-N-(3-azabicyclo[3.1.0]hexyl-3-benzyl)acetamido)-3-cyclohexyl-3-hydroxy-3-phenyl propionamide, 79. 2-Amino-((1α,5α,6α)-6-N-(3-azabicyclo[3.1.0]hexyl-3-benzyl) propionamido)-2-cyclohexyl-3-hydroxy-3-phenyl propionamide, 80. (1α,5α,6α)-2-[6-N-(3-azabicyclo[3.1.0]hexyl-3-benzyl-)-N-propionamido-2-cyclohexyl-2-hydroxy-2-phenyl acetate, 81. (2R)(1α,5α,6α)-6-N-(3-azabicyclo[3.1.0]hexyl-3-(4-methyl-3-pentenyl) -2-cyclopentyl-2-hydroxy-2-phenyl acetamide, 82. (2R)(1α,5α,6α)-6-N-(3-azabicyclo[3.1.0]hexyl-3-(3,4-methylene dioxyphenyl)ethyl)-2-cyclopentyl-2-hydroxy-2-phenyl acetamide, or a pharmaceutically acceptable salts thereof.

The following salts of particular compounds were prepared:

83. (2R)-(1α,5α,6α)-6-N-(3-azabicyclo[3.1.0]hexyl-3-(4-methyl-3-pentenyl))-2-cyclopentyl-2-hydroxy-2-phenyl acetamide succinate salt, 84. (2R)-(1α,5α,6α)-6-N-(3-azabicyclo[3.1.0]hexyl-3-(4-methyl-3-pentenyl))-2-cyclopentyl-2-hydroxy-2-phenyl acetamide L-(+)-tartrate salt, 85. (1α,5α,6α)-6-N-(3-azabicyclo[3.1.0]hexyl)-2-cyclohexyl-2-hydroxy-2-phenyl acetamide, 86. (1α,5α,6α)-6-N-(3-azabicyclo[3.1.0]hexyl)-2-cyclohexyl-2-hydroxy-2-(4-fluorophenyl)acetamide, 87. (1α,5α,6α)-6-N-(3-azabicyclo[3.1.0]hexyl)-2-cyclohexyl-2-hydroxy-2-(4-methoxyphenyl)acetamide, 88. (1α,5α,6α)-6-N-(3-azabicyclo[3.1.0]hexyl)-2-cyclohexyl-2-hydroxy-2-(4-methylphenyl)acetamide, 89. (1α,5α,6α)-6-N-(3-azabicyclo[3.1.0]hexyl)-2-cyclopentyl-2-hydroxy-2-phenyl acetamide, 90. (1α,5α,6α)-6-N-(3-azabicyclo[3.1.0]hexyl)-2-cycloheptyl-2-hydroxy-2-phenyl acetamide, 91. (1α,5α,6α)-6-N-(3-azabicyclo[3.1.0]hexyl)-2-cyclobutyl-2-hydroxy-2-phenyl acetamide, 92. (1α,5α,6α)-6-N-(3-azabicyclo[3.1.0]hexyl)-2-cyclopropyl-2-hydroxy-2-phenyl acetamide, 93. (1α,5α,6α)-1-[6N-(3-azabicyclo[3.1.0]hexyl)]-N-acetamido-2-hydroxy-2-cyclohexyl-2-phenylacetate, 94. (1α,5α,6α)-1-[6N-(3-azabicyclo[3.1.0]hexyl)]-N-propionamido-2-hydroxy-2-cyclohexyl-2-phenylacetate, 95. (1α,5α,6α)-4-[6N-(3-azabicyclo[3.1.0]hexyl)]-N-(tert-butyloxy carbonyl)butyl-1-[2-hydroxy-2,2-bis(4-fluorophenyl)]acetate, 96. (1α,5α,6α)-4-[6N-(3-azabicyclo[3.1.0]hexyl)]-N-(tert-butyloxy carbonyl)butyl-1-[2-propyloxy-2,2-bis(4-fluorophenyl)]acetate, 97. (1α,5α,6α)-6N-(3-azabicyclo[3.1.0]hexyl)-2,2-diphenyl acetamide, 98. (1α,5α,6α)-6N-(3-azabicyclo[3.1.0]hexyl)-2-cyclohexyl-2-methoxy-2-phenylacetamide The illustrated list of some particular compounds represented by Formula I is also given in Table I.

TABLE I

FORMULA I

Ar—C(R₁)(R₂)—W—C(=O)—X—Y—N(R₃)—[bicyclic (CH₂)ₘ N—R₄]

(m = 0)

| Com No. | Ar | R₁ | R₂ | W | X | Y | R₃ | R₄ |
|---|---|---|---|---|---|---|---|---|
| 1. | phenyl | phenyl | OH | — | — | — | H | benzyl |
| 2. | 4-F-phenyl | 4-F-phenyl | OH | — | — | — | H | benzyl |
| 3. | phenyl | phenyl | O-allyl | — | — | — | H | benzyl |
| 4. | 4-F-phenyl | 4-F-phenyl | O-allyl | — | — | — | H | benzyl |
| 5. | phenyl | phenyl | O-propyl | — | — | — | H | benzyl |
| 6. | 4-F-phenyl | 4-F-phenyl | O-propyl | — | — | — | H | benzyl |
| 7. | phenyl | phenyl | O-propargyl | — | — | — | H | benzyl |
| 8. | 2-furyl | 2-furyl | OH | — | — | — | H | benzyl |
| 9. | 2-thienyl | 2-thienyl | OH | — | — | — | H | benzyl |
| 10. | phenyl | phenyl | OH | — | O | $(CH_2)_4$ | $CO_2Butyl^t$ | benzyl |
| 11. | phenyl | phenyl | OH | — | O | $(CH_2)_3$ | $CO_2Butyl^t$ | benzyl |
| 12. | phenyl | phenyl | O-propyl | — | O | $(CH_2)_3$ | $CO_2Butyl^t$ | benzyl |

TABLE I-continued

FORMULA I

Ar—C(R₁)(R₂)—W—C(=O)—X—Y—N(R₃)—[cyclic (CH₂)ₘ N—R₄]

(m = 0)

| Com No. | Ar | R₁ | R₂ | W | X | Y | R₃ | R₄ |
|---|---|---|---|---|---|---|---|---|
| 13. | phenyl | phenyl | O-propyl | — | O | $(CH_2)_4$ | $CO_2Butyl^t$ | phenethyl |
| 14. | phenyl | phenyl | O-allyl | — | O | $(CH_2)_4$ | $CO_2Butyl^t$ | phenethyl |
| 15. | 4-F-phenyl | 4-F-phenyl | OH | — | O | $(CH_2)_4$ | $CO_2Butyl^t$ | phenethyl |
| 16. | 4-F-phenyl | 4-F-phenyl | O-propyl | — | O | $(CH_2)_4$ | $CO_2Butyl^t$ | phenethyl |
| 17. | phenyl | phenyl | O-propyl | — | O | $CH_2CO$ | H | phenethyl |
| 18. | phenyl | phenyl | O-allyl | — | O | $CH_2CO$ | H | phenethyl |
| 19. | phenyl | phenyl | O-allyl | — | O | $(CH_2)_2CO$ | H | phenethyl |
| 20. | phenyl | phenyl | O-propyl | — | O | $(CH_2)_2CO$ | H | phenethyl |
| 21. | 4-F-phenyl | 4-F-phenyl | OH | — | O | $CH_2CO$ | H | phenethyl |
| 22. | cyclohexyl | phenyl | OH | — | — | — | H | phenethyl |
| 23. | phenyl | cyclohexyl | OH | — | — | — | H | 3,5-diF-phenethyl |

TABLE I-continued
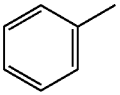
FORMULA I
(m = 0)
| Com No. | Ar | R₁ | R₂ | W | X | Y | R₃ | R₄ |
|---|---|---|---|---|---|---|---|---|
| 24. | 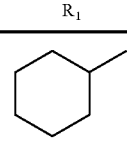 | 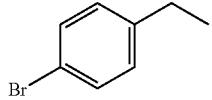 | OH | — | — | — | H | 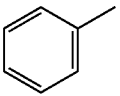 |
| 25. | 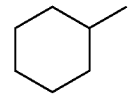 |  | OH | — | — | — | H | 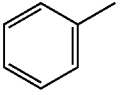 |
| 26. | 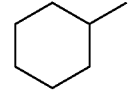 | 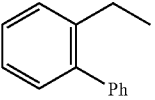 | OH | — | — | — | H | 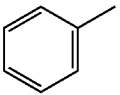 |
| 27. | 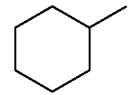 | 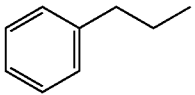 | OH | — | — | — | H | 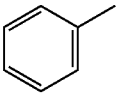 |
| 28. | 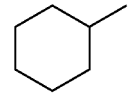 | 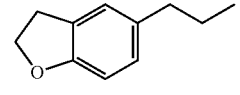 | OH | — | — | — | H | 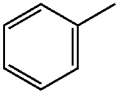 |
| 29. | 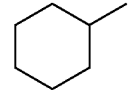 | 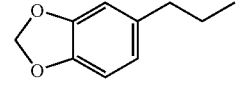 | OH | — | — | — | H | 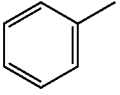 |
| 30. | 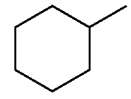 | 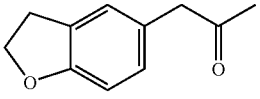 | OH | — | — | — | H | 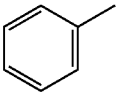 |
| 31. | 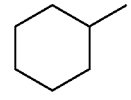 | 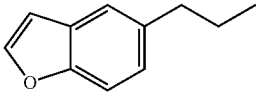 | OH | — | — | — | H | 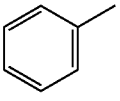 |
| 32. | 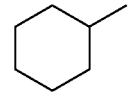 | 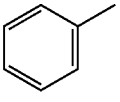 | OH | — | — | — | H | Methyl |
| 33. | 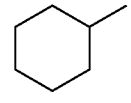 | 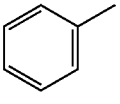 | OH | — | — | — | H | Ethyl |
| 34. | 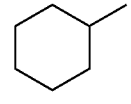 | | OH | — | — | — | H | 1-Propyl |

TABLE I-continued

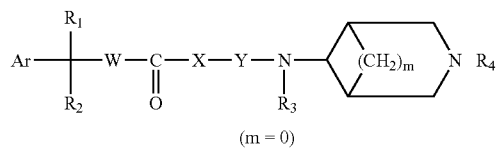

FORMULA I (m = 0)

| Com No. | Ar | R₁ | R₂ | W | X | Y | R₃ | R₄ |
|---|---|---|---|---|---|---|---|---|
| 35. | cyclohexyl | phenyl | OH | — | — | — | H | 2-Propargyl |
| 36. | cyclohexyl | phenyl | OH | — | — | — | H | 2-Propenyl |
| 37. | phenyl | cyclohexyl | OH | — | — | — | H | 2-Propyl |
| 38. | phenyl | cyclohexyl | OH | — | — | — | H | Cyclopropyl |
| 39. | phenyl | cyclohexyl | OH | — | — | — | H | 1-Butyl |
| 40. | phenyl | cyclohexyl | OH | — | — | — | H | (2-methyl-2-butenyl) |
| 41. | phenyl | cyclohexyl | OH | — | — | — | H | (2-methyl-2-pentenyl) |
| 42. | phenyl | cyclohexyl | OH | — | — | — | H | (benzodioxole-ethyl) |
| 43. | phenyl | cyclohexyl | OH | — | — | — | H | (t-butyl-diyne) |
| 44. | phenyl | cyclohexyl | OH | — | — | — | H | (phenacyl) |
| 45. | phenyl | cyclohexyl | OH | — | — | — | H | (5-ethyl-furan-2-carbaldehyde) |

TABLE I-continued

FORMULA I

Ar−C(R$_1$)(R$_2$)−W−C(=O)−X−Y−N(R$_3$)−(CH$_2$)$_m$−N−R$_4$ (m = 0)

| Com No. | Ar | R$_1$ | R$_2$ | W | X | Y | R$_3$ | R$_4$ |
|---|---|---|---|---|---|---|---|---|
| 46. | phenyl | cyclohexyl | | OH | — | — | — | H | N-phenyl thioamide (PhNH-C(=S)-) |
| 47. | phenyl | cyclohexyl | | OH | — | — | — | H | 4-(MeO$_2$C)-C$_6$H$_4$-NH-C(=O)- |
| 48. | phenyl | cyclohexyl | | OH | — | — | — | H | 4-(HO$_2$C)-C$_6$H$_4$-NH-C(=O)- |
| 49. | phenyl | cyclohexyl | | OH | — | — | — | H | 4-Me-C$_6$H$_4$-SO$_2$-NH-C(=O)- |
| 50. | 4-Me-C$_6$H$_4$- | cyclohexyl | | OH | — | — | — | H | PhCH$_2$CH$_2$- |
| 51. | 4-MeO-C$_6$H$_4$- | cyclohexyl | | OH | — | — | — | H | PhCH$_2$CH$_2$- |
| 52. | 4-PhO-C$_6$H$_4$- | cyclohexyl | | OH | — | — | — | H | PhCH$_2$CH$_2$- |
| 53. | 4-F-C$_6$H$_4$- | cyclohexyl | | OH | — | — | — | H | PhCH$_2$CH$_2$- |
| 54. | 3,4-methylenedioxyphenyl | cyclohexyl | | OH | — | — | — | H | PhCH$_2$CH$_2$- |
| 55. | 4-tBu-C$_6$H$_4$- | cyclohexyl | | OH | — | — | — | H | PhCH$_2$CH$_2$- |

TABLE I-continued

FORMULA I

Ar—C(R1)(R2)—W—C(=O)—X—Y—N(R3)—[(CH2)m]—N—R4

(m = 0)

| Com No. | Ar | R1 | R2 | W | X | Y | R3 | R4 |
|---|---|---|---|---|---|---|---|---|
| 56. | 4-Me-C6H4 | cyclohexyl | OH | — | — | — | H | CH2CH=C(Me)CH2CH3 |
| 57. | 4-MeO-C6H4 | cyclohexyl | OH | — | — | — | H | CH2CH=C(Me)CH2CH3 |
| 58. | 4-F-C6H4 | cyclohexyl | OH | — | — | — | H | CH2CH=C(Me)CH2CH3 |
| 59. | Ph | cyclohexyl | OMe | — | — | — | H | CH2CH2-Ph |
| 60. | Ph | cyclohexyl | OMe | — | — | — | H | Ethyl |
| 61. | Ph | cyclohexyl-O-CH2-CH=CH2 | | — | — | — | H | CH2CH2-Ph |
| 62. | Ph | cyclohexyl | OMe | — | — | — | H | CH2CH=C(Me)CH2CH3 |
| 63. | Ph | cyclohexyl | OMe | — | — | — | H | 2,4-F2-C6H3-CH2CH2 |
| 64. | Ph | cyclopentyl | OH | — | — | — | H | CH2CH2-Ph |
| 65. | Ph | cyclopentyl | OH | — | — | — | H | CH2CH=C(Me)CH2CH3 |
| 66. | Ph | cyclopentyl | OH | — | — | — | H | 3,4-methylenedioxyphenyl-CH2CH2CH2 |
| 67. | Ph | cyclopentyl | OH | — | — | — | H | CH2CH2CH2-Ph |

TABLE I-continued

FORMULA I

Ar—C(R₁)(R₂)—W—C(=O)—X—Y—N(R₃)—(CH₂)ₘ—N—R₄

(m = 0)

| Com No. | Ar | R₁ | R₂ | W | X | Y | R₃ | R₄ |
|---|---|---|---|---|---|---|---|---|
| 68. | phenyl | cyclopentyl | | OH | — | — | H | 2,3-dihydrobenzofuran-5-yl propyl |
| 69. | phenyl | cyclopentyl | | OH | — | — | H | 2-ethyl-6-methylpyridinyl |
| 70. | phenyl | cyclopentyl | | OH | — | — | H | 2,3-dihydrobenzofuran-5-yl acetonyl |
| 71. | phenyl | cyclopentyl | | OH | — | — | H | 2,3-dihydrobenzofuran-5-yl propyl |
| 72. | phenyl | cyclooctyl | | OH | — | — | H | phenethyl |
| 73. | phenyl | cyclooctyl | | OH | — | — | H | 2-methyl-2-hexenyl |
| 74. | phenyl | cyclohexyl | | OH | — | NH | isobutyryl | H | phenethyl |
| 75. | phenyl | cyclohexyl | | OH | — | NH | propionyl | H | phenethyl |
| 76. | phenyl | cyclohexyl | | OH | — | NH | butyryl | H | phenethyl |
| 77. | phenyl | cyclohexyl | | OH | — | — | CH₂ | H | phenethyl |
| 78. | phenyl | cyclohexyl | | OH | propionyl | NH | CH₂ | H | phenethyl |

TABLE I-continued

FORMULA I $$Ar-\underset{R_2}{\overset{R_1}{C}}-W-\underset{O}{\overset{}{C}}-X-Y-\underset{R_3}{N}-\underset{}{\overset{}{\underset{}{\bigcirc}}}(CH_2)_m\!-\!N-R_4$$

(m = 0)

| Com No. | Ar | R₁ | R₂ | W | X | Y | R₃ | R₄ |
|---|---|---|---|---|---|---|---|---|
| 79. | phenyl | cyclohexyl | OH | isopropyl ketone | NH | CH₂ | H | benzyl (ethylphenyl) |
| 80. | phenyl | cyclohexyl | OH | — | O | isopropyl ketone | H | benzyl (ethylphenyl) |
| 81. | phenyl | cyclopentyl | OH | — | — | — | H | 2-methyl-2-pentenyl |
| 82. | phenyl | cyclopentyl | OH | — | — | — | H | 3-(benzo[d][1,3]dioxol-5-yl)propyl |
| 85. | phenyl | cyclohexyl | OH | — | — | — | H | H |
| 86. | 4-fluorophenyl | cyclohexyl | OH | — | — | — | H | H |
| 87. | 4-methoxyphenyl | cyclohexyl | OH | — | — | — | H | H |
| 88. | 4-methylphenyl | cyclohexyl | OH | — | — | — | H | H |
| 89. | phenyl | 2-ethyl-6-methylpyridin-3-yl | OH | — | — | — | H | H |
| 90. | phenyl | cycloheptyl | OH | — | — | — | H | H |
| 91. | phenyl | cyclobutyl | OH | — | — | — | H | H |
| 92. | phenyl | cyclopropyl | OH | — | — | — | H | H |

TABLE I-continued

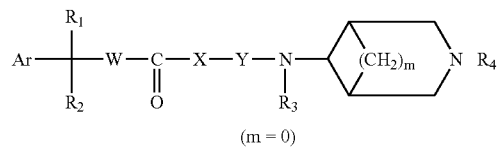

FORMULA I (m = 0)

| Com No. | Ar | $R_1$ | $R_2$ | W | X | Y | $R_3$ | $R_4$ |
|---|---|---|---|---|---|---|---|---|
| 93. | phenyl | cycloheptyl | OH | — | O | —$CH_2$CO— | H | H |
| 94. | phenyl | cyclohexyl | OH | — | O | —CH($CH_3$)CO— | H | H |
| 95. | 4-F-phenyl | 4-F-phenyl | OH | — | O | —$(CH_2)_4$— | $CO_2C(CH_3)_3$ | H |
| 96. | 4-F-phenyl | 4-F-phenyl | O$(CH_2)_2CH_3$ | — | O | $(CH_2)_4$— | —$CO_2C(CH_3)_3$ | H |
| 97. | phenyl | phenyl | H | — | — | — | H | H |
| 98. | phenyl | cyclohexyl | $OCH_3$ | — | — | — | H | H |

The examples mentioned below demonstrate the general synthetic procedure as well as the specific preparation for the particular compounds. The examples are given to illustrate particular aspects of the disclosure and should not be constrained to limit the scope of the invention as defined by the claims.

EXPERIMENTAL DETAILS

Various solvents, such as acetone, methanol, pyridine, ether, tetrahydrofuran, hexanes, and dichloromethane, were dried using various drying reagents according to the procedures well known in the literature. IR spectra were recorded as nujol mulls or a thin neat film on a Perkin Elmer Paragon instrument, Nuclear Magnetic Resonance (NMR) were recorded on a Varian XL-300 MHz instrument using tetramethylsilane as an internal standard.

Example 1

Preparation of (1α,5α,6α)-6-N-(3-azabicyclo[3.1.0] hexyl-3-benzyl)-2-hydroxy-2, 2-diphenyl acetamide (Compound No. 1)

Step a: Preparation of 2-hydroxy-2,2-diphenyl acetic acid: Synthesized as per reported procedure in Vogel's Textbook of Practical Organic Chemistry, page 1046 ($5^{th}$ Ed).

Step b: Preparation of (1α,5α,6α)-3N-benzyl-6-amino-3-azabicyclo[3.1.0]hexane: Synthesized as per reported procedure of Braish, T. F. et. al. Syn. Lett. 1100 (1996).

Step c: To a solution of (1α,5α,6α)-3N-benzyl-6-amino-3-azabicyclo[3.1.0]hexane (1 mmol, 0.188 gm) in DMF (5 ml) was added 2-hydroxy-2,2-diphenyl acetic acid (1 mmol, 0.225 gm) and cooled to 0° C. The reaction mixture was treated with hydroxy benzotriazole (1 mmol, 0.135 g) followed by N-methyl morpholine (2 mmol, 0.202 gm) and stirred at 0° C. for 0.5 hrs. It was followed by the addition of EDC (1-[3-(dimethylamino)propyl]-3-ethyl carbodiimide hydrochloride, (1 mmol. 0.192 gms). The reaction mixture (RM) after stirring at 0° C. for 1 hr. was later stirred at room temperature overnight. The RM was then poured into cold water and extracted with ethyl acetate. The combined organic layers were washed with water and dried over sodium sulphate. The crude compound obtained after removing the solvent was purified by column chromatography (silicagel 100–200 mesh), eluting the compound with 30–70, ethyl acetate-hexane mixture.

m.p.: 172° C.

$^1$H-NMR (CDCl$_3$) δ –7.39–6.29 (m, arom, 10H), 3.58 (s, 2H, benzylic), 3.14–3.07 (m, 3H, piperazine protons & α-hydrogen), 2.38–2.35 (d, 2H, piperazine protons), d 1.42 (d, 2H, cyclopropyl).

IR (K Br): 1657 cm$^{-1}$ (amide carbonyl).

Example 2

Preparation of (1α,5α,6α)-6-N-(3-azabicyclo[3.1.0] hexyl-3-benzyl)-2-hydroxy-2,2-di(4-fluorophenyl) acetamide (Compound No. 2)

This compound was synthesized following the procedure as described in Example 1 using 4-fluorobenzaldehyde instead of benzaldehyde in step a of Example 1 to obtain the corresponding 2-hydroxy-2,2-di(4-fluorophenyl)acetic acid.

$^1$H-NMR (CDCl$_3$) 7.46–6.93 (m, 13H, arom), 3.58 (s, 2H, benzylic), 3.18 (t, 3H, piperazine protons & α-hydrogen), 2.45 (d, 2H, piperazine protons), d 1.5 (s, 2H, cyclopropyl).

IR: 1658 cm$^{-1}$ (amide carbonyl).

Example 3

Preparation of (1α,5α,6α)-6-N-(3-azabicyclo[3.1.0] hexyl-3-benzyl)-2-(2-propenyloxy)-2,2-diphenyl acetamide (Compound No. 3)

Step a: Preparation of 2-allyloxy 2,2-diphenyl acetic acid:
(i) Preparation of ethyl 2-allyloxy-2,2-diphenyl acetate:

A solution of ethyl-2-hydroxy-2,2-diphenyl acetate (1 mmol, 0.256 gm) in N,N-dimethylformamide (DMF) (5 ml) was added to a suspension of sodium hydride (1.2 mmol) in DMF at 0° C. The reaction mixture was stirred at room temperature for 1 hr., then cooled to 0° C. and allyl bromide (1 mmol, 0.117 gm) diluted with 0.5 ml of DMF was added to the reaction mixture and stirred at room temperature for 2 hrs. The reaction was quenched by the addition of a concentrated aqueous solution of ammonium chloride and extracted with ethyl acetate. The combined organic layers were washed with water, brine and dried over sodium sulphate. The crude compound obtained on evaporation of the solvents was purified by column chromatography (silica gel 100–200 mesh), eluting the compound with 0.5–9.5 ethyl acetate-hexane mixture.

$^1$H-NMR: (CDCl$_3$, δ): 7.52–7.3 (m, 10H, arom.), 5.36–5.14 (m, 2H, vinylic), 4.72–4.7 (d,2H, OCH$_2$), 4.29–4.27 (q, 2H, OCH$_2$), 1.3–1.22 (t, 3H, CH$_3$).

IR (DCM): 1738 cm$^{-1}$ (ester carbonyl)

(ii) Preparation of 2-allyloxy-2,2-diphenyl acetic acid:

A solution of ethyl-2-allyloxy-2,2-diphenyl acetate (1 mmol, 0.292 gm) in methanol (5 ml) was added to a solution of potassium hydroxide (2 mmol, 0.112 gms), in 2 ml of water and stirred at room temperature overnight. The organic solvents were removed from the reaction mixture by evaporation and the reaction mixture was acidified with dilute hydrochloric acid to pH-3. The compound was extracted with ethyl acetate. The combined organic layers were washed with water, brine and dried over anhydrous sodium sulphate. The solvent was removed completely to give the title compound in 88% yield, m.p. 125° C.

$^1$H-NMR (CDCl$_3$, δ): 7.48–7.25 (m, 10H, arom.), 5.93–5.84(m,1H, vinylic), 5.32–5.17 (vinylic protons).

IR (KBr): 1713 cm$^{-1}$ (acid carbonyl).

Step b: Preparation of (1α,5α,6α)-6-N-(3-azabicyclo[3.1.0] hexyl-3-benzyl)-2-(2-propenyloxy)-2,2-diphenyl acetamide To a solution of 6-amino-3-azabicyclo[3.1.0]hexane (1 mmol, 0.188 gm) in DMF (5 ml) was added 2-allyloxy-2, 2-diphenyl acetic acid (1 mmol., 0.266 gm). The reaction mixture was cooled to 0° C., and was treated with hydroxy benzotriazole (1 mmol, 0.135 g), followed by the addition of N-methyl morpholine (2 mmol, 0.202 gm) and maintained at 0° C. for 0.5 hrs. It was then followed by the addition of 1-(3-dimethylaminopropyl)-3-ethyl)carbodiimide hydrochloride, (1 mmol, 0.192 gm). The reaction mixture after stirring at 0° C. for 1 hr. was stirred at room temperature overnight. The reaction mixture was poured into cold water and extracted with ethyl acetate. The combined organic layers were washed with water, brine and dried over sodium sulphate. The crude compound obtained on evaporation of the solvents was purified by column chromatography (silicagel, 100–200 mesh), eluting the compound with 30–70, ethyl acetate-hexane mixture.

$^1$H-NMR (CDCl$_3$, δ-values); 7.46–7.09 (m, arom, 15H), 5.84 (m, 1H, allylic), 5.3–5.14 (dd, 2H, allylic) 3.57–3.53 (m, 4H, —N—CH$_2$ & O—CH$_2$) 3.1–3.06 (m, 3H, α-hydrogen and piperazine protons), 2.38–2.35 (d, 2H, piperazine protons).

IR (DCM): 1682 cm$^{-1}$ (amide carbonyl).

Example 4

Preparation of (1α,5α,6α)-6-N-(3-azabicyclo[3.1.0] hexyl-3-benzyl)-2-(2-propenyloxy)-2,2-di(4-fluorophenyl)acetamide (Compound No. 4)

This was synthesized following the procedure as in Example 3 but starting from the corresponding fluoro derivative. m.p. 93–95° C.

$^1$H-NMR (CDCl$_3$); 7.43–6.98 (m, arom, 13H), 5.8 (m, 1H, allylic), 5.2 (m, 2H, allylic), 3.5 (d, 4H, —N—CH$_2$ & O—CH$_2$), 3.06 (d, 3H, α-hydrogen and piperazine protons), 2.36 (d, 2H, piperazine protons).

IR (KBr): 1670 cm$^{-1}$ (amide carbonyl).

Example 5

Preparation of (1α,5α,6α)-6-N-(3-azabicyclo[3.1.0] hexyl-3-benzyl)-2-propyloxy-2,2-diphenyl acetamide (Compound No. 5)

This was synthesized following the procedure as in Example 3 using n-propyl bromide instead of allyl bromide in step a.

$^1$H-NMR (CDCl$_3$): 7.4–7.09 (m, 15H, arom), 3.53 (s, 2H, benzylic),3.09–3.068 (m, 3H, α-hydrogen & piperazine protons).

IR (DCM): 1666 cm$^{-1}$ (amide carbonyl)

Example 6

Preparation of (1α,5α,6α)-6-N-(3-azabicyclo[3.1.0] hexyl-3-benzyl)-2-propyloxy-2,2-di(4-fluoro phenyl) acetamide (Compound No. 6)

This was synthesized following the procedure as in Example 3 using the corresponding fluoro derivative. m.p. 110° C.

$^1$H-NMR (CDCl$_3$): 7.4–6.97 (m, 13H, arom), 3.54 (s, 2H, benzylic), 3.08 (d, 3H, α-hydrogen & piperazine protons), 2.92 (t, 2H, piperazine), 2.37 (d, 2H), 1.56 (m, 4H), 0.9 (t, 3H, methyl).

IR (KBr): 1659 cm$^{-1}$ (amide carbonyl)

Example 7

Preparation of (1α,5α,6α)-6-N-(3-azabicyclo[3.1.0] hexyl-3-benzyl)-2-(2-propynyloxy)-2,2-diphenyl acetamide (Compound No. 7)

This was synthesized following the procedure as described in Example 3 but using propargyl bromide instead of allyl bromide in step a.

$^1$H-NMR (CDCl$_3$): 7.48–7.2 (m, 15H, arom.), 3.73 (s,2H, OCH$_2$), 3.56 (s, 2H, N—3.12–3.09(m, 3H, α-hydrogen & piperazine protons) 2.44–2.39 (m, 3H, piperazine protons & acetylene protons).

IR (DCM): 1680 cm$^{-1}$ (amide carbonyl)

Example 8

Preparation of (1α,5α,6α)-6-N-(3-azabicyclo[3.1.0] hexyl-3-benzyl)-2-hydroxy-2,2-di(2-furyl)acetamide (Compound No. 8)

Step a: Synthesis of 2-hydroxy-2,2-di(2-furyl)acetic acid: Synthesized as per reported procedure in Vogel's Text Book of Practical Organic Chemistry, page 1048 (5$^{th}$ ed).
Step b: The compound was synthesized following the procedure given in step c of Example 1 using 2-hydroxy-2, 2-di(2-furyl)acetic acid instead of 2-hydroxy-2,2-diphenyl acetic acid.

$^1$H-NMR (CDCl$_3$) 7.38–6.29 (m, 11H, arom), 3.58 (s, 2H, bezylic), 3.15 (m, 3H, α-hydrogen & piperazine protons), 2.44–2.41 (m, 2H, piperazine protons), 1.65–1.6 (m, 3H, cyclopropyl).

IR (KBr): 1641 cm$^{-1}$ (amide carbonyl).

Example 9

Preparation of (1α,5α,6α)-6-N-(3-azabicyclo[3.1.0] hexyl-3-benzyl)-2-hydroxy-2,2-di(2-thienyl)acetamide (Compound No. 9)

Step a: Synthesis of 2-hydroxy-2,2-di(2-thienyl)acetic acid: Synthesized as per reported procedure in Vogel's Text Book of Practical Organic Chemistry, page 1048 (5th ed).
Step b: The compound No. 9 was synthesized following the procedure given in step c of Example 1 using 2-hydroxy-2,2-di(2-thienyl)acetic acid instead of 2-hydroxy-2,2-diphenyl acetic acid.

$^1$H-NMR (CDCl$_3$); 7.33–6.93 (m, 6H), 6.33 (s, OH), 3.58 (s, 1H), 3.13–3.10 (m, 1H), 2.43–2.40 (m, 2H), 2.06–2.02 (m, 2H), 1.68 (bm), 1.34–1.24 (m, 2H), 0.90–0.87 (m, 1H).
IR (DCM): 1660 Cm$^{-1}$

Example 10

Preparation of (1α,5α,6α)-4-(6-N-(3-azabicyclo [3.1.0]hexyl-3-benzyl))-N-tert -butyloxycarbonyl) butyl-1-(2-hydroxy-2,2-diphenyl)acetate (Compound No. 10)

Step a: Preparation of 6-[N-α-bromobutyl, N-tert-butyloxycarbonyl, N-3-benzyl-3-azabicyclo[3.1.0]hexane]: A solution of 6-N-tert-butyloxy carbonyl, N-3-benzyl-3-azabicyclo[3.1.0]hexane (1 mmol) in N,N-dimethylformamide (DMF) (5 ml) was added to a cold suspension of sodium hydride in DMF under nitrogen. The reaction mixture was stirred at room temperature for 1 hr., cooled to 0° C. and to it was added a solution of 1,4-dibromobutane (2 mmol) in DMF. The reaction mixture was stirred at room temperature for 3 hrs., quenched the reaction mixture by the addition of aqueous ammonium chloride solution and extracted with ethyl acetate. The combined organic layer was washed with water, brine and dried over sodium sulphate. The crude compound obtained on evaporation of the solvents was purified by column chromatography (silica gel 100–200 mesh), eluting the compound with 25–75, ethyl acetate-hexane mixture.

$^1$H-NMR (CDCl$_3$) 7.33–7.24 (m, 5H, arom.), 3.59 (s, 2H, methylene), 3.46–3.42 (t, 2H, N—CH$_2$), 3.24–3.19 & 3.08–3.05 (d's, 4H, piperazine protons) 2.82 (s, 1H, α-proton), 2.46–2.44 (t,2H, CH$_2$—Br).

IR (DCM): 1683 cm$^{-1}$ (carbamate).

Step b: To a solution of 2-hydroxy-2,2-diphenyl acetic acid (1 mmol, 0.228 gms) in xylene was added, 6-[N-α-bromobutyl, N-tert-butyloxycarbonyl, N-3-benzyl-3-azabicyclo[3.1.0]hexane] (1 mmol, 0.423 gms) and DBU (1,8-diazabicyclo[5,4,0]undec-7-ene, 2 mmol, 0.305 gms) and refluxed the reaction mixture for 6 hrs. The reaction mixture was washed with water, brine and dried over sodium sulphate. The solvents were evaporated and the crude compound thus obtained was purified by column chromatography (silicagel, 100–200 mesh), eluting the compound with 20–80, ethyl acetate-hexane mixture.

$^1$H-NMR (CDCl$_3$); 7.41 to 7.26 (m, 15H, arom), 4.27 (t, 2H, ester-CH$_2$) 3.57 (s, 2H, benzylic).

IR (DCM): 1688 cm$^{-1}$ (carbamate), 1725 cm$^{-1}$ (ester carbonyl)

Example 11

Preparation of (1α,5α,6α)-3-(6-N-(3-azabicyclo [3.1.0]hexyl-3-benzyl))-N-tert -butyloxycarbonyl) propyl-1-(2-hydroxy-2,2-diphenyl)acetate (Compound No. 11)

This compound was synthesized following the procedure of Example 10 by using 1,3-dibromopropane in step a instead of 1,4-dibromobutane.

$^1$H-NMR (CDCl$_3$, δ-values): 7.4–7.25 (m, 15H, arom), 4.34–4.24 (2H, t, ester-CH$_2$), 2.95–2.93 (d, 2H, piperazine protons), 2.74 (s, 1H, α-proton), 2.36 to 2.33 (d, 2H, piperazine protons).

IR (DCM): 1731 cm$^{-1}$ (carbamate), 1688 cm$^{-1}$ (amide carbonyl)

Example 12

Preparation of (1α,5α,6α)-3-(6-N-(3-azabicyclo [3.1.0]hexyl-3-benzyl))-N-tert-butyloxycarbonyl) propyl-1-(2-propyloxy-2,2-diphenyl)acetate (Compound No. 12)

This compound was synthesized following the procedure of Example 10 by reacting 2-propyloxy-2,2-diphenyl acetic acid as obtained in Example 5 and 6-[N-α-bromopropyl, N-tert-butyloxycarbonyl, N-3-benzyl-3-azabicyclo[3.1.0] hexane].

$^1$H-NMR (CDCl$_3$): 7.44–7.22 (m, 15H, arom), 4.18–4.14 (t, 2H, ester —CH$_2$—), 3.54 (s, 2H, benzylic) 3.2–3.16 (t, 2H, —OCH$_2$), 3.11–3.06 (t, 2H, N—CH$_2$), 2.97–2.94 (d, 2H, piperazine protons), 2.75 (s, 1H, α-hydrogen), 2.37–2.34 (d, 2H, piperazine protons).

IR (DCM): 1735 cm$^{-1}$ (carbamate), 1689 cm$^{-1}$ (amide carbonyl)

Example 13

Preparation of (1α,5α,6α)-4-(6-N-(3-azabicyclo [3.1.0]hexyl-3-benzyl))-N-tert-butyloxycarbonyl) butyl-1-(2-propyloxy-2,2-diphenyl)acetate (Compound No. 13)

This compound was synthesized following the procedure of Example 10 by reacting 2-propyloxy-2,2-diphenyl acetic acid as obtained in Example 5 and 6-[N-α-bromobutyl, N-tert-butyloxycarbonyl, N-3-benzyl-3-azabicyclo[3.1.0] hexane].

$^1$H-NMR (CDCl$_3$): 7.45–7.25 (m, 15H, arom), 4.18–4.14 (t, 2H, ester, —CH$_2$—) (s, 2H, benzylic protons), 3.2–3.15 (t, 2H, OCH$_2$), 3.11–3.07 (t, 2H, N—CH$_2$), 3.2–3.15 (t, 2H, OCH$_2$), 3.11–3.07 (t, 2H, N—CH$_2$), 3.2–2.99 (d, 2H, piperazine protons 2.73 (s, 1H, α-proton), 2.42–2.39 (d, 2H, piperazine protons).

IR (DCM): 1733 cm$^{-1}$ (carbamate), 1687$^{-1}$ (amide carbonyl).

Example 14

Preparation of (1α,5α,6α)-4-(6-N-(3-azabicyclo [3.1.0]hexyl-3-benzyl))-N-tert-butyloxycarbonyl) butyl-1-(2-(2-propenyloxy)-2,2-diphenyl)acetate (Compound No. 14)

This compound was synthesized following the procedure as described in Example 10 by reacting 2-(2-propenyloxy)-2,2-diphenyl acetic acid as obtained in Example 3 and 6-[N-α-bromobutyl, N-tert-butyloxycarbonyl, N-3-benzyl-3-azabicyclo [3.1.0]hexane].

$^1$H-NMR (CDCl$_3$): 7.45–7.25 (m, 15H, arom), 5.31–5.12 (d, d, 2H, vinyl), 4.19–4.15 (t, 2H, ester, —CH$_2$), 3.81–3.79 (2H, t-CH$_2$); 3.56 (s, 2H, benzylic)

IR (DCM): 1736 cm$^{-1}$ (carbamate), 1689 cm$^{-1}$ (amide carbonyl)

Example 15

Preparation of (1α,5α,6α)-4-(6-N-(3-azabicyclo [3.1.0]hexyl-3-benzyl))-N-tert-butyloxycarbonyl) butyl-1-(2-hydroxy-2,2-di(4-fluorophenyl))acetate (Compound No. 15)

This compound was synthesized following the procedure of Example 10 by using 2-hydroxy-2,2-di(4-fluorophenyl) acetic acid as obtained in Example 2.

$^1$H-NMR (CDCl$_3$): 7.4–6.98(m, 13H, arom), 4.29–4.24 (t, 2H, ester, —CH$_2$), 3.56 (s, 2H, benzylic), 3.15–3.1 (t, 2H, N—CH$_2$), 3.02–2.98 (m, 2H, piperazine), 2.73 (m, 1H, α-hydrogen), 2.42–2.39(m, 2H, piperazine)

IR (DCM): 1731 cm$^{-1}$ (carbamate), 1686 cm$^{-1}$ (amide carbonyl)

Example 16

Preparation of (1α,5α,6α)-4-(6-N-(3-azabicyclo [3.1.0]hexyl-3-benzyl))-N-tert-butyloxycarbonyl) butyl-1-(2-propyloxy-2,2-di(4-fluorophenyl))acetate (Compound No. 16)

The title compound was synthesized following the procedure described in Example 10 using 2-propyloxy-2,2-di (4-fluorophenyl)acetic acid as obtained in Example 6.

$^1$H-NMR (CDCl$_3$): 7.43–6.98 (m, 13H, arom), 4.2–4.15 (t, 2H, ester, —CH$_2$—) 3 (s, 2H, benzylic protons), 3.2–3.11 (m, 2H, OCH$_2$ & N—CH$_2$), 3.05–3.018 (d, 2H, piperazine protons); 2.76 (s, 1H, α-proton), 2.42–2.39 (d, 2H, piperazine protons).

IR (DCM): 1735 cm$^{-1}$ (carbamate), 1692 cm$^{-1}$ (amide carbonyl).

Example 17

Preparation of (1α,5α,6α)-1-(6-N-(3-azabicyclo[3,1, 0]hexyl-3-benzyl))-N-acetamido-2-(2-propyloxy)-2, 2-diphenyl acetate (Compound No. 17)

Step a: Preparation of 6-N-chloromethylcarbonyl-3-N-benzyl-3-azabicyclo[3.1.0]hexane.

To a solution of 6-amino-3-N-benzyl-3-azabicyclo[3.1.0] hexane [1 mmol, 0.188 gms] in dichloromethane at −10° C. was added chloroacetyl chloride (1 mmol, 0.113 gms) followed by the addition triethylamine (2 mmol, 0.2 gms). The reaction mixture was allowed to cool to room temperature and stirred for 1 hr. at room temperature. It was washed with water, brine and dried over sodium sulphate. The solvent was evaporated to afford the title compound.

$^1$H-NMR (CDCl$_3$): 7.33–7.22 (m, 5H, arom.), 4.01 (s, 2H, COCH$_2$), 3.6 (s, 2H, NCH$_2$), 3.15–3.12 (m, 3H, α-hydrogen & piperazine protons), 2.46–2.43 (d, 2H, piperazine protons).

IR (DCM): 1652 cm$^{-1}$ (amide carbonyl).

Step b: To a solution of 2-propyloxy-2,2-diphenyl acetic acid (1 mmol, 0.153 gms) in xylene, was added 6-N-chloromethylcarbonyl-3-N-benzyl-3-azabicyclo[3.1.0] hexane (1 mmol 0.265 gms) and 1,8-diazabicyclo[5.4.0] undec-7-ene (DBU, 2 mmol, 0.305 gms) and the reaction mixture was refluxed for 6 hrs. The reaction mixture was cooled, washed with water, brine and dried over sodium sulphate. The crude compound obtained on evaporation of the solvent was purified by column chromatography (silicagel 100–200 mesh), eluting the compound with ethylacetate-hexane, (25:75) mixture.

¹H-NMR (CDCl₃): 7.48–7.23 (m, 15H, arom), 4.6 (s, 2H, ester, CH₂); 3.55 (s, 2benzylic), 3.25–3.21 (t, 2H, OCH₂); 3.04–30.01 (d, 2H, piperazine protons), 2.88 (s, 1H, α-hydrogen).

I.R (DCM): 1751 cm$^{-1}$ (ester carbonyl), 1681 cm$^{-1}$ (amide carbonyl)

Example 18

Preparation of (1α,5α,6α)-1-(6-N-(3-azabicyclo[3.1.0]hexyl-3-benzyl))-N-acetamido-2-(2-propenyloxy)-2,2-diphenyl acetate (Compound No. 18)

The title compound was synthesized following the procedure described in Example 17 using 2-propenyloxy-2,2-diphenyl acetic acid as obtained in Example 3 instead of 2-propyloxy-2,2-diphenyl acetic acid, and 6-N-chloromethylcarbonyl-3-N-benzyl-3-azabicyclo[3.1.0]hexane.

¹H-NMR (CDCl₃): 7.49–7.23 (m, 15H, arom.), 5.38–5.15 (m, 2H, vinylprotons); 4.64 (s, 2H, ester-CH₂), 3.85 (d, 2H, —O—CH₂); 3.55 (s, 2H, benzylic), 3.05–3.02 (d, 2H, piperazine protons), 2.89 (s, 1H, α-hydrogen).

IR(DCM)1746.93 cm$^{-1}$ (ester carbonyl), 1672 cm$^{-1}$ (amide carbonyl)

Example 19

Preparation of (1α,5α,6α)-1-(6-N-(3-azabicyclo[3.1.0]hexyl-3-benzyl))-N-propionamido-2-(2-propenyloxy)-2,2-diphenyl acetate (Compound No. 19)

The title compound was synthesized following the procedure as described in Example 17 by reacting 2-propenyloxy-2,2-diphenyl acetic acid as obtained in Example 3, with 6-N-chloromethylcarbonyl-3-N-benzyl-3-azabicyclo[3.1.0]hexane.

¹H-NMR (CDCl₃): 7.52–7.23 (m, 15H, arom), δ 5.37–5.15 (m, 2H, vinylic protons), 3.55 (s, 2H, benzylic protons)

IR (DCM): 1746.48 cm$^{-1}$ (ester carbonyl), 1681 cm$^{-1}$ (amide carbonyl)

Example 20

Preparation of (1α,5α,6α)-1-(6-N-(3-azabicyclo[3.1.0]hexyl-3-benzyl))-N-propionamido-2-(2-propyloxy)-2,2-diphenyl acetate (Compound No. 20)

The title compound was synthesized following the procedure of Example 17 by using 2-propyloxy-2,2-diphenyl acetic acid as obtained in Example 5.

¹H-NMR (CDCl₃): 7.52–7.23 (m, 15H, arom.), 5.31 (m, 1H, ester carboxyl-CH—); 3.55 (s, 2H, benzylic).

IR (DCM): 1746.48 cm$^{-1}$ (ester carbonyl), 1681 cm$^{-1}$ (amide carbonyl)

Example 21

Preparation of (1α,5α,6α)-1-(6-N-(3-azabicyclo[3.1.0]hexyl-3-benzyl))-N-acetamido-2-hydroxy-2,2-di(4-fluorophenyl)acetate (Compound No. 21)

The title compound was synthesized following the procedure as described in Example 17 by using 2-hydroxy-2,2-di(4-fluorophenyl)acetic acid as obtained in Example 2.

¹H-NMR (CDCl₃) 7.41–7.04 (m, 13H, arom), 4.67 (s, 2H, O—CH₂), 3.54 (s, 2H, N—CH₂), 3.05–3.02(d, 2H, piperazine), 2.92 (m, 1H, α-hydrogen), 2.36–2.33(d, 2H, piperazine).

IR (DCM): 1745 cm$^{-1}$ (ester carbonyl), 1664 cm$^{-1}$ (amide carbonyl)

Example 22

Preparation of (1α,5α,6α)-6-N-(3-azabicyclo[3.1.0]hexyl-3-benzyl)-2-cyclohexyl-2-hydroxy-2-phenyl acetamide (Compound No. 22)

Step a: Synthesis of 2-hydroxy-2-cyclohexyl phenyl acetic acid:

This was prepared following the procedure as described in J. Amer. Chem. Soc. 75, 2654 (1953).

Step b: Synthesis of (1α,5α,6α)-6-N-(3-azabicyclo[3.1.0]hexyl-3-benzyl)-2-cyclohexyl-2-hydroxy-2-phenyl acetamide.

The compound of step b was prepared following the procedure as described in step c of Example 1 using 2-hydroxy-2-cyclohexyl phenyl acetic acid instead of 2-hydroxy-2,2-diphenyl acetic acid.

¹H-NMR: (CDCl₃) 7.83–7.26 (m, 10H), 4.29–4.25 (t, 4H), 2.16–2.12 (q, 2H)

I.R. (DCM): 1690 cm$^{-1}$

Example 23

Preparation of (1α,5α,6α)-6-N-(3-azabicyclo[3.1.0]hexyl-3-(3,5-difluoro benzyl))-2-cyclohexyl-2-hydroxy-2-phenyl acetamide (Compound No. 23)

The compound obtained in Example 22 was debenzylated and then N-alkylated as given below:

Step a: A solution of 6-N-(3-azabicyclo[3.1.0]hexyl)-2-hydroxy-2-cyclohexyl-2-phenyl acetamide (1 mmol) in methanol (50 ml) was added to a suspension of Pd/C (10%, 0.1 gm) and the reaction mixture was hydrogenated in Parr apparatus at 45 psi for 3 hrs. The reaction mixture was filtered and concentrated to afford the title compound.

¹H-NMR (CDCl₃): 7.47–6.74 (m, 5H. arom.), 3.24–3.16 (m, 3H, piperazine protons & α-proton), 3.07–3.02 (m, 2H, piperazine protons), IR (DCM): 1660 cm$^{-1}$ (amide carbonyl)

Step b: To a solution of 6-N-(3-azabicyclo[3.1.0]cyclohexyl)-2-hydroxy-2-cyclohexyl-2-phenyl acetamide (1 mmol 0.328 gms) in DMF (5 ml) was added potassium carbonate (2 mmol 0.276 gms), potassium iodide (1 mmol 0.166 gms) and 3,5-difluoro benzyl bromide (1.2 mmol 0.2 gms). The reaction mixture was stirred at room temperature overnight, poured into water and extracted with ethyl acetate. The combined organic layer was washed with water, brine and dried over sodium sulphate. The crude compound obtained after evaporation of the solvent under vacuum was purified by column chromatography (silica gel 100–200 mesh), eluting the compound with ethyl acetate.

¹H-NMR(CDCl₃) 7.59–6.6 (m, 8H, arom.), 4.07 (s, 2H, N—CH₂); 3.49–3.47(m, 3H, piperazine & α-hydrogen).

IR (DCM): 1655 cm$^{-1}$ (amide carbonyl)

Example 24

Preparation (1α,5α,6α)-6-N-(3-azabicyclo[3.1.0]hexyl-3-(4-bromobenzyl))-2-cyclohexyl-2-hydroxy-2-phenyl acetamide (Compound No. 24)

This compound was synthesized following the procedure as in Example 23 but using 4-bromobenzyl bromide instead of 3,5-difluoro benzyl bromide.

$^1$H-NMR(CDCl$_3$) 7.72–7.2 (m, 9H, arom.), 3.61 (s, 2H, N—CH$_2$); 3.18–3.09(m, 3H, piperazine & α-hydrogen), 2.48–2.45(m, 2H, piperazine).

IR (DCM): 1658 cm$^{-1}$ (amide carbonyl)

Example 25

Preparation of (1α,5α,6α)-6-N-(3-azabicyclo[3.1.0]hexyl-3-(2,6-difluoro benzyl))-2-cyclohexyl-2-hydroxy-2-phenyl acetamide (Compound No. 25)

The title compound was synthesized following the procedure as described in Example 23 using 2,6-difluorobenzyl bromide instead of 3,5-difluoro benzyl bromide.

$^1$H-NMR(CDCl$_3$) 7.59–6.82 (m, 8H, arom.), 3.73(s, 2H, N—CH2); 3.06–3.01(m, 2H, piperazine) 2.89(1H, m, α-hydrogen), 2.48–2.45(m, 2H, piperazine).

IR (DCM): 1635 cm$^{-1}$ (amide carbonyl)

Example 26

Preparation of (1α,5α,6α)-6-N-(3-azabicyclo[3.1.0]hexyl-3-(2-phenylbenzyl))-2-cyclohexyl-2-hydroxy-2-phenyl acetamide (Compound No. 26)

The title compound was synthesized following the procedure as described in Example 23 using 2-bromomethyl biphenyl instead of 3,5-difluoro benzyl bromide.

$^1$H-NMR(CDCl$_3$) 7.59–7.21 (m, 14H, arom.), 3.44(s, 2H, N—CH$_2$); 3.028–2.95 (m piperazine) 2.87 (1H, m, α-hydrogen), 2.26–2.25 (m, 2H, piperazine).

IR (DCM): 1659 cm$^{-1}$ (amide carbonyl)

Example 27

Preparation of (1α,5α,6α)-6-N-(3-azabicyclo[3.1.0]hexyl-3-(2-phenylethyl))-2-cyclohexyl-2-hydroxy-2-phenyl acetamide (Compound No. 27)

The compound obtained in step a of Example 23 (300 mg; 1 mmol) was dissolved in acetonitrile (20 ml) and potassium carbonate (1.5 mmol), potassium iodide (catalytical amount) were added to it at room temperature. It was followed by the addition of 2-phenyl ethyl bromide to the reaction mixture and was stirred at reflux for 8 hrs. The reaction mixture was filtered and the filtrate was taken in ethyl acetate. The organic layer was washed with water, brine and dried over sodium sulphate. It was concentrated under reduced pressure and purified over silica gel (100–200 mesh) using ethyl acetate/hexane mixture.

$^1$H-NMR(CDCl$_3$ δ-values) 7.59–7.1 (m, 9H, arom.), 3.15 (t, 2H, N—CH$_2$—C); 2.67–2.59 (m, 3H, piperazine & α-hydrogen), 2.38–2.24 (m, 2H, piperazine).

IR (DCM): 1652 cm$^{-1}$ (amide carbonyl)

Example 28

Preparation of (1α,5α,6α)-6-N-(3-azabicyclo[3.1.0]hexyl-3-(2-(2,3-dihydro benzofuran-5-yl)ethyl))-2-cyclohexyl-2-hydroxy-2-phenyl acetamide (Compound No. 28)

Step a: Synthesis of 5-(2-bromoethyl)-2,3-dihydrobenzofuran.
  The title compound was synthesized following the procedure as given in EP132130 and EP0388054.
Step b: The title compound No. 28 was synthesized by using 5-(2-bromoethyl) 2,3-dihydrobenzofuran following the procedure described in Example 27.

$^1$H-NMR(CDCl$_3$) 7.59–6.6 (m, 8H, arom.), 5.54 (t, 2H, N—CH$_2$—C); 2.59–2.55 (m, 3H, piperazine & α-hydrogen), 2.38–2.34 (m, 2H, piperazine).

IR (DCM): 1651 cm$^{-1}$ (amide carbonyl)

Example 29

Preparation of (1α,5α,6α)-6-N-(3-azabicyclo[3.1.0]hexyl-3-(2-(3,4-methylenedioxyphenyl)ethyl))-2-cyclohexyl-2-hydroxy-2-phenyl acetamide (Compound No. 29)

Step a: Synthesis of 3,4-methylenedioxyphenethyl bromide.
  This compound was synthesized following the procedure as given in EP132130 and EP0388054.
Step b: Compound No. 29 was synthesized following the procedure as described in Example 27 using 3,4-methylenedioxy phenylethyl bromide.

$^1$H-NMR(CDCl$_3$) 7.59–6.56 (m, 8H, arom.), 5.89 (s, 2H, methylenedioxy) 3.15 (t, 2H, N—CH$_2$—C); 2.58–2.55 (m, 3H, piperazine & α-hydrogen), 2.38–2.34 (m, 2H, piperazine).

IR (DCM): 1653 cm$^{-1}$ (amide carbonyl)

Preparation of (1α,5α,6α)-6-N-(3-azabicyclo[3.1.0]hexyl-3-(1-(2,3-dihydro benzofuran-5-yl)acetyl))-2-cyclohexyl-2-hydroxy-2-phenyl acetamide (Compound No. 30)

Step a: Synthesis of 5-chloroacetyl-2,3-dihydrobenzofuran.
  This compound was synthesized following the procedure as given in EP0388054.
Step b: Compound No. 30 was synthesized following the procedure as given in Example 27 using 5-chloroacetyl-2,3-dihydrobenzofuran.

$^1$H-NMR(CDCl$_3$) 7.59–6.6 (m, 8H, arom.), 4.15 (t, 2H, N—CH$_2$—C); 3.17–3.11 (m, 2H, piperazine) 2.85 (m, 1H, α-hydrogen), 2.38–2.34 (m, 2H, piperazine).

IR (DCM): 1651 cm$^{-1}$ (amide carbonyl)

Example 31

Preparation of (1α,5α,6α)-6-N-(3-azabicyclo[3.1.0]hexyl-3-(2-(benzofuran-5-yl)ethyl))-2-cyclohexyl-2-hydroxy-2-phenyl acetamide (Compound No. 31)

Step a: Synthesis of 5-(2-bromoethyl)benzo[2,3-b]furan.
  This compound was synthesized following the procedure as given in EP132130 and EP0388054.
Step b: This was synthesized following the procedure as in Example 27 using 5-(2-bromoethyl)benzo[2,3-b]furan instead of 2-phenyl ethyl bromide.

¹H-NMR(CDCl₃) 7.59–6.59 (m, 9H, arom.), 3.18 (t, 2H, N—CH₂—C); 2.76–2.73 (m, 3H, piperazine & α-hydrogen), 2.38–2.34 (m, 2H, piperazine).
IR (DCM): 1649 cm⁻¹ (amide carbonyl)

Example 32

Preparation of (1α,5α,6α)-6-N-(3-azabicyclo[3.1.0] hexyl-3-methyl)-2-cyclohexyl-2-hydroxy-2-phenyl acetamide (Compound No. 32)

This compound was synthesized following the procedure as described in step b of Example 23 using methyl iodide instead of 3,5-difluoro benzyl bromide.
¹H-NMR (CDCl₃) 7.6–7.19 (m,5H, aromatic) 3.64 (s, 3H, N—CH₃), 3.4 (m, 1H, α-hydrogen) 3.37 to 2.87 (m, 4H, piperazine protons), 2,39 (m, 1H) 1.77 to 0.91 (m, 10H, aliphatic, cyclohexyl), 0.8 (m, 2H, cyclopropyl)
I.R.(DCM): 1656 cm⁻¹

Example 33

Preparation of (1α,5α,6α)-6-N-(3-azabicyclo[3.1.0] hexyl-3-ethyl)-2-cyclohexyl-2-hydroxy-2-phenyl acetamide (Compound No. 33)

This compound was synthesized following the procedure as described in step b of Example 23 using iodoethane instead of 3,5-difluoro benzyl bromide.
¹H-NMR(CDCl₃) 7.6–7.22 (m,5H, aromatic) 3.16 (q, 2H, N—CH₂), 2.88 (m, 1H, α-hydrogen) 2.46 to 2.38 (m, 4H, piperazine protons), 2.1 (m, 1H) 1.77 to 1.2 (m, 10H, aliphatic, cyclohexyl), 1.05 (t, 3H —CH₃) 0.8 (m, 2H, cyclopropyl)
I.R.(DCM): 1657 cm⁻¹

Example 34

Preparation of (1α,5α,6α)-6-N-(3-azabicyclo[3.1.0] hexyl-3-(1-propyl))-2-cyclohexyl-2-hydroxy-2-phenyl acetamide (Compound No. 34)

This compound was synthesized following the procedure as described in step b of Example 23 but using n-propyl bromide instead of 3,5-difluoro benzyl bromide.
M.P.: 78° C.
¹H-NMR(CDCl₃) 7.64–7.27 (m,5H, aromatic) 4.02 to 3.74 (m, 2H, N—CH₂), 2.88 (m, 1H, α-hydrogen) 2.46 to 2.38 (m, 4H, piperazine protons), 2.1 (m, 1H) 1.77 to 1.2 (m, 14H, aliphatic, cyclo hexyl & CH₂—CH₂), 1.05 (t, 3H —CH₃) 0.8 (m, 2H, cyclopropyl)
I.R.(DCM): 1655 cm⁻¹

Example 35

Preparation of (1α,5α,6α)-6-N-(3-azabicyclo[3.1.0] hexyl-3-(2-propargyl))-2-cyclohexyl-2-hydroxy-2-phenyl acetamide (Compound No. 35)

This compound was synthesized following the procedure as in Example 23 using propargyl bromide instead of 3,5-difluoro benzyl bromide.
¹H-NMR(CDCl₃) 7.59–7.22 (m,5H, aromatic) 3.12 to 2.86 (m, 3H, α-hydrogen & piperazine protons) 2.41 to 2.35 (m, 2H, piperazine protons), 1.77 to 1.2 (m, 9H, aliphatic, cyclo hexyl), 0.96 (m, 6H -2×CH₃) 0.8 (m, 2H, cyclopropyl)
I.R.(DCM): 1656 cm⁻¹

Example 36

Preparation of (1α,5α,6α)-6-N-(3-azabicyclo[3.1.0] hexyl-3-(2-propenyl))-2-cyclohexyl-2-hydroxy-2-phenyl acetamide (Compound No. 36)

This compound was synthesized following the procedure as described in Example 23 using allyl bromide instead of 3,5-difluoro benzyl bromide.
¹H-NMR(CDCl₃) 7.6–7.24 (m,5H, aromatic) 5.86 to 5.11 (m, 3H, vinylic protons) 3.21 to 3.13 (m, 3H, α-hydrogen & piperazine protons), 2.97 (m, 2H, N—CH₂) 2.41 to 2.35 (m, 2H, piperazine protons), 1.77 to 1.2 (m, 9H, aliphatic, cyclohexyl), 0.8 (m, 2H, cyclopropyl)
I.R.(KBr): 1653 cm⁻¹

Example 37

Preparation of (1α,5α,6α)-6-N-(3-azabicyclo[3.1.0] hexyl-3-(2-propyl))-2-cyclohexyl-2-hydroxy-2-phenyl acetamide (Compound No. 37)

This compound was synthesized following the procedure as in Example 23 using propyl bromide instead of 3,5-difluoro benzyl bromide.
¹H-NMR(CDCl₃) 7.65–7.22 (m,5H, aromatic) 4.73. (s, 1H) 4.24 (m, 2H, N—CH₂) 3.21 to 3.13 (m, 3H, α-hydrogen & piperazine protons) 2.41 to 2.35 (m, 2H, piperazine protons), 1.77 to 1.2 (m, 9H, aliphatic, cyclo hexyl), 0.8 (m, 2H, cyclopropyl)
I.R.(DCM): 1656 cm⁻¹

Example 38

Preparation of (1α,5α,6α)-6-N-(3-azabicyclo[3.1.0] hexyl-3-cyclopropyl)-2-cyclohexyl-2-hydroxy-2-phenyl acetamide (Compound No. 38)

This compound was synthesized following the procedure as described in Example 23 but using cyclopropyl bromide instead of 3,5-difluoro benzyl bromide.
¹H-NMR(CDCl₃) 7.62–7.22 (m,5H, aromatic) 3.21 to 3.15 (m, 2H, 2x α-hydrogen) 2.74 to 2.66 (m, 3H, piperazine protons) 1.77 to 0.88 (m, 9H, aliphatic, cyclo hexyl), 0.8 (m, 2H, cyclopropyl)
I.R.(DCM): 1660 cm⁻¹

Example 39

Preparation of (1α,5α,6α)-6-N-(3-azabicyclo[3.1.0] hexyl-3-(1-butyl))-2-cyclohexyl-2-hydroxy-2-phenyl acetamide (Compound No. 39)

This compound was synthesized following the procedure as described in Example 23 using n-butyl bromide instead of 3,5-difluoro benzyl bromide.
¹H-NMR(CDCl₃) 7.61–7.23 (m,5H, aromatic) 3.24 (m, 2H, N—CH₂) 2.52 to 2.47 (m, 5H, α-hydrogen & piperazine protons) 1.69 to 1.15 (m, 13H, aliphatic, cyclo hexyl), 0.88 (m, 5H, cyclopropyl & CH₃)
I.R.(DCM): 1664 cm⁻¹

Example 40

Preparation of (1α,5α,6α)-6-N-(3-azabicyclo[3.1.0]hexyl-3-(3-methyl-2-butenyl))-2-cyclohexyl-2-hydroxy-2-phenyl acetamide (Compound No. 40)

This compound was synthesized following the procedure as in Example 23 using isopropenyl bromide instead of 3,5-difluoro benzyl bromide.

$^1$H-NMR(CDCl$_3$) 7.77–7.25 (m, 5H, aromatic) 5.24 (m, 1H, vinylic) 4.04 to 3.96 (m, 2H, N—CH$_2$) 3.83 to 3.35 (m, 5H, α-hydrogen & piperazine protons) 2.47 to 1.22 (m, 17H, aliphatic, cyclo hexyl), 0.88 (m, 2H, cyclopropyl)

I.R.(DCM): 1673 cm$^{-1}$

Example 41

Preparation of (1α,5α,6α)-6-N-(3-azabicyclo[3.1.0]hexyl-3-(4-methyl-3-pentenyl))-2-cyclohexyl-2-hydroxy-2-phenyl acetamide (Compound 41)

This compound was synthesized following the procedure as described in Example 23 using 5-bromo-2-methyl-2-pentene instead of 3,5-difluoro benzyl bromide.

$^1$H-NMR(CDCl$_3$) 7.59–7.22 (m, 5H, aromatic) 5.04 (m, 1H, vinylic) 3.12 to 3.07 (m, 2H, N—CH$_2$) 2.88 (m, 1H, α-hydrogen) 2.36 to 2.04 (m, 4H, piperazine protons) 2.08 to 1.18 (m, 19H, aliphatic, 2x CH$_3$, cyclohexyl), 0.88 (m, 2H, cyclopropyl)

I.R.(DCM): 1655 cm$^{-1}$

Example 42

Preparation of (1α,5α,6α)-6-N-(3-azabicyclo[3.1.0]hexyl-3-(3,4-methylenedioxybenzyl))-2-cyclohexyl-2-hydroxy-2-phenyl acetamide (Compound No. 42)

This compound was synthesized following the procedure as described in Example 23 using 3,4-methylenedioxybenzyl chloride instead of 3,5-difluoro benzyl bromide.

$^1$H-NMR(CDCl$_3$) 7.58–6.60 (m,8H, aromatic) 5.9 (s, 2H, methylene protons) 3.42 (s, 2H, N—CH$_2$), 3.05 to 2.88 (m, 3H, α-hydrogen & piperazine protons) 2.77 (m, 1H, α-hydrogen) 2.38 to 2.29 (m, 2H, piperazine protons) 1.76 to 1.15 (m, 10H, aliphatic cyclo hexyl), 0.88 (m, 2H, cyclopropyl)

I.R.(DCM): 1669 cm$^{-1}$

Example 43

Preparation of (1α,5α,6α)-6-N-(3-azabicyclo[3.1.0]hexyl-3-(6,6-dimethyl-2,4-heptadiynyl))-2-cyclohexyl-2-hydroxy-2-phenyl acetamide (Compound No. 43)

Step a: Synthesis of 1-Chloro-6,6-dimethyl hepta-2,4-diyne. This compound was synthesized following the procedure as described in J. Med. Chem. (1995), 38, 3207–3216.

Step b Compound No. 43 was synthesized following the procedure as described in Example 23 using 1-chloro-6,6-dimethyl hepta-2,4-diyne instead of 3,5-difluoro benzyl bromide.

$^1$H-NMR(CDCl$_3$) 7.59–7.22 (m,5H, aromatic), 3.4 (s, 2H, N—CH$_2$), 2.97 to 2.82 (m, 5H, α-hydrogen & piperazine protons) 2.68 (m, 1H, α-hydrogen) 1.8 to 1.1 (m, 19H, aliphatic cyclohexyl), 0.88 (m, 2H, cyclopropyl)

I.R.(DCM): 1666 cm$^{-1}$

Example 44

Preparation of (1α,5α,6α)-6-N-(3-azabicyclo[3.1.0]hexyl-3-benzoyl)-2-cyclohexyl-2-hydroxy-2-phenyl acetamide (Compound No. 44)

This compound was synthesized following the procedure as in Example 23 using benzoyl chloride.

$^1$H-NMR(CDCl$_3$) 7.57–7.22 (m, 10H, arom.), 3.65–3.52–2.55 (m, 2H, piperazine), 2.64 (α-hydrogen), 2.4–2.36 (m, 2H, piperazine).

IR: 1667 cm$^{-1}$ and 1617 cm$^1$ (amide carbonyl)

Example 45

Preparation of (1α,5α,6α)-6-N-(3-azabicyclo[3.1.0]hexyl-3-(2-formyl-fur-5-yl))-2-cyclohexyl-2-hydroxy-2-phenyl acetamide (Compound No. 45)

This compound was synthesized following the procedure as in Example 23 using 2-formyl-5-chloromethylfuran instead of 3,5-difluoro benzyl bromide.

$^1$H-NMR(CDCl$_3$): 9.54 (s, 1H, formyl) 7.58–7.22 (m, 5H, arom.), 7.16 & 6.34 (d, 2×1H, arom. furan) 3.7 (s, 1H N—CH$_2$) 3.13–3.08 (m, 2H, piperazine), 2.91 (α-hydrogen), 2.68–2.63 (m, 2H, piperazine)., 2.38 (m, 1H, α-H in cyclo hexyl), 1.76–0.82 (m, 12H, cyclohexyl, cyclopropyl)

IR: 1724 cm$^{-1}$ (formyl) & 1675 cm$^{-1}$ (amide carbonyl)

Exmaple 46

Preparation of (1α,5α,6α)-6-N-(3-azabicyclo[3.1.0]hexyl-3-(aniline)thiourea)-2-cyclohexyl-2-hydroxy-2-phenyl acetamide (Compound No. 46)

To a solution of 6-N-(3-azabicyclo[3.1.0]cyclohexyl)-2-hydroxy-2-cyclohexyl, 2-phenyl acetamide (1 mmol 0.328 gms) in dichloromethane (10 ml), was added phenyl thiocyanate (1 mmol, 0.135 gms) and the reaction mixture was stirred at room temperature for 6 hours. The reaction mixture was concentrated and purified by column chromatography (silicagel 100–200 mesh), eluting the compound with ethyl acetate—hexane mixture.

$^1$H-NMR (CDCl$_3$) 7.62–6.91 (m, 10H, arom.), 3.77–3.68 (m, 2H, piperazine), 2.59 (s, 1H, α-hydrogen), 2.42–2.17 (m, 2H, piperazine).

IR (DCM):

Example 47

Preparation of (1α,5α,6α)-6-N-(3-azabicyclo[3.1.0]hexyl-3-(methyl, 4-amino-1-phenyl acetate) urea)-2-cyclohexyl-2-hydroxy-2-phenyl acetamide (Compound No. 47)

This compound was synthesized following the procedure as described in Example 46, using 4-methoxy-acetylphenylisocyanate instead of phenyl thiocyanate.

$^1$H-NMR (CDCl$_3$) 7.59–7.14 (m, 10H, arom.), 3.66 (s, 3H, —OCH$_3$), 3.77–3.68 ( 2H, piperazine), 2.59 (s, 1H, α-hydrogen), 2.42–2.17 (m, 2H, piperazine).

IR (DCM): 1736 cm$^{-1}$ (ester carbonyl), 1650 cm$^{-1}$ (amide carbonyl).

Example 48

Preparation of (1α,5α,6α)-6-N-(3-azabicyclo[3.1.0] hexyl-3-(4-amino-1-phenyl aceticacid) urea)-2-cyclohexyl-2-hydroxy-2-phenyl acetamide (Compound No. 48)

This compound was obtained on hydrolysis of compound 47 with sodium hydroxide.

$^1$H-NMR (CDCl$_3$) 7.62–6.91 (m, 10H, arom.), 3.77–3.68 (m, 2H, piperazine), 2.59 (s, 1H, α-hydrogen), 2.42–2.17 (m, 2H, piperazine).

IR (DCM): 1717 cm$^{-1}$ (acid carbonyl), 1640 cm$^{-1}$ (amide carbonyl).

Example 49

Preparation of (1α,5α,6α)-6-N-(3-azabicyclo[3.1.0] hexyl-3-(4-methylphenyl-1-sulphonamide) urea)-2-cyclohexyl-2-hydroxy-2-phenyl acetamide (Compound No. 49)

This compound was synthesized following the procedure as described in Example 46 using 4-methylphenyl-1-sulphonamide cyanate instead of phenyl thiocyanate.

$^1$H-NMR (CDCl$_3$ δ) 7.91–6.84 (m, 9H, arom.), 3.58 (m, 2H, piperazine), 4.13 (s, 1H, α-hydrogen), 3.39 (m, 2H, piperazine).

IR: 1749 cm$^{-1}$, 1681 cm$^{-1}$ & 1667 cm$^{-1}$

Example 50

Preparation of (1α,5α,6α)-6-N-(3-azabicyclo[3.1.0] hexyl-3-benzyl)-2-cyclohexyl-2-hydroxy-2-(4-methylphenyl)acetamide (Compound No. 50)

Step a: Preparation of 2-(4-methylphenyl)-2-cyclohexyl-2-hydroxy acetic acid. This compound was synthesized as per reported procedure in Syn. Comm. 11 (12) 943–946 (1981).

Step b: Compound No. 50 was synthesized following the method as given in step c of Example 85 using 2-(4-methylphenyl)-2-cyclohexyl-2-hydroxy acetic acid instead of 2-hydroxy-2,2-diphenyl acetic acid.

m.p.: 171° C.

$^1$H-NMR (CDCl$_3$): 7.45 (d, 2H, arom.), 7.25–7.21 (m, 5H, arom.), 7.14–7.11 (d, 2H, arom.), 6.55 (s, broad, 1H, —OH), 3.53 (s, 2H, methylene), 3.06–2.97 (m, 3H, α-H & piperazine protons).

IR (DCM): 1656 cm$^{-1}$ (amide carbonyl)

Example 51

Preparation of (1α,5α,6α)-6-N-(3-azabicyclo[3.1.0] hexyl-3-benzyl)-2-cyclohexyl-2-hydroxy-2-(4-methoxyphenyl)acetamide (Compound No. 51)

This compound was synthesized following the procedure as in Example 50 using 2-(4-methoxyphenyl)-2-cyclohexyl-2-hydroxy acetic acid instead of 2-(4-methylphenyl)-2-cyclohexyl-2-hydroxy acetic acid.

$^1$H-NMR data (CDCl$_3$): 7.51–7.48 (d, 2H, arom) 7.32 to 7.12 (m, 5H, arom), 6.89–6.86 (d, 2H, arom), 6.59 (s, broad, 1H, —OH), 3.8 (s, 3H, —OCH$_3$), 3.54 (s, 2H, benzylic)

I.R. (DCM): 1655 cm$^{-1}$ (amide carbonyl).

Example 52

Preparation of (1α,5α,6α)-6-N-(3-azabicyclo[3.1.0] hexyl-3-benzyl)-2-cyclohexyl-2-hydroxy-2-(4-phenoxyphenyl)acetamide (Compound No. 52)

This compound was synthesized following the procedure as described in Example 50 using 2-(4-phenoxyphenyl)-2-cyclohexyl-2-hydroxy acetic acid instead of 2-(4-methylphenyl)-2-cyclohexyl-2-hydroxy acetic acid.

Analytical data: m.p: 178° C.

$^1$H-NMR data (CDCl$_3$): 7.55–6.94 (m, 14H, arom), 6.64 (s, broad, 1H, hydroxyl), 3.53 (s, 2H, benzylic), I.R(DCM): 1655 cm$^{-1}$ (amide carbonyl)

Example 53

Preparation of (1α,5α,6α)-6-N-3-azabicyclo[3.1.0] hexyl-3-benzyl)-2-cyclohexyl-2-hydroxy-2-(4-fluorophenyl)acetamide (Compound No. 53)

This compound was synthesized following the procedure as described in Example 50 using 2-(4-fluorophenyl)-2-cyclohexyl-2-hydroxy acetic acid instead of 2-(4-methylphenyl)-2-cyclohexyl-2-hydroxy acetic acid.

$^1$H-NMR Data (CDCl$_3$, δ-values): 7.63–7.58 (m, 2H, arom), 7.32–7.21 (m, 2H, arom), 7.09–7.023 (m, 2H, arom), 6.7 (s, broad, 1H, hydroxyl) 3.57 (s, 2H, benzylic), 3.13–3.04 (m, 3H, α-H & piperazine protons)

IR (DCM): 1655 cm$^{-1}$ (amide carbonyl)

Example 54

Preparation of (1α,5α,6α)-6-N-(3-azabicyclo[3.1.0] hexyl-3-benzyl)-2-cyclo hexyl-2-hydroxy-2-(3,4-methylenedioxyphenyl)acetamide (Compound No. 54)

This compound was synthesized following the procedure as described in Example 50 using 2-(3,4-methylenedioxyphenyl)-2-cyclohexyl-2-hydroxy acetic acid instead of 2-(4-methylphenyl)-2-cyclohexyl-2-hydroxy acetic acid.

Analytical data: m.p: 185° C.

$^1$H-NMR data (CDCl$_3$): 7.25 (m, 5H, arom), 7.03 (d, 2H, arom), 6.76–6.73 (d, 2H, arom), 6.56 (s, broad, 1H, hydroxyl), 5.93 (d, 2H, methylenedioxy), 3.53 (s, 2H, benzylic), 3.08–2.99 (m, 3H, α-hydrogen & piperazine protons), 2.37–2.29 (m, 2H, piperazine protons).

IR (DCM): 1654 cm$^{-1}$ (amide carbonyl).

Example 55

Preparation of (1α,5α,6α)-6-N-(3-azabicyclo[3.1.0] hexyl-3-benzyl)-2-cyclohexyl-2-hydroxy-2-(4-tertbutylphenyl)acetamide (Compound No. 55)

This compound was synthesized following the procedure as described in Example 50 using 2-(4-tertbutylphenyl)-2-cyclohexyl-2-hydroxy acetic acid instead of 2-(4-methylphenyl)-2-cyclohexyl-2-hydroxy acetic acid.

Analytical data: m.p: 165° C.

$^1$H-NMR (CDCl$_3$,) 7.48–7.45 (d, 2H, arom), 7.34–7.31 (2H, d, arom), 7.22–7.18 (m, 5H, arom), 6.58 (s, 1H, broad), 3.52 (s, 2H, benzylic), 3.07–2.99 (m, 3H, α-hydrogen & piperazine protons)

IR (KBr): 1655 cm$^{-1}$ (amide carbonyl)

Example 56

Preparation of (1α,5α,6α)-6-N-(3-azabicyclo[3.1.0]hexyl-3-(4-methyl-3-pentenyl))-2-cyclohexyl-2-hydroxy-2-(4-methylphenyl)acetamide (Compound No. 56)

The compound from Example 50 was debenzylated following the procedure as given in Example 23 to afford 6-N-(3-azabicyclo[3.1.0]cyclohexyl)-2-hydroxy-2-cyclohexyl-2-(4-methylphenyl)acetamide. To 6-N-(3-azabicyclo[3.1.0]cyclohexyl)-2-hydroxy-2-cyclohexyl-2-(4-methylphenyl)acetamide (1 mmol 0.328 gms) in DMF (5 ml), were added potassium carbonate (2 mmol 0.276 gms), potassaium iodide (1 mmol 0.166 gms) and 5-bromo-2-methyl-2-pentene (1.2 mmol 0.2 gms). The reaction mixture was stirred at room temperature overnight, poured into water and extracted with ethyl acetate. The combined organic layers were washed with water, brine and dried over sodium sulphate. The crude compound obtained on evaporation of the solvents was purified by column chromatography (silica gel 100–200 mesh), eluting the compound with ethyl acetate.

$^1$H-NMR (CDCl$_3$): 7.45 (d, 2H, arom.), 7.14–7.12 (d, 2H, arom), 5.04 (t, 1H, vinylic proton; 3.11–3.06 (t, 2H, NH$_2$) 2.85 (s, 1H, α-hydrogen).

IR (DCM): 1655 cm$^{-1}$ (amide carbonyl)

Example 57

Preparation of (1α,5α,6α)-6-N-(3-azabicyclo[3.1.0]hexyl-3-(4-methyl-3-pentenyl))-2-cyclohexyl-2-hydroxy-2-(4-methoxyphenyl)acetamide (Compound No. 57)

This compound was synthesized following the procedure as described in Example 56 using 6-N-(3-azabicyclo[3.1.0]hexyl)-2-hydroxy-2-cyclohexyl-2-(4-methoxylphenyl)acetamide instead of 6-N-(3-azabicyclo[3.1.0]hexyl)-2-hydroxy-2-cyclohexyl-2-(4-methylphenyl)acetamide $^1$H-NMR (CDCl$_3$, δ-values): 7.53–7.46 (d, 2H, arom), 6.9–6.83 (d, 2H, arom.), 5.07 (t, 1H, vinylic proton), 3.79 (s, 3H—COH$_3$), 3.11–3.06 (t, 2H, N—CH$_2$)

IR (DCM): 1657 cm$^{-1}$ (amide carbonyl)

Example 58

Preparation of (1α,5α,6α)-6-N-(3-azabicyclo[3.1.0]hexyl-3-(4-methyl-3-pentenyl))-2-cyclohexyl-2-hydroxy-2-(4-fluorophenyl)acetamide (Compound No. 58)

This compound was synthesized following the procedure as described in Example 56 using 6-N-(3-azabicyclo[3.1.0]hexyl)-2-hydroxy-2-cyclohexyl-2-(4-fluorophenyl)acetamide instead of 6-N-(3-azabicyclo[3.1.0]hexyl)-2-hydroxy-2-cyclohexyl-2-(4-methylphenyl)acetamide.

$^1$H-NMR (CDCl$_3$) 7.58–7.53 (q, 4H, arom), 5.047 (d, 1H, vinylic proton), 3.13–3.078 (t, 2H, N—CH$_2$).

IR (DCM): 1656 cm$^{-1}$ (amide carbonyl)

Example 59

Preparation of (1α,5α,6α)-6-N-(3-azabicyclo[3.1.0]hexyl-3-benzyl)-2-cyclohexyl-2-methoxy-2-phenyl acetamide (Compound No. 59)

This compound was synthesized following the procedure as described in Example 3 using methyl iodide and starting from methyl 2-hydroxy-2-cyclohexyl-2-phenyl acetate (J. Amer. Chem. Soc. 75, 2654 (1953)).

$^1$H-NMR (CDCl$_3$) 7.42–7.20 (m, 10H, arom), 6.68 (b, 1H, NH), 3.56 (s, 2H, N—CH$_2$ 3.12–3.07 (m, 5H, —OCH$_3$, piperazine protons, α-hydrogen), 2.41–2.38 (m, 2H, piperazine protons), 2.28 (m, 1H, α-H), 1.96–1.1 (m, 8H), 0.89 (m, 2H, cyclopropyl)

IR (DCM): 1665 cm$^{-1}$

Example 60

Preparation of (1α,5α,6α)-6-N-(3-azabicyclo[3.1.0]hexyl-3-ethyl)-2-cyclohexyl-2-methoxy-2-phenyl acetamide (Compound No. 60)

This compound was synthesized following the procedure as described in Example 23, using 6-N-(3-azabicyclo[3.1.0]hexyl)-2-methoxy-2-cyclohexyl-2-phenyl acetamide instead of 6-N-(3-azabicyclo[3.1.0]hexyl)-2-hydroxy-2-cyclohexyl-2-phenyl acetamide in step a, and ethyl bromide instead of 3,5-difluoro benzyl bromide in step b of Example 23.

$^1$H-NMR (CDCl$_3$) 7.35–7.14 (m, 5H, arom.), 4.22 (m, 2H, N—CH$_2$), 3.57–3.43 (m —OCH$_3$, piperazine protons, α-hydrogen), 2.47–2.38 (m, 2H, piperazine protons) 2.28 (m, 1H, α-H), 1.96–1.1 (m, 8H), 0.89 (m, 2H, cyclopropyl)

IR (DCM): 1665 cm$^{-1}$

Example 61

Preparation of (1α,5α,6α)-6-N-(3-azabicyclo[3.1.0]hexyl-3-benzyl)-2-cyclohexyl-2-(2-propenyloxy)-2-phenyl acetamide (Compound No. 61)

This compound was synthesized following the procedure as described in Example 3, using ethyl-2-hydroxy-2-cyclohexyl phenyl acetate instead of ethyl-2-hydroxy-2,2-diphenyl acetate in step (i) a, and ethyl-2-allyloxy-2-cyclohexyl-2-phenyl acetate instead of ethyl-2-allyloxy-2,2-diphenyl acetate in step (ii) a of Example 3.

$^1$H-NMR (CDCl$_3$): 7.48–7.20 (m, 10H, arom.), 6.0–5.12 (m, 3H, vinylic protons), 3.55 (s, 2H, N—CH$_2$), 3.12–3.09 (m, 2H, O—CH$_2$), 2.40–2.22 (m, 5H, piperazine protons, α-hydrogen) 1.7 to 1.1 (m, 10H, cyclohexyl), 0.89 (m, 2H, cyclopropyl)

IR (DCM): 1678 cm$^{-1}$

Example 62

Preparation of (1α,5α,6α)-6-N-(3-azabicyclo[3.1.0]hexyl-3-(4-methyl-3-pentenyl))-2-cyclohexyl-2-methoxy-2-phenyl acetamide (Compound No. 62)

This compound was synthesized following the procedure as described in Example 23 using 6-N-(3-azabicyclo[3.1.0]hexyl)-2-methoxy-2-cyclohexyl-2-phenyl acetamide instead of 6-N-(3-azabicyclo[3.1.0]hexyl)-2-hydroxy-2-cyclohexyl-2-phenyl acetamide in step a, and 4-methyl-3-pentenyl bromide instead of 3,5-difluoro benzyl bromide in step b of Example 23.

$^1$H-NMR (CDCl$_3$) 7.42–7.26(m, 5H, arom.), 4.08 (m, 1H. vinylic) 3.17 to 2.97 (m, 5H, —OCH$_3$, piperazine protons, α-hydrogen), 2.38–2.28 (m, 4H, piperazine protons N—CH$_2$),), 2.09 (m, 1H, α-H), 1.96–1.1 (m, 18H, cyclohexyl, 2x—CH$_3$, —CH$_2$)., 0.89 (m, 2H, cyclopropyl)

IR (DCM): 1655 cm$^{-1}$

Example 63

Preparation of (1α,5α,6α)-6-N-(3-azabicyclo[3.1.0] hexyl-3-(2,4-difluorobenzyl))-2-cyclohexyl-2-methoxy-2-phenyl acetamide (Compound No. 63)

This compound was synthesized following the procedure as described in Example 23 using 6-N-(3-azabicyclo[3.1.0]hexyl)-2-methoxy-2-cyclohexyl-2-phenyl acetamide instead of 6-N-(3-azabicyclo[3.1.0]hexyl)-2-hydroxy-2-cyclohexyl-2-phenyl acetamide in step a, and 2,4-difluorobenzyl bromide instead of 3,5-difluoro benzyl bromide in step b of Example 23.

$^1$H-NMR: (CDCl$_3$) 8.19–8.01 (m, 3H, arom.), 7.36–6.86 (m, 5H, arom.), 5.37 (s, 1H), 5.12–5.10 (s, 2H), 3.08 (s, 3H), 2.33–0.85 (m, 11H)

IR: 1670 cm$^{-1}$

Example 64

Preparation of 1α,5α,6α)-6-N-(3-azabicyclo[3.1.0] hexyl-3-benzyl)-2-cyclopentyl-2-hydroxy-2-phenyl acetamide (Compound No. 64)

Step a: Synthesis of 2-hydroxy-2-cyclopentyl-2-phenyl acetic acid. This was synthesized following the procedure in J. Amer. Chem. Soc. 75, 2654 (1953).

Step b: The amide was synthesized following the procedure in step c of Example 85 using 2-hydroxy-2-cyclopentyl-2-phenyl acetic acid instead of 2-hydroxy-2,2-diphenyl acetic acid.

Analytical data:

m.p.: 61–65° C.

I.R.: 1658 cm$^{-1}$ $^1$H-NMR (CDCl$_3$): 1.1–3 (due to cyclopentyl and bicyclic amine protons), 3.5 (s, 2H, N—CH$_2$) 6.43 (1H, OH, S), 7.22–7.58 (m, 10H, aromatic).

Example 65

Preparation of (1α,5α,6α)-6-N-(3-azabicyclo[3.1.0] hexyl-3-(4-methyl-3-pentenyl))-2-cyclopentyl-2-hydroxy-2-phenyl acetamide (Compound No. 65)

The compound was synthesized starting from Compound No. 64, which was debenzylated following the method as described in step a of Example 23, and then N-alkylated as given in Example 41.

I.R.: 1658 cm$^{-1}$ $^1$H-NMR (CDCl$_3$): 7.55–7.58 (m, 2H, aromatic) 7.22–7.35 (3H, m, aromatic) 6.35 (s, 1H, OH) 5.0 (t, 1H, allylic proton), 1.1–3.4 (Due to Aliphatic)

Example 66

Preparation of (1α,5α,6α)-6-N-(3-azabicyclo[3.1.0] hexyl-3-(2-(3,4-methylenedioxyphenyl)ethyl)-2-cyclopentyl-2-hydroxy-2-phenyl acetamide (Compound No. 66)

The compound was synthesized starting from Compound No. 64, which was debenzylated following the method as described in step a of Example 23, and then N-alkylated as given in Example 29.

I.R.: 1665 cm$^{-1}$ $^1$H-NMR (CDCl$_3$): 0.85–3.48 (due to aliphatic) 5.89 (s, 2H, methylenedioxy CH$_2$) 6.39 (s, 1H, OH), 6.39–7.58 (m, 8H, Aromatic)

Example 67

Preparation of (1α,5α,6α)-6-N-(3-azabicyclo[3.1.0] hexyl-3-(2-phenylethyl))-2-cyclopentyl-2-hydroxy-2-phenyl acetamide (Compound No. 67)

The compound was synthesized starting from Compound No. 64, which was debenzylated following the method as described in step a of Example 23, and then N-alkylated as given in Example 27. Yield 98%

IR (DCM) cm$^{-1}$ 1650 (amide carbonyl)

$^1$H-NMR (CDCl$_3$, δ-values) 7.59–7.13(m, 10H, aromatic), 3.16–3.13 (m, 2H, N—CH$_2$), 3(m, 1H, α-H in cyclopentyl), 2.68–2.59(m, 3H, piperazine and α-H), 2.37–2.34(m, 2H, piperazine), 1.62–1.1(m, 10H, cyclopentyl and benzylic CH$_2$), 0.88(m, 2H, cyclopropyl).

Example 68

Preparation of (1α,5α,6α)-6-N-(3-azabicyclo[3.1.0] hexyl-3-(2-(2,3-dihydrobenzofuran-5-yl)ethyl))-2-cyclopentyl-2-hydroxy-2-phenyl acetamide (Compound No. 68)

The compound was synthesized starting from Compound No. 64 which was debenzylated following the method as described in step a of Example 23, and then N-alkylated as given in Example 28.

IR (DCM) cm$^{-1}$ 1659 (amide carbonyl)

$^1$H-NMR (CDCl$_3$) 7.59–6.64(m, 10H, aromatic), 4.54–4.49(t,2H, O—CH$_2$), 3.17–3.12 (m, 5H, piperazine, N—CH$_2$ and α-Hydrogen), 2.85–2.84(m, 1H, α-H in cyclopentyl), 2.59–2.54(m, 4H, piperazine and benzofuran CH$_2$), 2.36–2.33(m, 2H, benzylic CH$_2$), 1.67–1.1(m, 8H, cyclopentyl), 0.87 (m, 2H, cyclopropyl).

Example 69

Preparation of (1α,5α,6α)-6-N-(3-azabicyclo[3.1.0] hexyl-3-(2-methyl-pyrid-6-yl)-2-cyclopentyl-2-hydroxy-2-phenyl acetamide (Compound No. 69)

Step a: Synthesis of 2-chloromethyl-5-methylpyridine hydrochloride: To 2-hydroxymethyl-5-methylpyridine (123 mg, 1 mmol) in chloroform at 0° C., thionyl chloride (2.5 mmol) was slowly added. The reaction mixture was then stirred at 0° C. overnight. The volatile material was removed under reduced pressure and the residue was crystallized using hexane.

Step b: The title compound was synthesized following the procedure as described in Example 27, using 2-chloromethyl-5-methylpyridine hydrochloride instead of 2-phenyl ethyl bromide.

IR (DCM) cm$^{-1}$ 1660 (amide carbonyl)

$^1$H-NMR (CDCl$_3$) 7.59–6.95(m, 8H, aromatic), 3.67(s, 2H, pyridyl CH$_2$), 3.13–2.98 (m, 4H, piperazine, α-H in cyclopentyl and α-hydrogen), 2.5(s, 3H, methyl), 2.46–2.43 (m, 2H, piperazine), 1.7–1.23(m, 8H, cyclopentyl), 0.88(m, 2H, cyclopropyl).

Example 70

Preparation of (1α,5α,6α)-6-N-(3-azabicyclo[3.1.0] hexyl-3-(1-(2,3-dihydro benzofuran-5-yl)acetyl))-2-cyclopentyl-2-hydroxy-2-phenyl acetamide (Compound No. 70)

The compound was synthesized starting from Compound No. 64, which was debenzylated following the method as described in step a of Example 23, and then N-alkylated as given in Example 30.

IR (DCM) cm$^{-1}$ 1716 (keto), 1663 (amide carbonyl)

$^1$H-NMR (CDCl$_3$) 7.9–6.74(m, 8H, aromatic), 4.66–4.6 (t,2H, O—CH$_2$), 3.71(s, 2H, N—CH$_2$), 3.24–3.14(m, 5H, piperazine, benzofuran-CH$_2$ and α-Hydrogen), 3 (m, 1H, α-H in cyclopentyl), 2.58–2.55(m, 2H, piperazine), 1.67–1.25(m, 8H, cyclopentyl), 0.88(m, 2H, cyclopropyl).

Example 71

Preparation of (1α,5α,6α)-6-N-(3-azabicyclo[3.1.0] hexyl-3-(2-(benzofuran-5-yl)ethyl))-2-cyclopentyl-2-hydroxy-2-phenyl acetamide (Compound No. 71)

The compound was synthesized starting from Compound No. 64, which was debenzylated following the method as described in step a of Example 23, and then N-alkylated as given in Example 31.

IR (DCM) cm$^{-1}$ 1658 (amide carbonyl)

$^1$H-NMR (CDCl$_3$) 7.58–6.68(m, 10H, aromatic), 3.17–3.15(m, 2H, N—CH$_2$), 3 (m, 1H, α-H in cyclopentyl), 2.86–2.85(m, 1H, α-Hydrogen), 2.76–2.74(m, 2H, piperazine), 2.64–2.62(m, 2H, piperazine), 2.38–2.34(m, 2H, benzylic CH$_2$), 1.53–1.23(m, 8H, cyclopentyl), 0.87–0.85 (m, 2H, cyclopropyl).

Example 72

Preparation of (1α,5α,6α)-6-N-(3-azabicyclo[3.1.0] hexyl-3-benzyl)-2-cycloheptyl-2-hydroxy-2-phenyl acetamide (Compound No. 72)

Step a: Synthesis of 2-hydroxy-2-cycloheptyl-2-phenyl acetic acid. This was synthesized following the procedure in J. Amer. Chem. Soc. 75, 2654 (1953).

Step b: The title compound was synthesized following the procedure as described in step c of Example 85 using 2-hydroxy-2-cycloheptyl-2-phenyl acetic acid instead of 2-hydroxy-2,2-diphenyl acetic acid.

IR (DCM) 1659 cm$^{-1}$ (amide carbonyl)

$^1$H-NMR (CDCl$_3$) 7.57–7.0(m, 10H, aromatic), 3.52(s, 2H, N—CH$_2$), 3.07–2.91 (m, 3H, α-H in cyclopentyl, piperazine protons), 2.60(m, 1H, α-Hydrogen in cyclo heptyl), 2.37–2.32(m, 2H, piperazine), 1.7–0.87(m, 14H, cycloheptyl, cyclopropyl protons).

Example 73

Preparation of (1α,5α,6α)-6-N-(3-azabicyclo[3.1.0] hexyl-3-(4-methyl-3-pentenyl))-2-cycloheptyl-2-hydroxy-2-phenyl acetamide (Compound No. 73)

The compound was synthesized starting from Compound No. 72, which was debenzylated following the method as described in step a of Example 23, and then N-alkylated as given in example 41.

IR (DCM) cm$^{-1}$ 1659.8 (amide carbonyl), 3397.7 (O—H)

$^1$H-NMR (CDCl$_3$) 7.69–7.26(m, 5H, aromatic), 6.38(m, 1H, vinylic), 3.17–3.15(m, 2N—CH$_2$), 2.86–2.63 (m, 4H, piperazine, α-H in cycloheptyl, α-Hydrogen), 2.38(m, 2H, piperazine), 1.41–1.11(m, 12H, cycloheptyl), 0.87–0.85 (m, 2H, cyclopropyl).

Example 74

Preparation of 2-Amino-((1α,5α,6α)-6-N-(3-azabicyclo[3.1.0]hexyl-3-benzyl) propionamido)-2-cyclohexyl-2-hydroxy-2-phenyl acetamide (Compound No. 74)

Step a: Preparation of 2-amino-(1α,5α,6α)-6-N-(3-azabicyclo[3.1.0]hexyl-3-benzyl) propionamide: 2-(Boc-amino) propionic acid was condensed with (1α,5α,6α)-6-amino-3-azabicyclo[3,1,0]hexane, following the procedure as described in step c of Example 85. The N-Boc compound thus obtained was deprotected with 10% trifluoro acetic acid in dichloromethane to afford the free amino compound.

Step b: Compound No. 74 was prepared through the reaction of the compound obtained in step a above with 2-hydroxy-2-cyclohexyl-2-phenyl acetic acid, following the procedure given in step c of Example 85.

$^1$H-NMR(CDCl$_3$): 7.6–7.15 (m, 10H, arom.), 4.22 (m, 1H), 3.55 (d, 2H), 3.08 (q, 2H), 2.95 (q, 2H), 2.86 (s, 1H), 2.37 (m, 2H), 2.35 (m, 1H), 1.65 (d, 1H), 1.25 (m, 9H), 0.88 (q, 2H).

Example 75

Preparation of 2-Amino-((1α,5α,6α)-6-N-(3-azabicyclo[3.1.0]hexyl-3-benzyl) acetamido)-2-cyclohexyl-2-hydroxy-2-phenyl acetamide (Compound No. 75)

This compound was synthesized following the procedure as described in Example 74 using 2-(Boc-amino)acetic acid in step a instead of 2-(Boc-amino)propionic acid.

$^1$H-NMR(CDCl$_3$) 7.61–7.18 (m, 10H, arom), 3.78–3.76 (d, 2H, α-methylene), 3.54 (s, 2H, benzylic protons).

IR: 1666 cm$^{-1}$ (broad, amide carbonyl)

Example 76

Preparation of 3-Amino-((1α,5α,6α)-6-N-(3-azabicyclo[3.1.0]hexyl-3-benzyl) propionamido)-2-cyclohexyl-2-hydroxy-2-phenyl acetamide (Compound No. 76)

This compound was synthesized following the procedure as described in Example 74, using 3-(Boc-amino)propionic acid in step a instead of 2-(Boc-amino)propionic acid.

$^1$H-NMR(CDCl$_3$) 7.59–7.2 (m, 10H, arom), 3.56 (s, 2H, benzylic protons), 3.46–3.44 (d, 2H, N—CH$_2$), 3.08–3.05 (d, 2H, piperazine protons).

IR: 1651 cm$^{-1}$ (amide carbonyl).

Example 77

Preparation of (1α,5α,6α)-6-N-(3-azabicyclo[3.1.0] hexyl-3-benzyl)-3-cyclohexyl-3-hydroxy-3-phenyl propionamide (Compound No. 77)

Step a: Preparation of 3-hydroxy-3-phenyl-3-cyclohexyl propionic acid.

This compound was synthesized following the procedure given in J. Chem. Soc. (C), 2799 (1969).

Step b: The title compound was synthesized following the method as given in Example 85, step c using 3-hydroxy-3-phenyl-3-cyclohexyl propionic acid instead of 2-hydroxy-2,2-diphenyl acetic acid.

$^1$H-NMR (CDCl$_3$); 7.37–7.16 (m, 10H, arom.); 5.7 (s, broad, NH), 5.0 (s, 1H, —OH), 3.48 (s, 2H, benzylic protons), 2.96–2.93 (m, 2H, piperazine protons), 2.73(m, 2H, piperazine protones), 2.52–2.48 (m, 2H, —CH$_2$—, α to carbonyl).

IR (DCM): 1625 cm$^{-1}$ (amide carbonyl).

Example 78

Preparation of 2-Amino-((1α,5α,6α)-6-N-(3-azabicyclo[3.1.0]hexyl-3-benzyl) acetamido)-3-cyclohexyl-3-hydroxy-3-phenyl propionamide (Compound No. 78)

This compound was synthesized following the procedure as described in Example 75, but using 3-hydroxy-3-phenyl-3-cyclohexyl-propionic acid in step b instead of 2-hydroxy-2-cyclohexyl-2-phenyl acetic acid.

$^1$H-NMR(CDCl$_3$,) 7.36–7.17 (m, 10H, arom.), δ 3.66–3.5 (m, 4H, benzylic protons, N—CH$_2$—CO)

IR: 1654 cm$^{-1}$ (broad amide carbonyl)

Example 79

Preparation of 2-Amino-((1α,5α,6α)-6-N-(3-azabicyclo[3.1.0]hexyl-3-benzyl) propionamido)-2-cyclohexyl-3-hydroxy-3-phenyl propionamide (Compound No. 79)

This compound was synthesized following the procedure as described in Example 74, but using 3-hydroxy-3-phenyl-3-cyclohexyl-propionic acid in step b instead of 2-hydroxy-2-cyclohexyl-2-phenyl acetic acid.

$^1$H-NMR(CDCl$_3$) 7.5–7.15 (m, 10H, arom.), δ 4.15 (m, 1H, CH) δ 3.57 (s, 2H, benzylic)

IR: 1664 cm$^{-1}$ (broad, amide carbonyl)

Example 80

Preparation of (1α,5α,6α)-2-[6-N-(3-azabicyclo [3.1.0]hexyl-3-benzyl)-N-propionamido-2-cyclohexyl-2-hydroxy-2-phenyl acetate. (Compound No. 80)

Step a: Preparation of 1-chloro-(1α,5α,6α)-2-[6-N-(3-azabicyclo[3.1.0]hexyl-3-benzyl-)-N-propionamide: Equimolar quantities of 2-chloropropionyl chloride and (1α,5α,6α)-3-N-benzyl-6-amino-3-azabicyclo[3.1.0]hexane were reacted in dichloromethane in the presence of triethylamine. The reaction mixture was worked up by the addition of water and the compound was isolated from the organic phase.

Step b: Compound No. 80 was prepared by the reaction of the compound obtained in step—a with 2-hydroxy-2-cyclohexyl-2-phenyl acetic acid, following the procedure given in step b of Example 10.

$^1$H-NMR (CDCl$_3$); 7.7–7.2 (m, 10H, arom.); 5.19 (m, 1H, ester —CH), 3.5 (s, 2H, benzylic protons), 2.95(m, 3H, piperazine protons, α-H), 2.27(q, 2H, piperazine protons), 1.68 (m, 5H), 1.5 (d, 3H, α-CH$_3$), 1.2 (m, 7H)

IR (DCM): 1669 cm$^{-1}$ (amide carbonyl), 1733 cm$^{-1}$ (ester carbonyl)

Example 81

Preparation of (2R)-(1α,5α,6α)-6-N-(3-azabicyclo[3.1.0]hexyl-3-(4-methyl-3-pentenyl))-2-cyclopentyl-2-hydroxy-2-phenyl acetamide (Compound No. 81)

Step a: Preparation of (2R)-2-hydroxy-2-cyclopentyl-2-phenyl acetic acid: Synthesized as per reported procedure of Paul T. Grover, et. al. J. Org. Chem. 2000, 65, 6283–6287.

Step b: The amide was synthesized following the procedure as described in step c of Example 85 using (2R)-2-hydroxy-2-cyclopentyl-2-phenyl acetic acid instead of 2-hydroxy-2,2-diphenyl acetic acid.

Step c: The title compound was synthesized starting from the compound obtained in step b, which was debenzylated following the method as described in step a of Example 23, and then N-alkylated as given in Example 41.

$^1$H-NMR(CDCl$_3$) 7.58–7.23 (m,5H, aromatic), 6.34 (s, 1H), 5.05 (m, 1H, vinylic) 3.11 to 3.08 (m, 2H, N—CH$_2$) 2.98 (m, 1H, α-hydrogen, 2.96 (s, 1H), 2.35 to 2.3 ( m, 4H, piperazine protons) 2.09 to 1.17 (m, 16H, aliphatic, 2xCH$_3$, cyclopentyl), 0.88 (m, 2H, cyclopropyl)

I.R.(DCM): 1652 cm$^{-1}$

Example 82

Preparation of (2R)-(1α,5α,6α)-6-N-(3-azabicyclo[3.1.0]hexyl-3-(3,4-methylenedioxyphenyl)ethyl)-2-cyclopentyl-2-hydroxy-2-phenyl acetamide (Compound No. 82)

Step a: Preparation of (2R)-2-hydroxy-2-cyclopentyl-2-phenyl acetic acid: Synthesized as per reported procedure of Paul T. Grover, et. al. J. Org. Chem. 2000, 65, 6283–6287.

Step b: The amide was synthesized following the procedure as described in step c of Example 85 using (2R)-2-hydroxy-2-cyclopentyl-2-phenyl acetic acid instead of 2-hydroxy-2,2-diphenyl acetic acid.

Step c: The title compound was synthesized starting from the compound as synthesized in step b, which was debenzylated following the method as described in step a of Example 23, and then N-alkylated as given in Example 29.

$^1$H-NMR(CDCl$_3$) 7.59–6.54 (m, 8H, arom.), 5.9 (s, 2H, methylenedioxy) 3.18 (t, 2H, N—CH$_2$—C), 3.0 (m, 1H), 2.68 (s, 1H), 2.5 (m, 3H, piperazine, α-hydrogen), 2.38–2.34 (m, 2H, piperazine), 2.17 (m, 12H, aliphatic)

IR (DCM): 1653 cm$^{-1}$ (amide carbonyl)

Example 83

Preparation of (2R)-(1α,5α,6α)-6-N-(3-azabicyclo [3.1.0]hexyl-3-(4-methyl-3-pentenyl))-2-cyclopentyl-2-hydroxy-2-phenyl acetamide succinate salt. (Compound No. 83)

(2R)-(1α,5α,6α)-6-N-(3-azabicyclo[3.1.0]hexyl-3-(4-methyl-3-pentenyl))-2-cyclopentyl-2-hydroxy-2-phenyl acetamide (Compound No 81, 1 mmol) was dissolved in ethanol (10 ml) and a solution of succinic acid (1 mmol) in ethanol (5 ml) was added and stirred at 60° C. for 1 hr. The reaction mixture was then concentrated by the evaporation of solvents under reduced pressure and the resulting solid was triturated from diethyl ether to afford the title compound.

m.p. 148–150° C., $[\alpha]_D^{25° C.}$=+17.77°

CHN analysis: C=66.77 (67.176), H=8.09 (8.05), N=6.02 (5.59).

Example 84

Preparation of (2R)-(1α,5α,6α)-6-N-(3-azabicyclo [3.1.0]hexyl-3-(4-methyl-3-pentenyl))-2-cyclopentyl-2-hydroxy-2-phenyl acetamide L-(+)-tartarate salt. (Compound No. 84)

(2R)-(1α,5α,6α)-6-N-(3-azabicyclo[3.1.0]hexyl-3-(4-methyl-3-pentenyl))-2-cyclopentyl-2-hydroxy-2-phenyl acetamide (Compound No. 81, 1 mmol) was dissolved in ethanol (10 ml) and a solution of L-(+)-tartaric acid (1 mmol) in ethanol (5 ml) was added and stirred at 60° C. for 1 hr. The reaction mixture was then concentrated by the evaporation of solvents under reduced pressure and the resulting solid was triturated from diethyl ether to afford the title compound.

m.p. 49° C.

Example 85

Preparation of (1α,5α,6α)-6-N-(3-azabicyclo[3.1.0] hexyl)-2-cyclohexyl-2-hydroxy-2-phenylacetamide (Compound No. 85)

Step a: Synthesis of 2-hydroxy-2-cyclohexyl-2-phenylacetic acid.

The title compound was prepared following the procedure as described in J. Amer. Chem. Soc., 75, 2654 (1953).

Step b: Synthesis of (1α,5α,6α)-6-N-(3-azabicyclo[3.1.0]hexyl-3-benzyl)-2-cyclohexyl-2-hydroxy-2-phenylacetamide To a solution of (1α,5α,6α)-3N-benzyl-6-amino3-azabicyclo-[3.1.0]hexane, as per reported procedure of Braish, T. F. et al. Syn Lett. 1100 (1996). (1 mmol, 0.188 gm) in DMF (5 ml) was added 2-hydroxy-2,2-diphenyl acetic acid (1 mmol, 0.225 gm) and cooled to 0° C. The reaction mixture was treated with hydroxy benzotriazole (1 mmol, 0.135 g) followed by N-methyl morpholine (2 mmol, 0.202 gm) and stirred at 0° C. for 0.5 hours. Then was added EDC (1-[3-(dimethylamino)propyl]-3-ethyl carbodiimide hydrochloride, (1 mmol, 0.192 gms).

The reaction mixture after stirring at 0° C. for 1 hr. was later stirred at room temperature overnight. Then the RM was poured into cold water and extracted with ethyl acetate. The combined organic layer were washed with water and dried over sodium sulphate. The crude compound obtained after removing the solvent was purified by column chromatography (silicagel 100–200 mesh), eluting the compound with 30–70 ethylacetate-hexane mixture.

Step c: Synthesis of (1α,5α,6α)-6-N-(3-azabicyclo[3.1.0] hexyl)-2-cyclohexyl-2-hydroxy-2-phenylacetamide To a solution of the compound of step b (0.3 g, 0.74 mmol) in methanol (10.0 ml), 10% Pd—C (0.3 g) was added and the reaction mixture was stirred at room temperature for 2 hours under an atmosphere of $H_2$. The reaction mixture was filtered through a bed of hyflo and the bed was washed with methanol (10.0 ml). The filtrate was concentrated under vacuum to give the title compound in 77% (0.18 g, 0.57 mmol) yield.

$^1$HNMR (CDCl$_3$): δ 7.60 (d, J=6 Hz, 2H), 7.24–7.37 (m, 3H), 6.63 (brd, 1(m, 2H), 2.34–2.44 (m, 3H), 1.19–1.39 (m, 10H), 1.02 (d, J=6 Hz, 2H), 0.96 (m, 1H)

IR (KBr): 1665.6 cm$^{-1}$

Example 86

Preparation of (1α,5α,6α)-6-N-(3-azabicyclo-[3.1.0] hexyl)-2-cyclohexyl-2-hydroxy-2-(4-Fluorophenyl) acetamide (Compound No. 86)

Step a: Synthesis of 2-(4-fluorophenyl)-2-cyclohexyl-2-hydroxy acetic acid.

The compound was synthesized as per reported procedure in Syn. Comm., 11 (12), 943–946 (1981).

Step b: Synthesis of (1α,5α,6α)-6-N-(3-azabicyclo-[3.1.0] hexyl-3-benzyl)-2-cyclohexyl-2-hydroxy-2-(4-fluorophenyl)acetamide This was synthesized in direct analogy to the procedure of step b of Example 85, using the product of step a here instead of that of Example 85.

Step c: Synthesis of (1α,5α,6α)-6-N-(3-azabicyclo-[3.1.0] hexyl)-2-cyclohexyl-2-hydroxy-2-phenylacetamide This compound was prepared in 90% yield following a procedure directly analogous to that of step c, Example 85.

IR (KBr): 1663.9 cm$^{-1}$

Example 87

Preparation of (1α,5α,6α)-6-N-(3-azabicyclo-[3.1.0] hexyl)-2-cyclohexyl-2-hydroxy-2-(4-methyoxyphenyl)acetamide (Compound No. 87)

Step a: Synthesis of 2-(4-methoxyphenyl)-2-cyclohexyl-2-hydroxy acetic acid

This compound was synthesized as per reported procedure in Syn. Comm. 11 (12), 943–946 (1981).

Step b: Synthesis of (1α,5α,6α)-6-N-(3-azabicyclo-[3.1.0] hexyl-3-benzyl)-2-cyclohexyl-2-hydroxy-2-(4-methoxyphenyl)acetamide This was synthesized in direct analogy to the procedure of step b of Example 85, using the product of step a here instead of that of Example 85.

Step c: Synthesis of (1α,5α,6α)-6-N-(3-azabicyclo-[3.1.0] hexyl)-2-cyclohexyl-2-hydroxy-2-(4-methyloxyphenyl) acetamide This compound was prepared in 90% yield by following a procedure directly analogous to that of step c, Example 85.

$^1$H NMR (CDCl$_3$): δ 7.52–7.58 (m, 2H), 6.82–6.90 (m, 3H), 3.72 (s, 3H), 3.16–3.32 (m, 1H), 2.60–2.84 (m, 2H), 2.06–2.38 (m, 2H), 1.57–1.77 (m, 5H), 1.17–1.37 (m, 7H), 0.92–0.96 (m, 1H)

IR (KBr): 1659.3 cm$^{-1}$

Example 88

Preparation of (1α,5α,6α)-6-N-(3-azabicyclo-[3.1.0] hexyl)-2-cyclohexyl-2-hydroxy-2-(4-methylphenyl) acetamide (Compound No. 88)

Step a: Synthesis of 2-(4-methylphenyl)-2-cyclohexyl-2-hydroxy acetic acid.

This compound was synthesized as per reported procedure in *Syn. Comm.*, 11 (12), 943–946 (1981)

Step b: Synthesis of (1α,5α,6α)-6-N-(3-azabicyclo-[3.1.0] hexyl-3-benzyl)-2-cyclohexyl-2-hydroxy-2-(4-methylphenyl)acetamide This was synthesized in direct analogy to the procedure of step b of Example 85, using the product of step a here, instead of that of Example 85.

Step c: Synthesis of (1α,5α,6α)-6-N-(3-azabicyclo-[3.1.0] hexyl)-2-cyclohexyl-2-hydroxy-2-(4-methylphenyl)acetamide This compound was prepared in 90% yield by following a procedure directly analogous to that of step c, Example 85.

$^1$H NMR (CDCl$_3$): δ 7.46 (d, J=6 Hz, 2H), 7.11–7.18 (m, 2H), 6.96 (brs, 1H), 3.02–3.07 (m, 2H), 2.50–2.80 (m, 1H), 2.31–2.35 (m, 5H), 1.58–1.67 (m, 5H), 1.10–1.35 (m, 7H), 0.80–0.90 (m, 1H)

IR (KBr): 1660.6 cm$^{-1}$

Example 89

Preparation of (1α,5α,6α)-6-N-(3-azabicyclo-[3.1.0] hexyl)-2-cyclopentyl-2-hydroxy-2-phenylacetamide (Compound No. 89)

Step a: Synthesis of 2-hydroxy-2-cyclopentyl-2-phenyl acetic acid.

This was synthesized following the procedure in *J. Amer. Chem. Soc.*, 75, 2654 (1953)

Step b: Synthesis of (1α,5α,6α)-6-N-(3-azabicyclo-[3.1.0] hexyl-3-benzyl)-2-cyclopentyl-2-hydroxy-2-phenylacetamide This was synthesized in direct analogy to the procedure of step b of Example 85, using the product of step a here instead of that of Example 85.

Step c: Synthesis of (1α,5α,6α)-6-N-(3-azabicyclo-[3.1.0] hexyl)-2-cyclopentyl-2-hydroxy-2-phenylacetamide This compound is prepared in 90% yield following a procedure directly analogous to that of step c of Example 85.

$^1$HNMR (CDCl$_3$): δ 7.57 (d, J=6 Hz, 2H), 7.15–7.35 (m, 3H), 6.52 (brs, 1H), 2.99–3.13 (m, 3H, including —OH), 2.84–2.99 (m, 1H), 2.35–2.38 (m, 2H), 1.25–1.67 (m, 10H) 1.15–1.20 (m, 1H)

IR (DCM): 1650.9 cm$^{-1}$

Example 90

Preparation of (1α,5α,6α)-6-N-(3-azabicyclo[3.1.0] hexyl)-2-cycloheptyl-2-hydroxy-2-phenylacetamide (Compound No. 90)

Step a: Synthesis of 2-hydroxy-2-cycloheptyl-2-phenyl acetic acid.

This was synthesized following the procedure in *J. Amer. Chem. Soc.*, 75, 2654 (1953).

Step b: Synthesis of (1α,5α,6α)-6-N-(3-azabicyclo[3.1.0] hexyl-3-benzyl)-2-hydroxy-2-cycloheptyl-2-phenylacetamide This was in direct analogy to the procedure of step b of Example 85, using the product of step a here instead of that of Example 85.

Step c: Synthesis of (1α,5α,6α)-6-N-(3-azabicyclo-[3.1.0] hexyl)-2-cycloheptyl-2-hydroxy-2-phenylacetamide This compound is prepared in 90% yield following a procedure directly analogous to that of step c of Example 85.

Example 91

Preparation of (1α,5α,6α)-6-N-(3-azabicyclo[3.1.0] hexyl)-2-cyclobutyl-2-hydroxy-2-phenylacetamide (Compound No. 91)

Step a: Synthesis of 2-hydroxy-2-cyclobutyl-2-phenyl acetic acid.

This was synthesized following the procedure in *J. Amer. Chem., Soc.*, 75, 2654 (1953).

Step b: Synthesis of (1α,5α,6α)-6-N-(3-azabicyclo-[3.1.0] hexyl-3-benzyl)-2-cyclobutyl-2-hydroxy-2-phenylacetamide This was synthesized in direct analogy to the procedure of step b of Example 85, using the product of step a here instead of that of Example 85.

Step c: Synthesis of (1α,5α,6α)-6-N-(3-azabicyclo-[3.1.0] hexyl)-2-cyclobutyl-2-hydroxy-2-phenylacetamide This compound is prepared in 90% yield following a procedure directly analogous to that of step c of Example 85, using the product of step a here instead of that of Example 85.

m.p.: 150° C.

$^1$HNMR (CDCl$_3$): δ 7.46–7.49 (m, 2H), 7.29–7.36 (m, 3H), 6.31 (brs, 1H), 5.14–3.40 (m, 1H), 3.05–3.14 (m, 2H), 2.86–2.90 (m, 2H), 2.39 (s, 1H), 1.75–2.05 (m, 6H), 1.25–1.51 (m, 2H)

IR (KBr): 1669.4 cm$^{-1}$

Example 92

Preparation of (1α,5α,6α)-6-N-(3-azabicyclo-[3.1.0] hexyl)-2-cyclopropyl-2-hydroxy-2-phenylacetamide (Compound No. 92)

Step a: Synthesis of 2-hydroxy-2-cyclopropyl-2-phenyl acetic acid.

This was synthesized following the procedure in *J. Amer. Chem. Soc.*, 75, 2654 (1953).

Step b: Synthesis of (1α,5α,6α)-6-N-(3-azabicyclo-[3.1.0] hexyl-3-benzyl)-2-cyclopropyl-2-hydroxy-2-phenylacetamide This was synthesized in direct analogy to the procedure of step b of Example 85, using the product of step a here instead of that of Example 85.

Step c: Synthesis of (1α,5α,6α)-6-N-(3-azabicyclo[3.1.0] hexyl)-2-cyclopropyl-2-hydroxy-2-phenylacetamide.

This compound is prepared in 96% of yield following a procedure directly analogous to that of step c, of Example 85.

$^1$HNMR (CDCl$_3$+DMSO-d$_6$): δ 7.56–7.63 (m, 2H), 7.28–7.35 (m, 3H), 5.25 (brs, 1H), 3.03–3.14 (m, 2H), 2.85–2.90 (m, 3H), 1.66–1.75 (m, 1H), 1.55–1.56 (m, 2H), 0.38–0.56 (m, 4H)

IR (KBr): 1667.1 cm$^{-1}$

Example 93

Preparation of (1α,5α,6α)-1-[6-N-(3-azabicyclo [3.1.0]hexyl)]-N-acetamido-2-hydroxy-2-cyclohexyl-2-phenylacetate (Compound No. 93)

Step a: Preparation of 2-hydroxy-2-cyclohexyl phenyl acetic acid

This was prepared following the procedure as described in J. Amer. Chem. Soc., 75, 2654 (1953).

Step b: Preparation of (1α,5α,6α)-6N-(3-azabicyclo[3.1.0] hexyl-3-benzyl)-2-chloro acetamide To a solution of the corresponding amine synthesized following the procedure of T. F. Braish et. al., Synlett., 1996, 1100 (0.6 g, 3.2 mmol) in dichloromethane (15 ml) at −20° C., triethylamine (1.34 ml) and chloroacetyl chloride were added dropwise. The reaction mixture was stirred for 2 hrs. at −20° C. The reaction mixture was cooled to room temperature, diluted with dichloromethane (15 ml) and washed with water. The organic layer was dried over anhydrous sodium sulphate and concentrated. The residue obtained was purified by column chromatography using 40% ethylacetate-hexane as the eluent mixture to get 63.1% of the title compound.

Step c: Preparation of (1α,5α,6α)-1-[6N-(3-azabicyclo-[3.1.0]hexyl-3-benzyl)]-N-acetamido-2-cyclohexyl-2-hydroxy-2-phenylacetate To a solution of compound of step a (0.304 g, 1.3 mmol) and the compound of step b (0.23 g, 0.87 mmol) in xylene (15 ml) was added 1,8-diazabicyclo[5.4.0]undec-7-ene (DBU) (0.2 g, 1.3 mmol) and the reaction mixture was refluxed for 3 hours. The reaction mixture was directly adsorbed over silicagel and purified by column chromatography using 60% ethylacetate in hexane to get the title compound in 95% yield.

Step d: of (1α,5α,6α)-1-[6-N-(3-azabicyclo-[3.1.0]hexyl)]-N-acetamido-2-hydroxy-2-cyclohexyl-2-phenylacetate.

To a solution of the corresponding N-benzyl derivative (0.245 g, 0.53 mmol) in methanol (20.0 ml) 10% Pd—C (0.1 g, 50% wet) was added and the reaction mixture was hydrogenated at 60 PSI for 3.50 hours at room temperature. The reaction mixture was filtered through a bed of hyflo and the bed was washed with methanol. The filtrate was concentrated under vacuum to get the title compound in 91%. (0.18 g, 0.48 mmol) yield.

$^1$HNMR (CDCl$_3$): δ 7.72 (d, J=6 Hz, 2H), 7.35–7.56 (m, 3H) 4.94 (d, J=15 Hz, 1H), 4.47 (d, J=15 Hz, 1H), 5.04–3.70 (m, 2H), 2.50 (s, 1H), 2.36–2.41 (m, 2H), 1.89–1.93 (m, 1H), 1.70–1.80 (m, 2H), 1.19–1.38 (m, 10H)

IR (DCM): 1738.4, 1666.5 cm$^{-1}$

Example 94

Preparation of (1α,5α,6α)-1-[6-N-(3-azabicyclo-[3.1.0]hexyl)]-N-propionamido-2-hydroxy-2-cyclohexyl-2-phenylacetate (Compound No. 94)

This compound was synthesized in direct analogy to the procedure of Example 93 by using 2-chloropropionyl chloride in step b, Example 93 instead of chloroacetyl chloride.

$^1$HNMR (CDCl$_3$): δ 7.62–7.72 (m, 2H), 7.29–7.50 (m, 3H), 5.19–5.28 (s, 1H), 3.04–3.11 (m, 2H), 2.26–2.38 (m, 2H), 1.86–1.90 (m, 2H), 1.16–1.55 (m, 15H)

IR (KBr): 1735.2, 1663.9 cm$^{-1}$

Example 95

Preparation of (1α,5α,6α)-4-[6-N-(3-azabicyclo [3.1.0]hexyl)]-N-(tert-butyloxy carbonyl)butyl-1-[2-hydroxy-2,2-bis-(4-fluorophenyl)]acetate (Compound No. 95)

Step a: Preparation of 2-hydroxy-2,2-bis-(4-fluorophenyl) acetic acid.

(i) Preparation of 1,2-Bis(4-fluorophenyl)-2-hydroxyethanone

To a solution of commercially available 4-fluorobenzaldehyde (24.8 g, 200 mmol) in ethanol (30 ml) and sodium cyanide (2.13 g, 43.5 mmol) in water (20 ml) was added and the resulting solution was refluxed for 1 hour. The reaction mixture was cooled to 0° C. and diluted with water. The solid so separated was filtered and washed with cold water thoroughly and used as such in the next step.

(ii) Preparation of 1,2-Bis(4-fluorophenyl)-2-oxo-ethanone

To the compound obtained in the above step was added conc. nitric acid (40 ml) and the resulting solution was refluxed for 4 hours. The solution was cooled and poured onto chilled water (500 ml) under stirring and the solid so produced was filtered, washed with water and dried to give the title compound in 63% yield.

(iii) Preparation of 2-hydroxy-2,2-bis-(4-fluorophenyl) acetic acid.

To a solution of KOH (21.0 gm) in water (42.0 ml), ethanol (54.0 ml) followed by the compound obtained from the above step (25.0 g, 101 mmol) was added and the resulting solution was refluxed for 30 minutes and poured into a glass plate and left overnight at room temperature. The semisolid obtained was dissolved in water (400 ml) and washed with ethyl acetate. The pH of the aqueous layer was adjusted to acidic with 50% HCl, extracted with ethyl acetate. The ethyl acetate layer was dried over anhydrous Na$_2$SO$_4$ and concentrated to give the title compound in 45% yield (12.0 g, 45 mmol).

Step b: Preparation of 6-(N-α-bromobutyl, N-tert-butyloxy carbonyl, N-3-benzyl-3-azabicyclo[3.1.0]hexane).

A solution of 6-N-tert-butyloxy carbonyl, N-3-benzyl-3-azabicyclo[3.1.0]hexane (1 mmol) in DMF (5 ml) was added to a cold suspension of sodium hydride in DMF under nitrogen. The reaction mixture stirred at room temperature for 1 hr, cooled to 0° C. and it was added to a solution of 1,4-dibromo butane (2 mmol) in DMF. The reaction mixture was stirred at room temperature for 3 hours, and then quenched by addition of aqueous ammonium chloride solution and extracted with ethyl acetate. The combined organic layer was washed with water, brine and dried over sodium sulphate. The crude compound obtained was purified by column chromatography, eluting the compound with 25:75, ethylacetate-hexane mixture.

Step c: Preparation of (1α,5α,6α)-4-[6-N-(3-azabicyclo-[3.1.0]hexyl-3-benzyl)]-N-(tert-butyloxycarbonyl)butyl-1-[2-hydroxy-2,2-bis-(4-fluorophenyl)]acetate To a solution of the above prepared bromoderivative (0.25 g, 0.59 mmol) in toluene (20.0 ml), 1,8-diazabicyclo[5.4.0] undec-7-ene (DBU) (0.135 ml, 0.89 mmol) followed by the hydroxy acid of step a (0.312 g, 1.18 mmol) was added. The reaction mixture was refluxed for 14 hours cooled and adsorbed directly onto silica gel and purified by column chromatography using 15% ethyl acetate in hexane to give the title compound in 100% (0.36 g. 0.59 mmol) yield.

Step d: (1α,5α,6α)-4-[6-N-(3-azabicyclo-[3.1.0]hexyl)]-N-tert-butyloxy carbonyl) butyl-1-[2-hydroxy-2,2-bis-(4-fluorophenyl)]acetate To a solution of the corresponding N-benzyl derivative (0.4 g, 0.66 mmol) in methanol (20.0 ml), 10% Pd—C (0.2 g, 50% wet) was added and the resulting solution was hydrogenated at 50 p.s.i. and at room temperature for 2 hr. The reaction mixture was filtered through a bed of hyflo and the bed was washed with methanol (20.0 ml). The filtrate was concentrated to give the title compound as oil in 82% (0.28 g, 0.54 mmol) yield.

1HNMR (CDCl$_3$): δ 7.38–7.43 (m, 4H), 7.01–7.07 (m, 4H), 4.27–4.31 (m, 2H), 2.93–3.19 (m, 5H), 2.43–2.46 (m, 1H), 1.28–1.63 (m, 13H).

IR (DCM): 1731, 1685 cm$^{-1}$

Example 96

Preparation of (1α,5α,6α)-4-[6-N-(3-azabicyclo-[3.1.0]hexyl)]-N-(tert-butyloxy carbonyl)butyl-1-[2-propyloxy-2,2-bis-(4-fluorophenyl)]acetate (Compound No. 96)

Step a: Preparation of 2-propyloxy-2,2-bis-(4-fluorophenyl) acetic acid
 (i) Preparation of 2-hydroxy-2,2-bis-(4-fluorophenyl)acetic acid.
 This was synthesized as described in step a, of Example 85.
 (ii) Preparation of 2-hydroxy acetic acid 2,2-bis-(4-fluorophenyl)ethyl ester
 To a solution of the compound of the above step (50 g, 18.9 mmol) in ethanol (100.0 ml) at 0° C. thionyl chloride (5.0 ml) was added and the resulting solution was refluxed for 4 hr. Ethanol was concentrated under vacuum and the residue was purified by column chromatography using 20% ethyl acetate in hexane to give the title compound as liquid in 91% (5.08, 17.2 mmol) yield.
 (iii) Preparation of 2,2-bis-(4-fluorophenyl)-2-propoxy acetic acid ethyl ester
 To a solution of sodium hydride (0.72 g, 15.42 mmol) in DMF (1.0 ml) at 0° C., the hydroxy ester (1.5 g, 5.14 mmol) in DMF (5.0 ml) was added and stirred at ROOM TEMPERATURE for 30 minutes. The reaction mixture was cooled to 0° C. and bromo propane (0.95 g, 7.7 mmol) was added and stirred for 4 hr. at ROOM TEMPERATURE. It was diluted with water, extracted with ethyl acetate, dried and concentrated. The residue was purified by column chromatography using 10% ethyl acetate in hexane to get the title compound as a liquid in 46% (0.79 g, 2.36 mmol) yield.
 (iv) Preparation of 2-propyloxy-2,2-bis-(4-fluorophenyl) acetic acid
 To a solution of the ester (0.7 g, 2 mmol) in methanol (20.0 ml), 1N LiOH (2.0 ml) was added and the reaction mixture was stirred at ROOM TEMPERATURE for 12 hr. Methanol was concentrated under vacuum, the residue was taken in water (50.0 ml) and washed with ethyl acetate. The aqueous layer was neutralized with acetic acid and extracted with ethyl acetate, dried and concentrated under vacuum to give the title compound as an oil in 47% (0.3 g, 0.94 mmol) yield.

$^1$HNMR (CDCl$_3$): δ 7.44–7.49 (m, 4H), 7.04–7.09 (m, 4H), 4.21–4.23 (m, 2 3.34 (m, 4H), 3.05–3.11 (m, 2H), 2.33–2.72 (m, 3H), 1.32–1.69 (m, 17H), 0.97 (t, J=6 Hz, 3H),

IR (DCM): 1742.2, 1693.8 cm$^{-1}$

Step b: Preparation of 6-(N-α-bromobutyl, N-tert-butyloxy carbonyl, N-3-benzyl-3-azabicyclo[3.1.0]hexane)
 Prepared as described in step b of Example 85.

Step c: Preparation of (1α,5α,6α)-4-[6-N-(3-azabicyclo-[3.1.0]hexyl-3-benzyl)]-(tert-butyloxy carbonyl)butyl-1-[2-propyloxy-2,2-bis-(4-fluorophenyl)]acetate
 This was synthesized following the procedure of step c of Example 85 in 58% yield.

Step d: Preparation of (1α,5α,6α)-4-[6-N-(3-azabicyclo-[3.1.0]hexyl)]-N-tert-butyloxy carbonyl)butyl-1-[2-propyloxy-2,2-bis-(4-fluorophenyl)]acetate
 The title compound was prepared following the procedure of step d, Example 85 in 64% yield.

1HNMR (CDCl$_3$): δ 7.44–7.49 (m, 4H), 7.04–7.09 (m, 4H), 4.21–4.23 (m, 2H), 3.20–3.34 (m, 4H), 3.05–3.11 (m, 2H), 2.33–2.72 (m, 3H), 1.32–1.69 (m, 17H), 0.97 (t, J=6 Hz, 3H)

IR (DCM): 1742.2, 1693.8 cm$^{-1}$

Example 97

Preparation of (1α,5α,6α)-6N-(3-azabicyclo-[3.1.0] hexyl)-2,2-diphenyl acetamide (Compound No. 97)

Step a: Preparation of 2,2-diphenyl acetic acid
 Available commercially from Lancaster Synthesis (Windham, N.H.).

Step b: Preparation of (1α,5α,6α)-3N-benzyl-6-amino-3-azabicyclo-[3.1.0]hexane
 Synthesized as per reported procedure of Braish, T. F. et. al., Synlett., 1100 (1996).

Step c: Preparation of (1α,5α,6α)-6N-(3-azabicyclo-[3.1.0] hexyl-3-benzyl)-2,2-diphenyl acetamide
 This was prepared by following the procedure of step b of Example 85' in 85% yield.

Step d: Preparation of (1α,5α,6α)-6N-(3-azabicyclo-[3.1.0] hexyl)-2,2-diphenyl acetamide
 This was synthesized from the corresponding N-benzyl derivative in 72% yield by following the procedure of step c, Example 85.

1HNMR (CDCl$_3$): δ 7.24–7.30 (m, 10H), 5.62 (brs, 1H), 4.83 (s, 1H), 3.01–3.08 (m, 2H), 2.24–2.34 (m, 3H), 1.39–1.45 (m, 2H).

IR (DCM): 1650.6 cm$^{-1}$

Example 98

Preparation of (1α,5α,6α)-6N-(3-azabicyclo-[3.1.0] hexyl)-2-cyclohexyl-2-methoxy-2-phenyl acetamide (Compound No. 98)

Step a: Preparation of 2-cyclohexyl-2-phenyl-2-methoxy acetic acid
 This was prepared according to the procedure described in J. Amer. Chem., Soc., 75, 2654, 1953.

Step b: Preparation of (1α,5α,6α)-3N-benzyl-6-amino-3-azabicyclo-[3.1.0]hexane
 Synthesized as per reported procedure of Braish, T. F. et. al., Synlett., 1100 (1996).

Step c: Preparation of (1α,5α,6α)-6N-(3-azabicyclo-[3.1.0] hexyl-3-benzyl)-2-cyclohexyl-2-methoxy-2-phenyl acetamide
 This was prepared in 40% yield by following the procedure of step b, Example 85.

Step d: Preparation of (1α,5α,6α)-6N-(3-azabicyclo-[3.1.0] hexyl)-2-cyclohexyl-2-methoxy-2-phenyl acetamide This was synthesized from the corresponding N-benzyl derivative by following the procedure of step c, Example 85 in 64% yield.

1H NMR (CDCl$_3$): δ 7.27–7.41 (m, 5H), 6.76 (brs, 1H), 3.21 (d, J=12 Hz, 2H), 3.09 (s, 3H), 2.97 (d, J=12 Hz, 2H), 2.54 (s, 1H), 2.31 (t, J=12 Hz, 1H), 1.96–2.03 (m, 5H), 1.68–1.79 (m, 5H), 1.68–1.79 (m, 2H)

IR (DCM): 1660.7 cm$^{-1}$

Biological Activity

Radioligand Binding Assays:

The affinity of test compounds for M$_2$ and M$_3$ muscarinic receptor subtypes was determined by [$^3$H]-N-methylscopolamine binding studies using rat heart and submandibular gland respectively as described by Moriya et al., (*Life Sci,* 1999, 64(25):2351–2358) with minor modifications.

Membrane preparation: Submandibular glands and heart were isolated and placed in ice cold homogenising buffer (HEPES 20 mM, 10 mM EDTA, pH 7.4) immediately after sacrifice. The tissues were homogenised in 10 volumes of homogenising buffer and the homogenate was filtered through two layers of wet gauze and filtrate was centrifuged at 500 g for 10 min. The supernatant was subsequently centrifuged at 40,000 g for 20 min. The pellet thus obtained was resuspended in same volume of assay buffer (HEPES 20 mM, EDTA 5 mM, pH 7.4) and were stored at −70° C. until the time of assay.

Ligand binding assay: The compounds were dissolved and diluted in DMSO. The membrane homogenates (150–250 μg protein) were incubated in 250 μl of assay buffer (HEPES 20 mM, pH 7.4) at 24–25° C. for 3 h. Non-specific binding was determined in the presence of 1 μM atropine. The incubation was terminated by vaccum filtration over GF/B fiber filters (Wallac). The filters were then washed with ice cold 50 mM Tris HCl buffer (pH 7.4). The filter mats were dried and bound radioactivity retained on filters was counted. The IC$_{50}$ & Kd were estimated by using the non-linear curve fitting program using G Pad Prism software. The value of inhibition constant Ki was calculated from competitive binding studies by using Cheng & Prusoff equation (*Biochem Pharmacol,* 1973, 22: 3099–3108), Ki=IC$_{50}$/(1+L/Kd), where L is the concentration of [$^3$H]NMS used in the particular experiment.

Functional Experiments Using Isolated Rat Bladder:

Methodology:

Animals were euthanized by overdose of urethane and whole bladder was isolated and removed rapidly and placed in ice cold Tyrode buffer with the following composition (mMol/L) NaCl 137; KCl 2.7; CaCl$_2$ 1.8; MgCl$_2$ 0.1; NaHCO$_3$ 11.9; NaH$_2$PO$_4$ 0.4; Glucose 5.55 and continuously gassed with 95% O$_2$ and 5% CO$_2$.

The bladder was cut into longitudinal strips (3 mm wide and 5–6 mm long) and mounted in 10 ml organ baths at 30° C., with one end connected to the base of the tissue holder and the other end connected to a polygraph through a force displacement transducer. Each tissue was maintained at a constant basal tension of 2 g and allowed to equilibrate for 1 hour during which the PSS was changed every 15 min. At the end of equilibration period, the stabilization of the tissue contractile response was assessed with 1 μMol/L of Carbachol consecutively for 2–3 times. Subsequently, a cumulative concentration response curve to carbachol (10$^{-9}$ mol/L to 3×10$^{-5}$ mol/L) was obtained. After several washes, once the baseline was achieved, cumulative concentration response curve was obtained in the presence of NCE (NCE added 20 min. prior to the second CRC).

The contractile results were expressed as % of control E max. ED50 values were calculated by fitting a non-linear regression curve (Graph Pad Prism). pKB values were calculated by the formula pKB=−log[(molar concentration of antagonist/(dose ratio−1))]

where, dose ratio=ED50 in the presence of antagonist/ED50 in the absence of antagonist.

The results are listed in Tables II, III and IV.

In-Vitro Tests

TABLE II

| | Receptor Binding Assay Ki (nM) | | | Functional |
|---|---|---|---|---|
| | M$_2$ | M$_3$ | Selectivity | Assay K$_B$ (nM) |
| Compound No. 22 | 2263 | 94 | 24.07 | 27.5 |
| Compound No. 41 | 2944 | 47 | 62.64 | 32.35 |
| Compound No. 65 | 1370 | 33 | 41.52 | 4.0 |
| Compound No. 66 | 237 | 18.4 | 12.88 | 5.0 |
| Compound No. 81 | 564 | 12.4 | 45.48 | 7.95 |
| Compound No. 82 | 645.7 | 11.74 | 5 | 9.12 |
| Tolterodine | 6.91 | 7.07 | 0.98 | 2.0 |
| Oxybutynin | 6.97 | 0.95 | 7.34 | 2.0 |
| Atropine | 0.5 | 0.6 | 0.83 | |

TABLE III

| Compound No. | M$_3$ | | M$_2$ | | Rat Bladder |
|---|---|---|---|---|---|
| | Ki (nm) | Pki | Ki (nm) | pKi | pK$_B$ |
| 22 | 94 | 7.03 | 2263 | 5.65 | 7.57 |
| 23 | 530 | 6.28 | >1000 | <6 | 5.64 |
| 24 | 490 | 6.31 | >1000 | <6 | 5.42 |
| 25 | 1700 | 5.77 | >1000 | <6 | 6.54 |
| 28 | 150 | 6.82 | >1000 | <6 | ND |
| 29 | 97 | 7.01 | >1000 | <6 | ND |
| 30 | 833 | 6.08 | >0000 | <5 | ND |
| 31 | 233 | 6.63 | 1592 | 5.8 | ND |
| 35 | 429 | 6.37 | 1179 | <6 | 7.61 |
| 38 | 1560 | 5.81 | >1000 | <6 | 6.54 |
| 41 | 47 | 7.33 | 2944 | 5.53 | 7.69 |
| 42 | 55 | 7.25 | 2197 | 5.66 | 7.12 |
| 49 | 1000 | 6.00 | >1000 | <6 | 6.2 |
| 50 | 1200 | 5.92 | >1000 | <6 | 6.86 |
| 52 | 370 | 6.43 | >1000 | <6 | 5.51 |
| 55 | 380 | 6.42 | >1000 | <6 | ND |
| 57 | 240 | 6.62 | >1000 | <6 | 5.73 |
| 64 | 68 | 7.2 | 2995 | 5.6 | 7.56 |
| 65 | 33 | 7.53 | 1370 | 5.87 | 8.4 |
| 66 | 18.43 | 7.81 | 181.8 | 6.94 | 8.49 |
| 67 | 39 | 7.41 | 1424 | 5.85 | 7.42 |
| 68 | 108 | 6.97 | >1000 | <6 | ND |
| 69 | 1416 | 5.85 | >10000 | <5 | ND |
| 70 | 750 | 6.12 | >10000 | <5 | ND |
| 72 | 21 | 7.68 | 1531 | 5.82 | 7.18 |
| 81 | 12.4 | 7.94 | 564 | 6.28 | 7.95 |
| 82 | 11.74 | 7.93 | 645.7 | 6.19 | 9.12 |
| Tolterodine | 7.07 | 8.15 | 6.91 | 8.16 | 2.0 |
| Altropine | 0.6 | 9.6 | 0.5 | 9 | — |

TABLE IV

| Compound No. | Receptor Binding Assay (pKi) | |
|---|---|---|
| | $M_2$ | $M_3$ |
| 85 | <6 | <6 |
| 86 | <6 | <6 |
| 87 | <6 | <6 |
| 88 | <6 | <6 |
| 89 | <6 | <6 |
| 90 | <6 | 6.44 |
| 91 | 4 | 5.56 |
| 92 | <5 | <5 |
| 93 | <6 | <6 |
| 94 | <6 | <6 |
| 95 | <6 | <6 |
| 96 | <6 | <6 |
| 97 | <6 | <6 |
| 98 | <6 | <6 |
| Tolterodine | 8.30 | 8.18 |

While the present invention has been described in terms of its specific embodiments, certain modifications and equivalents will be apparent to those skilled in the art and are intended to be included within the scope of the present invention.

We claim:

1. A compound having the structure of Formula I:

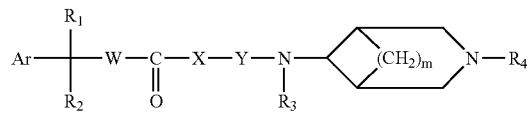

Formula I and its pharmaceutically acceptable salts, pharmaceutically acceptable solvates, esters, enantioners, diastereomers, or N-oxides, wherein Ar represents an aryl or a heteroaryl ring having 1–2 hetero atoms selected from the group consisting of oxygen, sulphur and nitrogen atoms, the aryl or heteroaryl rings may be unsubstituted or substituted by one to three substituents independently selected from straight or branched lower alkyl ($C_1$–$C_4$), trifluoromethyl, methylenedioxy, cyano, hydroxy, halogen (e.g. F, Cl, Br, I), nitro, lower alkoxy ($C_1$–$C_4$), aryloxy, amino or lower alkylamino;

$R_1$ represents $C_3$–$C_9$ cycloalkyl ring, a $C_3$–$C_9$ cyclo alkenyl ring, an aryl or a heteroaryl ring having 1 to 2 hetero atoms selected from the group consisting of oxygen, sulphur and nitrogen atoms, the aryl or a heteroaryl ring may be unsubstituted or substituted by one to three substituents independently selected from lower alkyl ($C_1$–$C_4$), trifluoromethyl, cyano, hydroxy, nitro, lower alkoxycarbonyl, halogen, lower alkoxy ($C_1$–$C_4$), unsubstituted amino or lower alkyl ($C_1$–$C_4$) amino;

$R_2$ represents a hydrogen, hydroxy, amino, alkoxy, alkenyloxy, alkynyloxy, carbamoyl or halogen (e.g. F, Cl, Br, I);

W represents $(CH_2)_p$, where p represents 0 to 1;

X represents an oxygen, sulphur, NR, or no atom, where R is H or lower alkyl ($C_1$–$C_4$);

Y represents $(CHR_5)q$ CO wherein $R_5$ represents hydrogen or methyl; or y represents $(CH_2)q$ wherein q represents 0 to 4;

m represents 0 to 2;

$R_3$ represents hydrogen, lower alkyl or $CO_2C(CH_3)_3$;

$R_4$ represents hydrogen, $C_1$–$C_{15}$ saturated or unsaturated aliphatic hydrocarbon groups in which any 1 to 6 hydrogen atoms may be substituted with the group independently selected from halogen, arylalkyl, arylalkenyl, heteroarylalkyl or heteroarylalkenyl having 1 to 2 hetero atoms selected from the group consisting of nitrogen, oxygen and sulphur atoms with an option that any 1 to 3 hydrogen atoms on an aryl or heteroaryl ring in said arylalkyl, arylalkenyl, hetero arylalkenyl group may be substituted with lower alkyl, trifluoromethyl, cyano, hydroxyl, carboxylic acid, nitro, lower alkoxycarbonyl, halogen, lower alkoxy, amino, lower alkylamino, loweralkyl carbonyl amino, loweralkyl thiocarbonyl amino or loweralkyl carbonyl amino sulphonyl and pharmaceutically acceptable salts thereof.

2. The compound according to claim 1 having the structure of Formula II

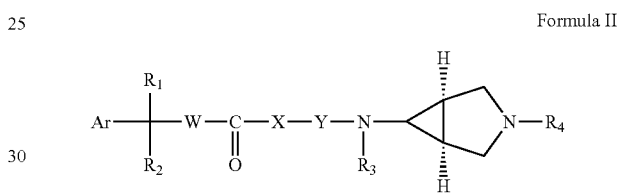

Formula II and its pharmaceutically acceptable salts, pharmaceutically acceptable solvates, esters, enantiomers, diastereomers, N-oxides, polymorphs, prodrugs, metabolites, wherein Ar, $R_1$, $R_2$, $R_3$, $R_4$, W, X and Y are as defined for Formula I.

3. The compound according to claim 1 having the structure of Formula III

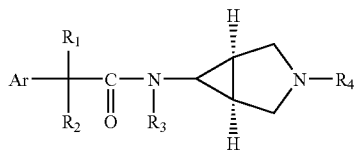

Formula III and its pharmaceutically acceptable salts, pharmaceutically acceptable solvates, esters, enantioners, diastereomers, N-oxides, polymorphs, prodrugs, or metabolites, wherein Ar, $R_1$, $R_2$, $R_3$, and $R_4$ are as defined for Formula I.

4. The compound according to claim 1 having the structure of Formula IV

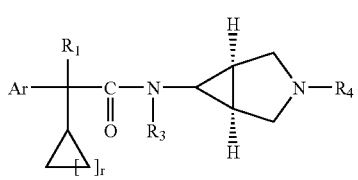

Formula IV and its pharmaceutically acceptable salts, pharmaceutically acceptable solvates, esters, enantiomers, diastereomers, N-oxides, polymorphs, prodrugs, metabolites, wherein Ar, $R_1$, $R_3$, and $R_4$, are as defined for Formula I and r is 1 to 4.

5. A Compound according to claim 1 having the structure of Formula V

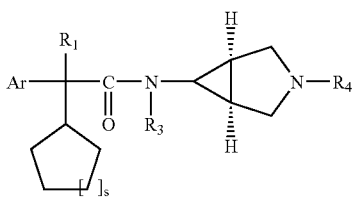

Formula V and its pharmaceutically acceptable salts, pharmaceutically acceptable solvates, esters, enantiomers, diastereomers, N-oxides, polymorphs, prodrugs, metabolites, wherein Ar, $R_1$, $R_3$ and $R_4$ are as defined for Formula I and s is 1 to 3.

6. The compound according to claim 5 having the structure of Formula VI

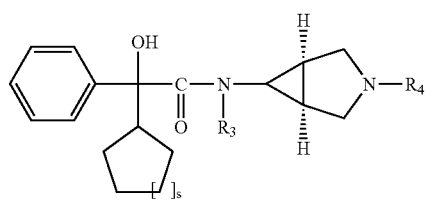

Formula VI and its pharmaceutically acceptable salts, pharmaceutically acceptable solvates, esters, enantiomers, diastereomers, N-oxides, polymorphs, prodrugs, metabolites wherein $R_3$, $R_4$ and s are as defined for Formula V.

7. A compound selected from the group consisting of:
(1α,5α,6α)-6-N-(3-azabicyclo[3.1.0]hexyl-3-benzyl)-2-hydroxy-2,2-diphenyl acetamide (Compound No. 1),
(1α,5α,6α)-6-N-(3-azabicyclo[3.1.0]hexyl-3-benzyl)-2-hydroxy-2,2-di(4-fluoro phenyl)acetamide (Compound No. 2),
(1α,5α,6α)-6-N-(3-azabicyclo[3.1.0]hexyl-3-benzyl)-2-(2-propenyloxy)-2,2-diphenyl acetamide (Compound No. 3),
(1α,5α,6α)-6-N-(3-azabicyclo[3.1.0]hexyl-3-benzyl)-2-(2-propenyloxy)-2,2-di(4-fluorophenyl)acetamide (Compound No. 4),
(1α,5α,6α)-6-N-(3-azabicyclo[3.1.0]hexyl-3-benzyl)-2-propyloxy-2,2-diphenyl acetamide (Compound No. 5),
(1α,5α,6α)-6-N-(3-azabicyclo[3.1.0]hexyl-3-benzyl)-2-propyloxy-2,2-di(4-fluoro phenyl)acetamide (Compound No. 6),
(1α,5α,6α)-6-N-(3-azabicyclo[3.1.0]hexyl-3-benzyl)-2-(2-propynyloxy)-2,2-diphenyl acetamide (Compound No. 7),
(1α,5α,6α)-6-N-(3-azabicyclo[3.1.0]hexyl-3-benzyl)-2-hydroxy-2,2-di(2-furyl) acetamide (Compound No. 8),
(1α,5α,6α)-6-N-(3-azabicyclo[3.1.0]hexyl-3-benzyl)-2-hydroxy-2,2-di(2-thienyl) acetamide (Compound No. 9),
(1α,5α,6α)-4-(6-N-(3-azabicyclo[3.1.0]hexyl-3-benzyl))-N-tert-butyloxycarbonyl) butyl-1-(2-hydroxy-2,2-diphenyl)acetate (Compound No. 10),
(1α,5α,6α)-3-(6-N-(3-azabicyclo[3.1.0]hexyl-3-benzyl))-N-tertbutyloxycarbonyl)propyl-1-(2-hydroxy-2,2-diphenyl)acetate (Compound No. 11),
(1α,5α,6α)-3-(6-N-(3-azabicyclo[3.1.0]hexyl-3-benzyl))-N-tert-butyloxycarbonyl) propyl-1-(2-propyloxy-2,2-diphenyl)acetate (Compound No. 12),
(1α,5α,6α)-4-(6-N-(3-azabicyclo[3.1.0]hexyl-3-benzyl))-N-tert-butyloxycarbonyl) butyl-1-(2-propyloxy-2,2-diphenyl)acetate (Compound No. 13),
(1α,5α,6α)-4-(6-N-(3-azabicyclo[3.1.0]hexyl-3-benzyl))-N-tert-butyloxycarbonyl) butyl-1-(2-(2-propenyloxy)-2,2-diphenyl)acetate (Compound No. 14),
(1α,5α,6α)-4-(6-N-(3-azabicyclo[3.1.0]hexyl-3-benzyl))-N-tert-butyloxycarbonyl) butyl-1-(2-hydroxy-2,2-di(4-fluorophenyl))acetate (Compound No. 15),
(1α,5α,6α)-4-(6-N-(3-azabicyclo[3.1.0]hexyl-3-benzyl))-N-tert-butyloxycarbonyl) butyl-1-(2-propyloxy-2,2-di(4-fluorophenyl))acetate (Compound No. 16),
(1α,5α,6α)-1-(6-N-(3-azabicyclo[3.1.0]hexyl-3-benzyl))-N-acetamido-2-(2-propyloxy)-2,2-diphenyl acetate (Compound No. 17),
(1α,5α,6α)-1-(6-N-(3-azabicyclo[3.1.0]hexyl-3-benzyl))-N-acetamido-2-(2-propenyloxy)-2,2-diphenyl acetate (Compound No. 18),
(1α,5α,6α)-1-(6-N-(3-azabicyclo[3.1.0]hexyl-3-benzyl))-N-propionamido-2-(2-propenyloxy)-2,2-diphenyl acetate (Compound No. 19),
(1α,5α,6α)-1-(6-N-(3-azabicyclo[3.1.0]hexyl-3-benzyl))-N-propionamido-2-2-propyloxy)-2,2-diphenyl acetate (Compound No. 20),
(1α,5α,6α)-6-N-(3-azabicyclo[3.1.0]hexyl-3-benzyl))-N-acetamido-2-hydroxy-2,2-di(4-fluorophenyl)acetate (Compound No. 21),
(1α,5α,6α)-6-N-(3-azabicyclo[3.1.0]hexyl-3-benzyl)-2-cyclohexyl-2-hydroxy-2-phenyl acetamide (Compound No. 22),
(1α,5α,6α)-6-N-(3-azabicyclo[3.1.0]hexyl-3-(3,5-difluorobenzyl))-2-cyclohexyl -2-hydroxy-2-phenyl acetamide (Compound No. 23),
(1α,5α,6α)-6-N-(3-azabicyclo[3.1.0]hexyl-3-(4-bromobenzyl))-2-cyclohexyl-2-hydroxy-2-phenyl acetamide (Compound No. 24),
(1α,5α,6α)-6-N-(3-azabicyclo[3.1.0]hexyl-3-(2,6-difluorobenzyl))-2-cyclohexyl -2-hydroxy-2-phenyl acetamide (Compound No. 25),
(1α,5α,6α)-6-N-(3-azabicyclo[3.1.0]hexyl-3-(2-phenylbenzyl))-2-cyclohexyl-2-hydroxy-2-phenyl acetamide (Compound No. 26),
(1α,5α,6α)-6-N-(3-azabicyclo[3.1.0]hexyl-3-(2-phenylethyl))-2-cyclohexyl-2-hydroxy-2-phenyl acetamide (Compound No. 27),
(1α,5α,6α)-6-N-(3-azabicyclo[3.1.0]hexyl-3-(2-(2,3-dihydrobenzofuran-5-yl) ethy))-2-cyclohexyl-2-hydroxy-2-phenyl acetamide (Compound No. 28),
(1α,5α,6α)-6-N-(3-azabicyclo[3.1.0]hexyl-3-(2-(3,4-methylenedioxyphenyl) ethyl))-2-cyclohexyl-2-hydroxy-2-phenyl acetamide (Compound No. 29),
(1α,5α,6α)-6-N-(3-azabicyclo[3.1.0]hexyl-3-(1-(2,3-dihydrobenzofuran-5-yl) acetyl))-2-cyclohexyl-2-hydroxy-2-phenyl acetamide (Compound No. 30),
(1α,5α,6α)-6-N-(3-azabicyclo[3.1.0]hexyl-3-(2-(benzofuran-5-yl)ethyl))-2-cyclohexyl-2-hydroxy-2-phenyl acetamide (Compound No. 31),
(1α,5α,6α)-6-N-(3-azabicyclo[3.1.0]hexyl-3-methyl)-2-cyclohexyl-2-hydroxy-2-phenyl acetamide (Compound No. 32), (1α,5α,6α)-6-N-(3-azabicyclo[3.1.0]hexyl-3-ethyl)-2-cyclohexyl-2-hydroxy-2-phenyl acetamide (Compound No. 33), (1α,5α,6α)-6-N-(3-azabicyclo[3.1.0]hexyl-3-(1-propyl))-2-cyclohexyl-2-hydroxy-2-phenyl acetamide (Compound No. 34), (1α,5α,6α)-6-N-(3-azabicyclo[3.1.0]hexyl-3-(2-propargyl))-2-cyclohexyl-2-hydroxy-2-phenyl acetamide (Compound No. 35), (1α,5α,6α)-6-N-(3-azabicyclo[3.1.0]hexyl-3-(2-propenyl))-2-cyclohexyl-2-hydroxy-2-phenyl acetamide (Compound No. 36), (1α,5α,6α)-6-N-(3-azabicyclo[3.1.0]hexyl-3-(2-propyl))-2-cyclohexyl-2-hydroxy-2-phenyl acetamide (Compound No. 37), (1α,5α,6α)-6-N-(3-azabicyclo[3.1.0]hexyl-3-cyclopropyl)-2-cyclohexyl-2-hydroxy-2-phenyl acetamide (Compound No. 38), (1α,5α,6α)-6-N-(3-azabicyclo[3.1.0]hexyl-3-(1-butyl))-2-cyclohexyl-2-hydroxy -2-phenyl acetamide (Compound No. 39), (1α,5α,6α)-6-N-(3-azabicyclo[3.1.0]hexyl-3-(3-methyl-2-butenyl))-2-cyclohexyl -2-hydroxy-2-phenyl acetamide (Compound No. 40), (1α,5α,6α)-6-N-(3-azabicyclo[3.1.0]hexyl-3-(4-methyl-3-pentenyl))-2-cyclohexyl-2-hydroxy-2-phenyl acetamide (Compound No. 41), (1α,5α,6α)-6-N-(3-azabicyclo[3.1.0]hexyl-3-(3,4-methylenedioxybenzyl))-2-cyclohexyl-2-hydroxy-2-phenyl acetamide (Compound No. 42), (1α,5α,6α)-6-N-(3-azabicyclo[3.1.0]hexyl-3-(6,6-dimethyl-2,4-heptadiynyl)-2-cyclohexyl-2-hydroxy-2-phenyl acetamide (Compound No. 43), (1α,5α,6α)-6-N-(3-azabicyclo[3.1.0]hexyl-3-benzoyl)-2-cyclohexyl-2-hydroxy-2-phenyl acetamide (Compound No. 44), (1α,5α,6α)-6-N-(3-azabicyclo[3.1.0]hexyl-3-(2-formyl-fur-5-yl))-2-cyclohexyl -2-hydroxy-2-phenyl acetamide (Compound No. 45), (1α,5α,6α)-6-N-(3-azabicyclo[3.1.0]hexyl-3-(aniline) thiourea)-2-cyclohexyl-2-hydroxy-2-phenyl acetamide (Compound No. 46), (1α,5α,6α)-6-N-(3-azabicyclo[3.1.0]hexyl-3-(methyl,4-amino-1-phenyl acetate)urea)-2-cyclohexyl-2-hydroxy-2-phenyl acetamide (Compound No. 47), (1α,5α,6α)-6-N-(3-azabicyclo[3.1.0]hexyl-3-(4-amino-1-phenyl acetic acid) urea)-2-cyclohexyl-2-hydroxy-2-phenyl acetamide (Compound No. 48), (1α,5α,6α)-6-N-(3-azabicyclo[3.1.0]hexyl-3-(4-methylphenyl-1-sulphonamide) urea)-2-cyclohexyl-2-hydroxy-2-phenyl acetamide (Compound No. 49), (1α,5α,6α)-6-N-(3-azabicyclo[3.1.0]hexyl-3-benzyl)-2-cyclohexyl-2-hydroxy-2-(4-methylphenyl)acetamide (Compound No. 50), (1α,5α,6α)-6-N-(3-azabicyclo[3.1.0]hexyl-3-benzyl)-2-cyclohexyl-2-hydroxy-2-(4-methoxyphenyl)acetamide (Compound No. 51), (1α,5α,6α)-6-N-(3-azabicyclo[3.1.0]hexyl-3-benzyl)-2-cyclohexyl-2-hydroxy-2-(4-phenoxyphenyl)acetamide (Compound No. 52), (1α,5α,6α)-6-N-(3-azabicyclo[3.1.0]hexyl-3-benzyl)-2-cyclohexyl-2-hydroxy-2-(4-fluorophenyl)acetamide (Compound No. 53).

(1α,5α,6α)-6-N-(3-azabicyclo[3.1.0]hexyl-3-benzyl)-2-cyclohexyl-2-hydroxy-2-(3,4-methylenedioxyphenyl) acetamide (Compound No. 54), (1α,5α,6α)-6-N-(3-azabicyclo[3.1.0]hexyl-3-benzyl)-2-cyclohexyl-2-hydroxy-2-(4-tertbutylphenyl)acetamide (Compound No. 55).

(1α,5α,6α)-6-N-(3-azabicyclo[3.1.0]hexyl-3-(4-methyl-3-pentenyl))-2-cyclohexyl-2-hydroxy-2-(4-methylphenyl)acetamide (Compound No. 56), (1α,5α,6α)-6-N-(3-azabicyclo[3.1.0]hexyl-3-(4-methyl-3-pentenyl))-2-cyclohexyl -2-hydroxy-2-(4-methoxyphenyl)acetamide (Compound No. 57), (1α,5α,6α)-6-N-(3-azabicyclo[3.1.0]hexyl-3-(4-methyl-3-pentenyl))-2-cyclohexyl-2-hydroxy-2-(4-fluorophenyl)acetamide (Compound No. 58), (1α,5α,6α)-6-N-(3-azabicyclo[3.1.0]hexyl-3-benzyl)-2-cyclohexyl-2-methoxy-2-phenyl acetamide (Compound No. 59), (1α,5α,6α)-6-N-(3-azabicyclo[3.1.0]hexyl-3-ethyl)-2-cyclohexyl-2-methoxy-2-phenyl acetamide (Compound No. 60), (1α,5α,6α)-6-N-(3-azabicyclo[3.1.0]hexyl-3-benzyl)-2-cyclohexyl-2-(2-propenyloxy)-2-phenyl acetamide (Compound No. 61), (1α,5α,6α)-6-N-(3-azabicyclo[3.1.0]hexyl-3-(4-methyl-3-pentenyl))-2-cyclohexyl-2-methoxy-2-phenyl acetamide (Compound No. 62), (1α,5α,6α)-6-N-(3-azabicyclo[3.1.0]hexyl-3-(2,4-difluorobenzyl))-2-cyclohexyl-2-methoxy-2-phenyl acetamide (Compound No. 63), (1α,5α,6α)-6-N-(3-azabicyclo[3.1.0]hexyl-3-benzyl)-2-cyclopentyl-2-hydroxy-2-phenyl acetamide (Compound No. 64), (1α,5α,6α)-6-N-(3-azabicyclo[3.1.0]hexyl-3-(4-methyl-3-pentenyl))-2-cyclopentyl-2-hydroxy-2-phenyl acetamide (Compound No. 65), (1α,5α,6α)-6-N-(3-azabicyclo[3.1.0]hexyl-3-(2-(3,4-methylenedioxyphenyl)ethyl)-2-cyclopentyl-2-hydroxy-2-phenyl acetamide (Compound No. 66), (1α,5α,6α)-6-N-(3-azabicyclo[3.1.0]hexyl-3-(2-phenylethyl))-2-cyclopentyl-2-hydroxy-2-phenyl acetamide (Compound No. 67), (1α,5α,6α)-6-N-(3-azabicyclo[3.1.0]hexyl-3-(2-(2,3-dihydrobenzofuran-5-yl)ethyl))-2-cyclopentyl-2-hydroxy-2-phenyl acetamide (Compound No. 68), (1α,5α,6α)-6-N-(3-azabicyclo[3.1.0]hexyl-3-(2-methylpyrid-6-yl)-2-cyclopentyl-2-hydroxy-2-phenyl acetamide (Compound No. 69), (1α,5α,6α)-6-N-(3-azabicyclo[3.1.0]hexyl-3-(1-(2,3-dihydrobenzofuran-5-yl) acetyl)-2-cyclopentyl-2-hydroxy-2-phenyl acetamide (Compound No. 70), (1α,5α,6α)-6-N-(3-azabicyclo[3.1.0]hexyl-3-(2-(benzofuran-5-yl)ethyl))-2-cyclopentyl-2-hydroxy-2-phenyl acetamide (Compound No. 71), (1α,5α,6α)-6-N-(3-azabicyclo[3.1.0]hexyl-3-benzyl)-2-cycloheptyl-2-hydroxy-2-phenyl acetamide (Compound No. 72), (1α,5α,6α)-6-N-(3-azabicyclo[3.1.0]hexyl-3-(4-methyl-3-pentenyl))-2-cycloheptyl-2-hydroxy-2-phenyl acetamide (Compound No. 73), 2-Amino-((1α,5α,6α)-6-N-(3-azabicyclo[3.1.0]hexyl-3-benzyl)propionamido)-2-cyclohexyl-2-hydroxy-2-phenyl acetamide (Compound No. 74), 2-Amino-((1α,5α,6α)-6-N-(3-azabicyclo[3.1.0]hexyl-3-benzyl)acetamido)-2-cyclohexyl-2-hydroxy-2-phenyl acetamide. (Compound No. 75), 3-Amino-((1α,5α,6α)-6-N-(3-azabicyclo[3.1.0]hexyl-3-benzyl)propionamido)-2-cyclohexyl-2-hydroxy-2-phenyl acetamide (Compound No. 76), (1α,5α,6α)-6-N-(3-azabicyclo[3.1.0]hexyl-3-benzyl)-3-cyclohexyl-3-hydroxy-3-phenyl propionamide (Compound No. 77), 2-Amino-((1α,5α,6α)-6-N-(3-azabicyclo[3.1.0]hexyl-3-benzyl)acetamido)-3-cyclohexyl-3-hydroxy-3-phenyl propionamide (Compound No. 78), 2-Amino-((1α,5α,6α)-6-N-(3-azabicyclo[3.1.0]hexyl-3-benzyl)propionamido)-2-cyclohexyl-3-hydroxy-3-phenyl propionamide (Compound No. 79), (1α,5α,6α)-2-[6-N-(3-benzyl-3-azabicyclo[3.1.0]hexyl)-N-propionamido-2-cyclohexyl-2-hydroxy-2-phenyl acetate (Compound No. 80), (2R)(1α,5α,6α)-6-N-(3-azabicyclo[3.1.0]hexyl-3-(4-methyl-3-pentenyl))-2-cyclopentyl-2-hydroxy-2-phenyl acetamide (Compound No. 81), (2R)(1α,5α,6α)-6-N-(3-azabicyclo[3.1.0]hexyl-3-(3,4-methylenedioxy phenyl)ethyl)-2-cyclopentyl-2-hydroxy-2-phenyl acetamide (Compound No. 82), (2R)-(1α,5α,6α)-6-N-(3-azabicyclo[3.1.0]hexyl-3-(4-methyl-3-pentenyl)-2-cyclopentyl-2-hydroxy-2-phenyl acetamide succinate salt. (Compound No. 83), (2R)-(1α,5α,6α)-6-N-(3-azabicyclo[3.1.0]hexyl-3-(4-methyl-3-pentenyl))-2-cyclopentyl-2-hydroxy-2-phenyl acetamide L-(+)-tartrate salt. (Compound No. 84), (1α,5α,6α)-6-N-(3-azabicyclo[3.1.0]hexyl)-2-cyclohexyl-2-hydroxy-2-phenyl acetamide (Compound No. 85), (1α,5α,6α)-6-N-(3-azabicyclo[3.1.0]hexyl)-2-cyclohexyl-2-hydroxy-2-(4-fluorophenyl)acetamide (Compound No. 86), (1α,5α,6α)-6-N-(3-azabicyclo[3.1.0]hexyl)-2-cyclohexyl-2-hydroxy-2-(4-methoxyphenyl)acetamide (Compound No. 87), (1α,5α,6α)-6-N-(3-azabicyclo[3.1.0]hexyl)-2-cyclohexyl-2-hydroxy-2-(4-methylphenyl)acetamide (Compound No. 88), (1α,5α,6α)-6-N-(3-azabicyclo[3.1.0]hexyl)-2-cyclopentyl-2-hydroxy-2-phenyl acetamide (Compound No. 89), (1α,5α,6α)-6-N-(3-azabicyclo[3.1.0]hexyl)-2-cycloheptyl-2-hydroxy-2-phenyl acetamide (Compound No. 90), (1α,5α,6α)-6-N-(3-azabicyclo[3.1.0]hexyl)-2-cyclobutyl-2-hydroxy-2-phenyl acetamide (Compound No. 91), (1α,5α,6α)-6-N-(3-azabicyclo[3.1.0]hexyl)-2-cyclopropyl-2-hydroxy-2-phenyl acetamide (Compound No. 92), (1α,5α,6α)-1-[6N-(3-azabicyclo[3.1.0]hexyl)]-N-acetamido-2-hydroxy-2-cyclohexyl-2-phenylacetate (Compound No. 93), (1α,5α,6α)-1-[6N-(3-azabicyclo[3.1.0]hexyl)]-N-propionamido-2-hydroxy-2-cyclohexyl-2-phenylacetate (Compound No. 94), (1α,5α,6α)-4-[6N-(3-azabicyclo[3.1.0]hexyl)]-N-(tert-butyloxy carbonyl)butyl-1-[2-hydroxy-2,2-bis(4-fluorophenyl)]acetate (Compound No. 95), (1α,5α,6α)-4-[6N-(3-azabicyclo[3.1.0]hexyl)]-N-(tert-butyloxy carbonyl)butyl-1-[2-propyloxy-2,2-bis(4-fluorophenyl)]acetate (Compound No. 96), (1α,5α,6α)-6N-(3-azabicyclo[3.1.0]hexyl)-2,2-diphenyl acetamide (Compound No. 97), (1α,5α,6α)-6N-(3-azabicyclo[3.1.0]hexyl)-2-cyclohexyl-2-methoxy-2-phenylacetamide (Compound No. 98).

8. A pharmaceutical composition comprising a therapeutically effective amount of a compound as defined in any of claims 1–7 together with pharmaceutically acceptable carriers, excipients or diluents.

9. A process of preparing a compound of Formula I,

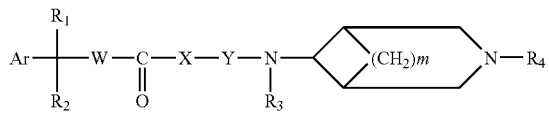

Formula I and its pharmaceutical acceptable salts, pharmaceutically acceptable solvates, esters, enantioners, diastereomers, or N-oxides, wherein Ar represents an aryl or a heteroaryl ring having 1–2 hetero atoms selected from the group consisting of oxygen, sulphur and nitrogen atoms, the aryl or heteroaryl rings may be unsubstituted or substituted by one to three substituents independently selected from straight or branched lower alkyl ($C_1$–$C_4$), trifluoromethyl, methylenedioxy, cyano, hydroxy, halogen (e.g. F, Cl, Br, I), nitro, lower alkoxy ($C_1$–$C_4$), aryloxy, amino or lower alkylamino;

$R_1$ represents $C_3$–$C_9$ cycloalkyl ring, a $C_3$–$C_9$ cyclo alkenyl ring, an aryl or a heteroaryl ring having 1 to 2 hetero atoms selected from the group consisting of oxygen, sulphur and nitrogen atoms; the aryl or a heteroaryl ring may be unsubstituted or substituted by one to three substituents independently selected from lower alkyl ($C_1$–$C_4$), trifluoromethyl, cyano, hydroxy, nitro, lower alkoxycarbonyl, halogen, lower alkoxy ($C_1$–$C_4$), unsubstituted amino or lower alkyl ($C_1$–$C_4$) amino;

$R_2$ represents a hydrogen, hydroxy, amino, alkoxy, alkenyloxy, alkynyloxy, carbamoyl or halogen (e.g. F, Cl, Br, I);

W represents $(CH_2)_p$, where p represents 0 to 1;

X represents an oxygen, sulphur, NR, or no atom, where R is H or lower alkyl ($C_1$–$C_4$);

Y represents $(CHR_5)q$ CO wherein $R_5$ represents hydrogen or methyl; or Y represents $(CH_2)q$ wherein q represents 0 to 4;

m represents 0 to 2;

$R_3$ represents hydrogen, lower alkyl or $CO_2C(CH_3)_3$;

$R_4$ represents hydrogen;

(a) condensing a compound of Formula VII with a compound of Formula VIII

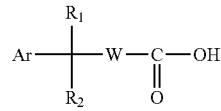

Formula VII

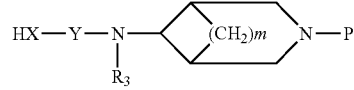

Formula VIII wherein Ar, $R_1$, $R_2$, $R_3$, W, X, Y and m have the same meanings as defined earlier, P is any group which can be used to protect an amino group, in the presence of a condensing agent to give a protected compound of Formula IX, and

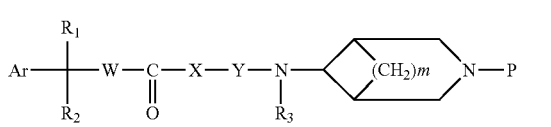

Formula IX (b) deprotecting the compound of Formula IX in the presence of a deprotecting agent to give a compound of Formula X, Formula X wherein Ar, $R_1$, $R_2$, $R_3$, W, X, Y, m and P are the same as defined earlier.

10. The process according claim 9 wherein the group P is selected from the group consisting of benzyl and tert-butyloxycarbonyl.

11. The process according to claim 9 wherein the condensing agent is selected from the group consisting of 1-(3-dimethylamino propyl)-3-ethyl carbodiimide hydrochloride (EDC) and 1,8-diazabicyclo[5.4.0]undec-7-ene (DBU).

12. The process according to claim 9 for preparing a compound of Formula II wherein $R_4$ is hydrogen Formula II 13. The process according to claim 9 wherein the compound of Formula III is prepared wherein $R_4$ is hydrogen Formula III 14. The process according to claim 9 wherein the compound of Formula IV is prepared wherein $R_4$ is hydrogen Formula IV 15. The process according to claim 14 wherein the compound of Formula V is prepared wherein $R_4$ is hydrogen Formula V 16. The process according to claim 15 wherein the compound of Formula VI is prepared wherein $R_4$ is hydrogen Formula VI 17. A process of preparing a compound of Formula I, Formula I and its pharmaceutical acceptable salts, pharmaceutically acceptable solvates, esters, enantiomers, diastereomers, N-oxides, polymorphs, prodrugs or metabolites wherein Ar represents an aryl or a heteroaryl ring having 1–2 hetero atoms selected from the group consisting of oxygen, sulphur and nitrogen atoms, the aryl or heteroaryl rings may be unsubstituted or substituted by one to three substituents independently selected from straight or branched lower alkyl ($C_1$–$C_4$), trifluoromethyl, methylenedioxy, cyano, hydroxy, halogen (e.g. F, Cl, Br, I), nitro, lower alkoxy ($C_1$–$C_4$), aryloxy, amino or lower alkylamino;

$R_1$ represents $C_3$–$C_9$ cycloalkyl ring, a $C_3$–$C_9$ cyclo alkenyl ring, an aryl or a heteroaryl ring having 1 to 2 hetero atoms selected from the group consisting of oxygen, sulphur and nitrogen atoms; the aryl or a heteroaryl ring may be unsubstituted or substituted by one to three substituents independently selected from lower alkyl ($C_1$–$C_4$), trifluoromethyl, cyano, hydroxy, nitro, lower alkoxycarbonyl, halogen, lower alkoxy ($C_1$–$C_4$), unsubstituted amino or lower alkyl ($C_1$–$C_4$) amino;

$R_2$ represents a hydrogen, hydroxy, amino, alkoxy, alkenyloxy, alkynyloxy, carbamoyl or halogen (e.g. F, Cl, Br, I);

W represents $(CH_2)_p$, where p represents 0 to 1;

X represents an oxygen, sulphur, NR, or no atom, where R is H or lower alkyl ($C_1$–$C_4$);

Y represents $(CHR_5)$q CO wherein $R_5$ represents hydrogen, or methyl; or Y represents $(CH_2)$q wherein q represents 0 to 4;

m represents 0 to 2;

$R_3$ represents hydrogen, lower alkyl or $CO_2C(CH_3)_3$;

$R_4$ represents $C_1$–$C_{15}$ saturated or unsaturated aliphatic hydrocarbon groups in which any 1 to 6 hydrogen atoms may be substituted with the group independently selected from halogen, arylalkyl, arylalkenyl, heteroarylalkyl or heteroarylalkenyl having 1 to 2 hetero atoms selected from the group consisting of nitrogen, oxygen and sulphur atoms with an option that any 1 to 3 hydrogen atoms on an aryl or heteroaryl ring in said arylalkyl, arylalkenyl, hetero arylalkenyl group may be substituted with lower alkyl, trifluoromethyl, cyano, hydroxyl, carboxylic acid, nitro, lower alkoxycarbonyl, halogen, lower alkoxy, amino, lower alkylamino, loweralkyl carbonyl amino, loweralkyl thiocarbonyl amino or loweralkyl carbonyl amino sulphonyl, comprising (a) condensing a compound of Formula VII with a compound of Formula VIII Formula VII

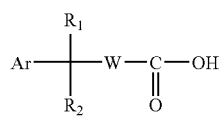

Formula VIII

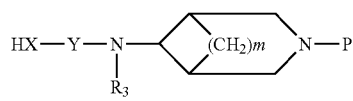

wherein Ar, $R_1$, $R_2$, $R_3$, W, X, Y and m have the same meanings as defined earlier, P is any group which can be used to protect an amino group, in the presence of a condensing agent to give a protected compound of Formula IX, Formula IX

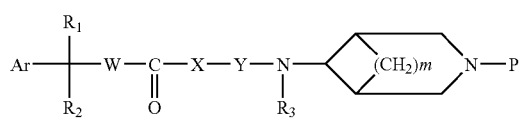

(b) deprotecting the compound of Formula IX in the presence of a deprotecting agent to give a compound of Formula X, Formula X

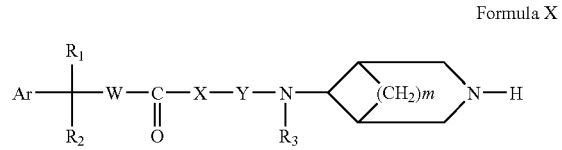

wherein Ar, $R_1$, $R_2$, $R_3$, W, X, Y, m and P are the same as defined earlier, and (c) N-alkylating or benzylating the compound of Formula X with a suitable alkylating or benzylating agent L-$R_4$ wherein L is a leaving group and $R_4$ is as defined earlier, to give a compound of Formula I.

18. The process according claim 17 wherein the group P is selected from the group consisting of benzyl and tert-butyloxycarbonyl.

19. The process according to claim 17 wherein the condensing agent is selected from the group consisting of 1-(3-dimethylamino propyl)-3-ethyl carbodiimide hydrochloride (EDC) and 1,8-diazabicyclo[5.4.0]undec-7-ene (DBU).

20. The process according to claim 17 for preparing a compound of Formula II

Formula II

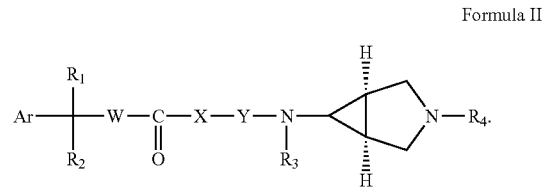

21. The process according to claim 17 wherein the compound of Formula III is prepared Formula III

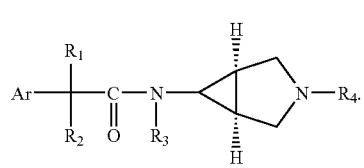

22. The process according to claim 17 wherein the compound of Formula IV is prepared Formula IV

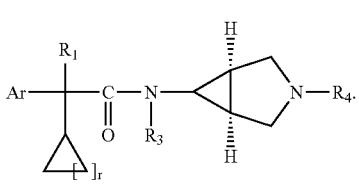

23. The process according to claim 22 wherein the compound of Formula V is prepared
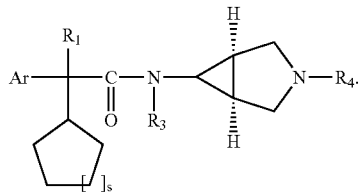
Formula V
24. The process according to claim 23 wherein the compound of Formula VI is prepared
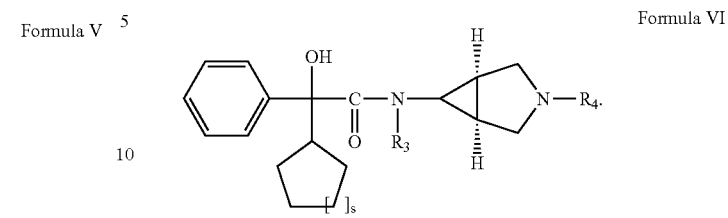
Formula VI
* * * * *